United States Patent
Holland et al.

(10) Patent No.: US 10,092,014 B2
(45) Date of Patent: Oct. 9, 2018

(54) METHOD FOR PREPARING AND PRESERVING SANITIZED PRODUCTS

(71) Applicant: aPEEL Technology, Inc., Goleta, CA (US)

(72) Inventors: Chance Holland, Goleta, CA (US); James Rogers, Goleta, CA (US); Stephen William Kaun, Santa Barbara, CA (US); Carlos Hernandez, Santa Barbara, CA (US); Alexander William Thomas, Santa Barbara, CA (US); Savannah Jane Dearden, Santa Barbara, CA (US)

(73) Assignee: Apeel Technology, Inc., Goleta, CA (US)

( * ) Notice: Subject to any disclaimer, the term of this patent is extended or adjusted under 35 U.S.C. 154(b) by 0 days.

(21) Appl. No.: 15/669,304

(22) Filed: Aug. 4, 2017

(65) Prior Publication Data

US 2017/0332650 A1    Nov. 23, 2017

Related U.S. Application Data

(63) Continuation of application No. PCT/US2017/014978, filed on Jan. 25, 2017.
(Continued)

(51) Int. Cl.
*A23B 7/154* (2006.01)
*C09D 5/14* (2006.01)
(Continued)

(52) U.S. Cl.
CPC ............... *A23B 7/154* (2013.01); *A01N 3/00* (2013.01); *A01N 25/02* (2013.01); *A01N 31/02* (2013.01);
(Continued)

(58) Field of Classification Search
CPC ........... A23B 7/154; A23B 7/16; A23P 20/11; A01N 25/02; A01N 31/02; A01N 37/12;
(Continued)

(56) References Cited

U.S. PATENT DOCUMENTS 2,213,557 A * 9/1940 Tisdale .................... A23B 7/16
                                                        426/300
2,275,659 A    3/1942 Steinle et al.
(Continued)

FOREIGN PATENT DOCUMENTS

CN    103719261    4/2014
DE    2505428      8/1976
(Continued)

OTHER PUBLICATIONS

English translation for JP62-126931 published Nov. 1987.*
(Continued)

*Primary Examiner* — Anthony J Weier
(74) *Attorney, Agent, or Firm* — Fenwick & West LLP

(57) ABSTRACT

Described herein are methods of sanitizing and preserving produce and other agricultural products, for example for consumption as Ready-to-Eat. The methods can comprise treating the products with a sanitizing agent and forming a protective coating over the products.

29 Claims, 25 Drawing Sheets

Related U.S. Application Data

(60) Provisional application No. 62/287,170, filed on Jan. 26, 2016.

(51) Int. Cl.

| | | |
|---|---|---|
| *A23L 3/349* | (2006.01) | |
| *A01N 25/02* | (2006.01) | |
| *A23P 20/10* | (2016.01) | |
| *A23B 7/16* | (2006.01) | |
| *A01N 37/12* | (2006.01) | |
| *A01N 31/02* | (2006.01) | |
| *C09D 7/00* | (2018.01) | |
| *A23L 3/3517* | (2006.01) | |
| *A01N 3/00* | (2006.01) | |
| *C09D 7/20* | (2018.01) | |

(52) U.S. Cl.
CPC .............. *A01N 37/12* (2013.01); *A23B 7/16* (2013.01); *A23L 3/349* (2013.01); *A23L 3/3517* (2013.01); *A23P 20/11* (2016.08); *C09D 5/14* (2013.01); *C09D 7/20* (2018.01); *A23V 2002/00* (2013.01)

(58) Field of Classification Search
CPC ......... A23L 3/349; A23L 3/3517; C09D 5/14; C09D 7/001; A23V 2002/00
See application file for complete search history.

(56) References Cited

U.S. PATENT DOCUMENTS

| | | | |
|---|---|---|---|
| 2,324,448 A * | 7/1943 | Wehrli | A23B 7/16 106/237 |
| 2,333,887 A | 11/1943 | Redlinger | |
| 2,363,232 A * | 11/1944 | Cothran | A23B 7/16 106/268 |
| 3,232,765 A | 2/1966 | Rosenthal et al. | |
| 3,997,674 A * | 12/1976 | Ukai | A23B 7/16 106/146.3 |
| 4,002,775 A | 1/1977 | Kabara | |
| 4,421,775 A | 12/1983 | Chan, Jr. | |
| 4,423,071 A | 12/1983 | Chignac et al. | |
| 4,654,370 A | 3/1987 | Marriot et al. | |
| 4,661,359 A * | 4/1987 | Seaborne | A23B 4/10 426/101 |
| 4,710,228 A | 12/1987 | Seaborne et al. | |
| 4,732,708 A | 3/1988 | Ekman et al. | |
| 4,962,885 A | 10/1990 | Coffee | |
| 5,051,448 A | 9/1991 | Shashoua | |
| 5,110,509 A | 5/1992 | Peter et al. | |
| 5,376,391 A * | 12/1994 | Nisperos-Carriedo | A23B 7/154 426/102 |
| 5,607,970 A | 3/1997 | Ishihara | |
| 5,658,768 A | 8/1997 | Quinlan | |
| 5,827,553 A | 10/1998 | Dimitroglou | |
| 5,832,527 A * | 11/1998 | Kawaguchi | G06F 17/30067 |
| 5,906,831 A | 5/1999 | Larsson et al. | |
| 5,925,395 A | 7/1999 | Chen | |
| 5,939,117 A | 8/1999 | Chen et al. | |
| 6,162,475 A | 12/2000 | Hagenmaier et al. | |
| 6,165,529 A * | 12/2000 | Yang | A23B 7/144 426/302 |
| 6,241,971 B1 | 6/2001 | Fox et al. | |
| 6,254,645 B1 | 7/2001 | Kellis et al. | |
| 6,255,451 B1 | 7/2001 | Koch et al. | |
| 6,294,186 B1 | 9/2001 | Beerse et al. | |
| 6,348,217 B1 | 2/2002 | Santos et al. | |
| 6,503,492 B2 | 1/2003 | McGlone et al. | |
| 7,373,135 B2 | 5/2008 | Najib-Fruchart et al. | |
| 7,550,617 B2 | 6/2009 | Imig et al. | |
| 7,732,470 B2 | 6/2010 | Imig et al. | |
| 7,785,897 B2 | 8/2010 | Agnes et al. | |
| 7,851,002 B2 | 12/2010 | Hekal et al. | |
| 7,931,926 B2 | 4/2011 | Lidster et al. | |
| 7,943,336 B2 | 5/2011 | Viksoe-Nielsen et al. | |
| 8,101,221 B2 | 1/2012 | Chen et al. | |
| 8,119,178 B2 | 2/2012 | Lidster et al. | |
| 8,197,870 B2 | 6/2012 | Krasutsky et al. | |
| 8,247,609 B2 | 8/2012 | Rogues et al. | |
| 8,263,751 B2 | 9/2012 | Peterson | |
| 8,424,243 B1 | 4/2013 | Narciso et al. | |
| 8,501,445 B2 | 8/2013 | Yoshikawa et al. | |
| 8,546,115 B2 | 10/2013 | Buchert et al. | |
| 8,609,169 B2 | 12/2013 | Chen et al. | |
| 8,752,328 B2 | 6/2014 | Kaiser et al. | |
| 8,846,355 B2 | 9/2014 | Yoshikawa et al. | |
| 9,095,152 B2 | 8/2015 | Munger | |
| 9,102,125 B2 | 8/2015 | Battersby et al. | |
| 9,284,432 B2 | 3/2016 | Yoshikawa et al. | |
| 9,770,041 B2 | 9/2017 | Dong et al. | |
| 2001/0042341 A1 | 11/2001 | Hamersky et al. | |
| 2002/0043577 A1 | 4/2002 | Krasutsky et al. | |
| 2004/0022906 A1 | 2/2004 | Petacvich | |
| 2004/0120919 A1 | 6/2004 | Nguyen et al. | |
| 2004/0220283 A1 | 11/2004 | Zhang et al. | |
| 2005/0233039 A1 * | 10/2005 | Wolfe | A23B 7/148 426/324 |
| 2007/0278103 A1 | 12/2007 | Hoerr et al. | |
| 2008/0026120 A1 * | 1/2008 | Petcavich | A23B 7/16 426/310 |
| 2008/0038471 A1 | 2/2008 | Boger et al. | |
| 2008/0254987 A1 | 10/2008 | Liu et al. | |
| 2008/0262190 A1 | 10/2008 | Koskimies et al. | |
| 2008/0310991 A1 * | 12/2008 | Webster | A01N 3/00 422/1 |
| 2009/0104446 A1 | 4/2009 | Guillet et al. | |
| 2009/0142453 A1 | 6/2009 | Lobisser et al. | |
| 2009/0152371 A1 | 6/2009 | Stark et al. | |
| 2009/0325240 A1 | 12/2009 | Daniell | |
| 2010/0029778 A1 | 2/2010 | Bailey et al. | |
| 2010/0186674 A1 | 7/2010 | Cahill, Jr. et al. | |
| 2010/0278784 A1 | 11/2010 | Pojasek et al. | |
| 2011/0244095 A1 * | 10/2011 | Sardo | A23B 7/154 426/302 |
| 2011/0280942 A1 * | 11/2011 | Schad | A61K 9/2813 424/476 |
| 2012/0251675 A1 * | 10/2012 | Sowa | A23B 7/154 426/102 |
| 2013/0209617 A1 | 8/2013 | Lobisser et al. | |
| 2013/0216488 A1 | 8/2013 | Hernandez-Brenes et al. | |
| 2014/0033926 A1 | 2/2014 | Fassel et al. | |
| 2014/0199449 A1 | 7/2014 | Hernandez et al. | |
| 2014/0205722 A1 * | 7/2014 | Quintanar Guerrero | A23L 3/3463 426/309 |
| 2014/0221308 A1 | 8/2014 | Baker et al. | |
| 2014/0234921 A1 | 8/2014 | Nyyssola et al. | |
| 2014/0348945 A1 | 11/2014 | Dong et al. | |
| 2015/0030780 A1 | 1/2015 | Rogers | |
| 2015/0079248 A1 * | 3/2015 | Nussinovitch | A01N 3/00 426/305 |
| 2016/0002483 A1 * | 1/2016 | Zhao | C09D 101/02 426/102 |
| 2016/0213030 A1 * | 7/2016 | Schad | A23P 20/105 |
| 2016/0256429 A1 | 9/2016 | Spanova et al. | |
| 2016/0324172 A1 * | 11/2016 | Williams | A01N 59/02 |
| 2017/0049119 A1 | 2/2017 | Perez et al. | |
| 2017/0073532 A1 | 3/2017 | Perez et al. | |
| 2018/0044276 A1 | 2/2018 | Perez et al. | |

FOREIGN PATENT DOCUMENTS

| | | |
|---|---|---|
| DE | 3622191 | 1/1988 |
| EP | 0104043 A2 | 3/1984 |
| EP | 1020124 A2 | 7/2000 |
| EP | 2389814 | 11/2011 |
| JP | 62-126931 * | 6/1987 |
| JP | 2009-527357 T | 7/2009 |
| WO | WO 93/06735 A1 | 4/1993 |
| WO | WO 2001/001980 A1 | 1/2001 |

(56) References Cited

FOREIGN PATENT DOCUMENTS

| WO | WO 2009/119730 A1 | 10/2009 |
|----|----|----|
| WO | WO 2011/014831 | 2/2011 |
| WO | WO 2012/042404 | 4/2012 |
| WO | WO 2015/017450 | 2/2015 |
| WO | WO 2015/028299 A1 | 3/2015 |
| WO | WO 2015/052433 | 4/2015 |
| WO | WO 2015/176020 | 11/2015 |
| WO | WO 2016/168319 A1 | 10/2016 |
| WO | WO 2016/187581 A1 | 11/2016 |
| WO | WO 2017/048951 | 3/2017 |
| WO | WO 2017/100636 | 6/2017 |
| WO | WO 2017/132281 | 8/2017 |

OTHER PUBLICATIONS

Andrade, Ricardo D. et al. "Atomizing spray systems for application of edible coatings", Comprehensive Reviews in Food Science and Food Safety, vol. 11, No. 3, 2012, p. 323-337.
Ayala-Zavala, J.F. et al., "High Relative Humidity In-Package of Fresh-Cut Fruits and Vegetables: Advantage or Disadvantage Considering Microbiological Problems and Antimicrobial Delivering Systems?", 2008, J. Food Science, vol. 73, p. R41-R47.
Ben-Yehoshua S. et al. "Modified-atmosphere packaging of fruits and vegetables: reducing condensation of water in bell peppers and mangoes", Acta Hort (ISHS), 1998, vol. 464, p. 387-92.
Bourtoom, T., "Edible films and coatings: characteristics and properties", International Food Research Journal, 2008, vol. 15, No. 3, pp. 237-248.
Deell JR et al. "Addition of sorbitol with KMnO4 improves broccoli quality retention in modified atmosphere packages", 2006, J Food Qual, vol. 29, p. 65-75.
Elgimabi and Ahmed, "Effects of Bactericides and Sucrose-Pulsing on Vase Life of Rose Cut Flowers (Rosa hybirida)", Botany Research International, 2009, 2(3) p. 164-168.
He et al. "Stem end blockage in cut Grevillea 'Crimson Yul-lo' inflorescences", Postharvest Biology and Technology, 2006, vol. 41, p. 78-84.
Hojjati et al. "Chemical Treatments of Eustoma Cut Flower Cultivars for Enhanced Vase Life", Journal of Agriculture and Social Sciences, 2007, vol. 3, No. 3, p. 75-78.
Javad et al. "Postharvest evaluation of vase life, stem bending and screening of cultivars of cut gerbera (Gerbera jamesonii Bolux ex. Hook f.) flowers", African Journal of Biotechnology 2011, 10(4), p. 560-566.
Javad et al. "Effect of Cultivar on Water Relations and Postharvest Quality ofGerbera (Gerbera jamesonii Bolus ex. Hook f.) Cut Flower", World Applied Sciences Journal, 2012, vol. 18, No. 5, p. 698-703.
Jones et al. "Pulsing with Triton X-100 Improves Hydration and Vase Life of Cut Sunflowers (Helianthus annuus L.)", HortScience, 1993, vol. 28, No. 12, p. 1178-1179.
Roy, S., et al. "Modified atmosphere and modified humidity packaging of fresh mushrooms" J Food Sci., 1996, vol. 61, p. 391-7.
Schreiber et al. "Transport barriers made of cutin, suberin and associated waxes", Trends in Plant Science, 2010, vol. 15, No. 10, p. 546-553.
Schweizer, P. et al. "Perception of free cutin monomers by plant cells", The Plant Journal, vol. 10, No. 2, 1996, p. 331-341.
Schweizer, P. et al. "Plant Protection by Free Cutin Monomers in Two Cereal Pathosystems", Advances in Molecular Genetics of Plant-Microbe Interactions, 1994, p. 371-374.
Shirazi A, et al. "Controlling relative humidity in modified atmosphere packages of tomato fruit", HortScience, 1992, vol. 27, p. 336-9.
Steuter et al. "Water Potential of Aqueous Polyethylene Glycol", 1981, Plant Physiol., vol. 67, p. 64-67.
Van Doorn et al. "Effects of surfactants on the longevity of dry-stored cut flowering stems of rose, Bouvardia, and Astilb", Postharvest Biology and Technology, 1993, vol. 3, pp. 69-76.
Van Doorn et al. "Alkylethoxylate surfactants for rehydration of roses and Bouvardia flowers", Postharvest Biology and Technology, 2002, vol. 24, p. 327-333.
Van Meeteren, "Water Relations and Keeping-Quality of Cut Gerbera Flowers. I. The Cause of Stem Break", Scientia Horticulturae, 1978, vol. 8, p. 65-74.
Alvaro, J. et al. "Effects of peracetic acid disinfectant on the postharvest of some fresh vegetables", Journal of Food Engineering, 2009, vol. 95, pp. 11-15.
Bewick, T., et al. "Evaluation of Epicuticular Wax Removal from Whole Leaves with Chloroform," Weed Technology, Jul.—SePages, 1993, vol. 7, No. 3, pp. 706-716.
Cantwell, M., "Properties and recommended conditions for long-term storage of fresh fruits and vegetables," Nov. 2001, 8 Pages.
Cochran, H.D. "Solvation in supercritical water", Fluid Phase Equilibria, 1992, vol. 71, pp. 1-16.
Gabler, M., et al. "Impact of Postharvest Hot Water or Ethanol Treatment of Table Grapes on Gray Mold Incidence, Quality, and Ethanol Content," Plant Disease, Mar. 2005, vol. 89, No. 3, pp. 309-316.
Gil, M. et al. "Fresh-cut product sanitation and wash water disinfection: Problems and solutions", International Journal of Food Microbiology, 2009, vol. 134, pp. 37-45.
Graca, J. et al., "Linear and branched poly (omega-hydroxyacid) esters in plant cutins," J. Agric. Food Chem., 2010, vol. 58, No. 17, pp. 9666-9674.
Hardenburg, R., et al., "The Commercial Storage of Fruits, Vegetables, and Florist and Nursery Stocks," United States Department of Agriculture, Agriculture Handbook No. 66, Sep. 1986, pp. 6-7, 30, 50-51.
Hauff, S. et al. "Determination of hydroxylated fatty acids from the biopolymer of tomato cutin and their fate during incubation in soil," Phytochemical Analysis, Aug. 26, 2010, vol. 21, No. 6, pp. 582-589.
Holcroft, D., "Water Relations in Harvested Fresh Produce," PEF White Paper No. 15-01, The Postharvest Education Foundation (PEF), May 2015, 16 Pages.
Jerome, F., et al. ""One pot" and selective synthesis of monoglycerides over homogeneous and heterogeneous guanidine catalysts" Green Chem., 2004, vol. 6, pp. 72-74.
Karabulut, O. et al. "Postharvest ethanol and hot water treatments of table grapes to control gray mold", Postharvest Biology and Technology, 2004, vol. 34, pp. 169-177.
Kolattukudy, P.E., "Cutin from plants," Biopolymers Online, 3a, 2005, 40 pages.
Krammer, P., et al. "Hydrolysis of esters in subcritical and supercritical water", Journal of Supercritical Fluids, 2000, vol. 16, pp. 189-206.
Loppinet-Serani, A. et al. "Supercritical water for environmental technologies", J Chem Technol Biotechnol, Jan. 12, 2010, vol. 85, pp. 583-589.
Matic, M., "The chemistry of Plant Cuticles: a study of cutin form Agave americana L.," 1956, Biochemical Journal, 1956, vol. 63, No. 1, pp. 168-176.
Mattson, F.H., et al., "Synthesis and properties of glycerides," J Lipid Research, Jul. 1962, vol. 3, No. 3, pp. 281-296.
Morton, H. "The Relationship of Concentration and Germicidal Efficiency of Ethyl Alcohol", Annals New York Academy of Sciences, 53(1), 1950, pp. 191-196.
Oh, D. et al. "Antimicrobial activity of ethanol, glycerol monolaurate or lactic acid against Listeria monocytogenes", International Journal of Food Microbiology, 1993, vol. 20, pp. 239-246.
Olmez, H. et al. "Potential alternative disinfection methods for organic fresh-cut industry for minimizing water consumption and environmental impact", LWT—Food Science and Technology, 2009, vol. 42, pp. 686-693.
Osman, S. F., et al., "Preparation, Isolation, and Characterization of Cutin Monomers and oligomers from Tomato Peels," J. Agric, Food Chem, 1999, vol. 47, No. 2, pp. 799-802.
Rutala, W. et al. "Guideline for Disinfection and Sterilization in Healthcare Facilities, 2008" CDC, 2008, 158 Pages.
Sasaki, M., et al. "Cellulose hydrolysis in subcritical and supercritical water", Journal of Supercritical Fluids, 1998, vol. 13, pp. 261-268.

(56) References Cited

OTHER PUBLICATIONS

Sasaki, M., et al. "Dissolution and Hydrolysis of Cellulose in Subcritical and Supercritical Water", Ind. Eng. Chem. Res., 2000, vol. 39, pp. 2883-2890.
Savage, P., "Organic Chemical Reactions in Supercritical Water", Chem. Rev., 1999, vol. 99, pp. 603-621.
Tanaka, M., et al., "Quantitative determination of isomeric glycerides, free fatty acids and triglycerides by thin layer chromatography-flame ionization detector system." Lipids, 1980, vol. 15, No. 10, pp. 872-875.
Weingartner, H., et al. "Supercritical water as a solvent", Angewandte Chemie, 2005, vol. 44, Issue 18, pp. 2672-2692.
Yeats, T., et al. "The identification of cutin synthase: formation of the plant polyester cutin," Nat Chem Biol. Jul. 2012, vol. 8, No. 7, pp. 609-611.
PCT International Search Report and Written Opinion for PCT/US2016/065917, dated Mar. 9, 2017, 10 Pages.
PCT International Search Report and Written Opinion for PCT/US2017/014978, dated Apr. 10, 2017, 13 Pages.
PCT International Search Report and Written Opinion for PCT/US2016/051936, dated Jan. 31, 2017, 18 Pages.
Banerjee, S., et al., "Review Article: Electrospray Ionization Mass Spectrometry: A Technique to Access the Information Beyond the Molecular Weight of the Analyte," International Journal of Analytical Chemistry, Nov. 2011, vol. 2012, Article ID 282574, 40 pages.
Bateman, A., et al., "The Effect of Solvent on the Analysis of Secondary Organic Aerosol Using Electrospray Ionization Mass Spectrometry," Environ. Sci. Technol., 2008, vol. 42, No. 19, pp. 7341-7346.
Bateman, A., et al, "Supporting Information for Manuscript es-2008-01226w—The Effect of Solvent on the Analysis of Secondary Organic Aerosol Using Electrospray Ionization Mass Spectrometry," [online] 2008; available from the Internet URL: http://aerosol.chem.uci.edu/publications/Irvine/2008.sub.—Bateman.sub.—EST.sub.—SOA.sub.—solvent.sub.—effects.sub.—supporting.sub.—info.pdf, 6 pages.
Cech, N., et al., "Practical Implications of Some Recent Studies in Electrospray Ionization Fundamentals," Mass Spectrometry Reviews, 2001, vol. 20, pp. 362-387.
Chen, D-R., et al., "Electrospraying of Conducting Liquids for Monodisperse Aerosol Generation in the 4 nm to 1.8 .mu.m Diameter Range," J. Aerosol Sci., 1995, vol. 26, No. 6, pp. 963-977.
Enke, C., "A Predictive Model for Matrix and Analyte Effects in Electrospray Ionization of Singly-charged Ionic Analytes," Analytical Chemistry, 1997, vol. 69, No. 23, pp. 4885-4893.
Gaskell, S., "Special Feature: Tutorial—Electrospray: Principles and Practice," J. Mass Spectrom, 1997, vol. 32, pp. 677-688.
Huang, T-Y., et al., "Electron Transfer Reagent Anion Formation via Electrospray Ionization and Collision-induced Dissociation," Anal Chem., 2006, vol. 78, No. 21, pp. 7387-7391.
Huang, N., et al., "Automation of a Fourier Transform Ion Cyclotron Resonance Mass Spectrometer for Acquisition, Analysis, and E-mailing of High-resolution Exact-mass Electrospray Ionization Mass Spectral Data," J. Am Soc Mass Spectrom, 1999, vol. 10, pp. 1166-1173.
Jaworek, A., "Electrospray Droplet Sources for Thin Film Deposition," J. Mater Sci, 2007, vol. 42, pp. 266-297.
Kebarle, P., "Special Feature: Commentary—A Brief Overview of the Present Status of the Mechanisms Involved in Electrospray Mass Spectrometry," J. Mass Spectrom, 2000, vol. 35, pp. 804-817.
Keller, B., et al., "Review Article: Interferences and Contaminants Encountered in Modern Mass Spectrometry," Analytica Chimica Acta, 2008, vol. 627, pp. 71-81.
Kroll, B., et al., "Review: Chemistry of Secondary Organic Aerosol: Formation and Evolution of Low-volatility Organics in the Atmosphere," Atmospheric Environment, 2008, vol. 42, pp. 3593-3624.
Li, M.,et al., "Direct Quantification of Organic Acids in Aerosols by Desorption Electrospray Ionization Mass Spectrometry," Atmospheric Environment, 2009, vol. 43, pp. 2717-2720.
Nizkorodov, S., et al., "Molecular Chemistry of Organic Aerosols through the Application of High Resolution Mass Spectrometry," Phys. Chem. Chem. Phys, 2011, vol. 13, pp. 3612-3629.
Takats, Z., et al., "Special Feature: Perspective—Ambient Mass Spectrometry Using Desorption Electrospray Ionization (DESI): Instrumentation, Mechanisms and Applications in Forensics, Chemistry, and Biology," J. Mass Spectrom, 2005, vol. 40, pp. 1261-1275.
Wang, R., et al., "Evolution of the Solvent Polarity in an Electrospray Plume," J. Am Soc Mass Spectrom, 2010, vol. 21, pp. 378-385.
Wikipedia, Anonymous "Paint-Wikipedia", Jul. 2013, 7 Pages. https://en.wikipedia.org/w/index.php?title=Paint&oldid=563291624.
Zhu, J., et al., "Focus: Electrospray—Formation and Decompositions of Chloride Adduct Ions, [M + Ci] , in Negative Ion Electrospray Ionization Mass Spectrometry," J. Am Soc Mass Spectrom, 2000, vol. 11, pp. 932-941.
Zhu, J., et al., "Ranking of a Gas-phase Acidities and Chloride Affinities of Monosaccharides and Linkage Specificity in Collision-induced Decompositions of Negative Ion Electrospray-generated Chloride Adducts of Oligosaccharides," J. Am Soc Mass Spectrom, 2001, vol. 12, pp. 1193-1204.
PCT International Search Report and Written Opinion in PCT/US2014/048707, dated Nov. 13, 2014, 12 pages.
PCT International Search Report and Written Opinion in PCT/US2017/024799, dated Jun. 8, 2017, 13 pages.
PCT International Search Report and Written Opinion in PCT/US2017/041167, dated Oct. 9, 2017, 20 pages.
Extended European Search Report for European Patent Application No. EP 14831592.2, dated Mar. 2, 2017, 9 pages.
Notice of Reasons for Rejection for Japanese Patent Application No. JP 2016-531832, dated Jul. 3, 2018, 13 Pages.

* cited by examiner

Coating Agent in 100% Ethanol

Coating Agent in 70% Ethanol

Coating Agent in 100% Ethanol

Coating Agent in 80% Ethanol

| Solution | 0 s | 5 s | 10 s | 1 min | 10 mins |
|---|---|---|---|---|---|
| Sterile DI H₂O | >85% Germination | >85% Germination | >85% Germination | >85% Germination | >85% Germination |
| 30% EtOH in DI H₂O | >85% Germination | >85% Germination | ~60% Germination | ~60% Germination | ~60% Germination |
| 70% EtOH in DI H₂O | >85% Germination | <2% Germination | <2% Germination | <2% Germination | <2% Germination |
| 100% EtOH in DI H₂O | >85% Germination | <2% Germination | <2% Germination | <2% Germination | <2% Germination |
| 70% EtOH in DI H₂O with coating agent | >85% Germination | <2% Germination | <2% Germination | <2% Germination | <2% Germination |
| 100% EtOH in DI H₂O with coating agent | >85% Germination | <2% Germination | <2% Germination | <2% Germination | <2% Germination |

FIG. 22

METHOD FOR PREPARING AND PRESERVING SANITIZED PRODUCTS

CROSS REFERENCE TO RELATED APPLICATIONS

This application is a continuation of PCT/US2017/014978, filed Jan. 25, 2017, now pending, which claims the benefit of priority to U.S. Provisional Patent Application Ser. No. 62/287,170, filed Jan. 26, 2016.

TECHNICAL FIELD

The present disclosure relates to formulations and methods for treating agricultural products, such as produce, such that the products are both sanitized and preserved.

BACKGROUND

Common agricultural products such as fresh produce are highly susceptible to degradation and decomposition (i.e., spoilage) when exposed to the environment. The degradation of the agricultural products can occur via abiotic means as a result of evaporative moisture loss from an external surface of the agricultural products to the atmosphere and/or oxidation by oxygen that diffuses into the agricultural products from the environment and/or mechanical damage to the surface and/or light-induced degradation (i.e., photodegradation). Furthermore, biotic stressors such as, for example, bacteria, fungi, viruses, and/or pests can also infest and decompose the agricultural products.

Prior to being consumed, agricultural products are typically washed (e.g., soaked or rinsed in water) to remove dust, dirt, pesticides, and/or bacteria that may be harmful if consumed. While washing can occur prior to packaging of the agricultural products for subsequent sale, washing processes typically accelerate the degradation and spoilage of the agricultural products. As such, many agricultural products are best preserved and maintained in a fresh state without spoilage if they are not washed prior to purchase, but are instead washed by consumers after purchase and just prior to consumption.

In recent years, there has been a push towards production of produce that is "Ready-to-Eat" (also referred to as "RTE") without requiring washing or other preparation by the consumer. Prior to being displayed for sale, Ready-to-Eat produce must be washed/cleaned and sanitized in order to lower pathogen concentrations to levels that ensure that a consumer will not be in danger of contracting illnesses or death. However, similar to washing procedures, many methods for safe sanitization of agricultural products also accelerate the degradation and spoilage of the products, as well as inducing damage. As such, methods for preparing Ready-to-Eat produce require processes that sanitize the produce in a manner that is both safe for consumption and which does not substantially degrade the quality of the produce or cause it to spoil prematurely.

SUMMARY

Described herein are methods of preparing produce and other agricultural products for consumption, for example as Ready-to-Eat. The methods serve both to sanitize the agricultural products and also to preserve the products and extend their shelf life so that they remain fresh and can, for example, be designated as Ready-to-Eat, without causing mechanical damage to or substantially affecting the taste, odor, or appearance of the products.

Accordingly, in one aspect, a method of sanitizing and preserving produce includes providing a solution comprising water, a sanitizing agent, and a coating agent, wherein the coating agent comprises a plurality of monomers, oligomers, fatty acids, esters, amides, amines, thiols, carboxylic acids, ethers, aliphatic waxes, alcohols, salts (inorganic and organic), or combinations thereof (herein referred to as "coating components"). In some embodiments, the coating agent comprises a compound of Formula I. The solution is applied to a surface of the produce for a time sufficient to sanitize the produce. At least a portion of the water and the sanitizing agent are removed from the surface of the produce, and at least a portion of the coating agent remains on the surface of the produce as a protective coating after the water and the sanitizing agent are at least partially removed.

In another aspect, a method of treating edible produce includes providing a solution comprising a coating agent dissolved in a solvent, where the coating agent includes a plurality of monomers, oligomers, fatty acids, esters, amides, amines, thiols, carboxylic acids, ethers, aliphatic waxes, alcohols, salts, or combinations thereof, and the solvent comprises water and ethanol, wherein the solvent is between 50% and 90% ethanol by volume. The solution is applied to a surface of the edible produce for a time sufficient for the solvent to sanitize the produce and to cause a protective coating to be formed over the surface of the produce from the coating agent. The solvent is then at least partially removed from the surface of the edible produce.

In yet another aspect, a method of treating produce with a sanitizing solution is described, where the sanitizing solution includes a coating agent dissolved in a solvent, and the solvent includes a sanitizing agent. The sanitizing solution is applied to a surface of the produce and is allowed to contact the surface of the produce for a time period sufficient for the sanitizing agent to reduce bacteria levels on the surface of the produce. The solvent is then allowed to at least partially evaporate, thereby causing a protective coating to form from the coating agent over the surface of the produce.

In still another aspect, a method of treating produce includes providing a solution comprising a coating agent dissolved in a solvent, the solvent comprising a sanitizing agent. The solution is applied to a surface of the produce to sanitize the produce, and the solvent is then at least partially removed from the surface of the produce, causing a protective coating to be formed from the coating agent over the surface of the produce.

In still another aspect, a method of treating an edible product such as produce includes providing a solution comprising a non-sanitizing coating agent dissolved in a solvent, wherein the solvent comprises a sanitizing agent. The solution is applied to a surface of the edible product, thereby allowing the solvent to sanitize the edible product. The solvent is then removed from the surface of the edible product, and a protective coating is formed from the non-sanitizing coating agent over the surface of the edible product.

Methods described herein can each include one or more of the following features, either alone or in any combination. A protective coating formed from the coating agent can serve to prevent damage to the produce or edible product caused by the sanitizing agent, or to replace or reinforce portions of the produce or edible product which are damaged by the sanitizing agent. The protective coating can further serve to increase the shelf life of the produce or edible product. The protective coating can serve to reduce a mass loss rate of the produce or edible product. The coating agent can form an edible coating over the produce or edible product. The solution can comprise between 50% and 90% ethanol by volume or between 60% and 80% ethanol by volume. The produce or edible product can be a thin skin fruit or vegetable, a berry, a grape, or an apple. In some embodiments, the coating agent includes at least one of monomers, oligomers, fatty acids, esters, amides, amines, thiols, carboxylic acids, ethers, aliphatic waxes, alcohols, or salts. The monomers, oligomers, fatty acids, esters, amides, amines, thiols, carboxylic acids, ethers, aliphatic waxes, alcohols, salts, or combinations thereof can be derived from plant matter. The monomers, oligomers, fatty acids, esters, amides, amines, thiols, carboxylic acids, ethers, aliphatic waxes, alcohols, salts, or combinations thereof can be derived from cutin.

In some embodiments of any of the above-aspects, the solvent can comprise water. In some embodiments of any of the above-aspects, the sanitizing agent is ethanol (e.g., dissolved in water). In some embodiments, the solvent contains at least 30% ethanol (e.g., at least 30%, at least 35%, at least 40%, at least 45%, at least 50%, at least 55%, at least 60%, at least 65%, at least 70%, at least 75%, at least 80%, at least 85%, at least 90%, or at least 95%). In some embodiments, the coating agents described herein (e.g., compounds of Formula I) are insufficient to sanitize the edible substrate alone. In some embodiments, sanitizing the edible substrate comprises preventing fungal growth on the edible substrate.

The sanitizing agent can comprise ethanol, methanol, acetone, isopropanol, ethyl acetate, or combinations thereof. A volume ratio of the sanitizing agent to water in the solution can be in a range of about 1 to 10. The monomers, oligomers, fatty acids, esters, amides, amines, thiols, carboxylic acids, ethers, aliphatic waxes, alcohols, salts, or combinations thereof can comprise one or more compounds of Formula I:

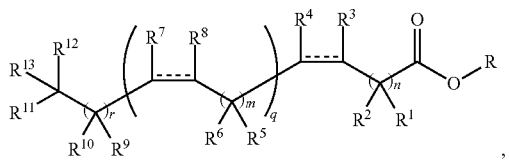

(Formula I)

wherein:

R is selected from —H, —$C_1$-$C_6$ alkyl, —$C_2$-$C_6$ alkenyl, —$C_2$-$C_6$ alkynyl, —$C_3$-$C_7$ cycloalkyl, aryl, or heteroaryl, wherein each alkyl, alkenyl, alkynyl, cycloalkyl, aryl, or heteroaryl is optionally substituted with one or more $C_1$-$C_6$ alkyl or hydroxy;

$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, —$SR^{14}$, halogen, —$C_1$-$C_6$ alkyl, —$C_2$-$C_6$ alkenyl, —$C_2$-$C_6$ alkynyl, —$C_3$-$C_7$ cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, $SR^{14}$, or halogen;

$R^3$, $R^4$, $R^7$ and $R^8$ are each independently, at each occurrence, —H, —$OR^{14}$, —$NR^{14}R^{15}$, $SR^{14}$, halogen, —$C_1$-$C_6$ alkyl, —$C_2$-$C_6$ alkenyl, —$C_2$-$C_6$ alkynyl, —$C_3$-$C_7$ cycloalkyl, aryl, or heteroaryl, wherein each alkyl, alkenyl, alkynyl, cycloalkyl, aryl, or heteroaryl is optionally substituted with —$OR^{14}$, —$NR^{14}R^{15}$, $SR^{14}$, or halogen; or $R^3$ and $R^4$ can combine with the carbon atoms to which they are attached to form a $C_3$-$C_6$ cycloalkyl, a $C_4$-$C_6$ cycloalkenyl, or 3- to 6-membered ring heterocycle; and/or $R^7$ and $R^8$ can combine with the carbon atoms to which they are attached to form a $C_3$-$C_6$ cycloalkyl, a $C_4$-$C_6$ cycloalkenyl, or 3- to 6-membered ring;

$R^{14}$ and $R^{15}$ are each independently, at each occurrence, —H, —$C_1$-$C_6$ alkyl, —$C_2$-$C_6$ alkenyl, or —$C_2$-$C_6$ alkynyl;

the symbol ------ represents an optionally single or cis or trans double bond;

n is 0, 1, 2, 3, 4, 5, 6, 7, or 8;

m is 0, 1, 2, or 3;

q is 0, 1, 2, 3, 4, or 5; and r is 0, 1, 2, 3, 4, 5, 6, 7, or 8.

The monomers, oligomers, fatty acids, esters, amides, amines, thiols, carboxylic acids, ethers, aliphatic waxes, alcohols, salts, or combinations thereof can comprise monoacylglycerides. The solution can be applied to the surface of the produce or edible product for between 1 and 3,600 seconds. Sanitizing the produce or edible product can result in reduced bacteria, viral, or fungal levels on the surface of the produce or edible product. The steps of sanitizing the produce and forming the protective coating over the surface of the produce can result in the produce being Ready-to-Eat. The steps of sanitizing the produce or edible product and forming the protective coating over the surface of the produce or edible product can result in an increase in the shelf life of the produce or edible product as compared to untreated produce or edible products. A concentration of the coating agent dissolved in the solution can be in a range of about 0.1 mg/mL to 200 mg/mL or 0.5 mg/mL to 200 mg/mL. The step of sanitizing the produce or edible product can further comprise sterilizing the produce or edible product.

At least partially removing of the solvent from the surface of the produce or edible product can comprise removing at least 90% of the solvent from the surface of the produce or edible product. Applying the solution to the surface of the produce or edible product can comprise dipping the produce or edible product in the solution or spraying the solution on the surface of the produce or edible product. The solvent can include at least one of ethanol and water. The sanitizing agent can include at least one of ethanol, methanol, acetone, isopropanol, and ethyl acetate. The coating agent can be formulated to prevent damage to the produce or edible product caused by the sanitizing agent. The coating agent can be formulated such that the protective coating reduces a rate of water loss from the produce or edible product. The sanitizing agent can be ethanol, and the sanitizing solution can include at least 30% ethanol by volume, between about 50% and about 90% ethanol by volume, or between 60% and 80% ethanol by volume. The coating agent can include monoacylglycerides. The time period can be in a range of 1 second to 3,600 seconds or a range of 5 seconds to 600 seconds. The treated produce can be labeled as Ready-to-Eat.

The coating agent can comprise a plurality of monomers, oligomers, fatty acids, esters, amides, amines, thiols, carboxylic acids, ethers, aliphatic waxes, alcohols, salts, or combinations thereof. The coating agent can be a non-sanitizing coating agent. The solvent can further comprise water. The sanitizing agent can comprise an alcohol. The sanitizing agent can comprise ethanol, methanol, acetone, isopropanol, or ethyl acetate. Sanitizing the produce or edible product can result in a reduction in a rate of fungal growth on the produce or edible product, or in an increase in the shelf life of the produce or edible product prior to fungal growth.

As used herein, "plant matter" refers to any portion of a plant, for example, fruits (in the botanical sense, including fruit peels and juice sacs), leaves, stems, barks, seeds, flowers, or any other portion of the plant.

As used herein, a "coating agent" refers to a chemical formulation that can be used to coat the surface of a substrate (e.g., after removal of a solvent in which the coating agent is dispersed). The coating agent can comprise one or more coating components. For example, the coating components can be compounds of Formula I, or monomers or oligomers of compounds of Formula I. Coating components can also comprise fatty acids, fatty acid esters, fatty acid amides, amines, thiols, carboxylic acids, ethers, aliphatic waxes, alcohols, salts (inorganic and organic), or combinations thereof As used herein, the term "sanitizing" or "sanitize" is understood to mean a chemical process that lessens or kills microorganisms (e.g., germs) on a surface (e.g., the surface of produce), for example to make the surface (e.g., of the produce) safe to eat. In some embodiments, sanitizing kills or removes most of the microorganisms on a surface. For instance, sanitizing can kill or remove at least 95%, at least 98%, at least 99%, at least 99.99%, or at least 99.9999% of microorganisms on a surface. In some embodiments, sanitization of produce is sufficient to make the produce ready to eat.

As used herein, "sterilizing" or "disinfecting" is understood to mean the removal of substantially all microorganisms on a surface (e.g., the surface of produce). In some embodiments, sanitization can comprise sterilizing or disinfecting the piece of produce. In some embodiments, sterilization or disinfection of produce is sufficient to make the produce ready to eat. In some embodiments, the act of sanitizing a piece of produce comprises sterilizing the produce. In some embodiments of the methods described herein, the process can both sanitize and sterilize the produce treated.

As used herein, the term "non-sanitizing" is understood to be descriptive of a compound, coating, formulation, or the like which is incapable of or does not sanitize objects or surfaces with which it comes into contact. For example, a "non-sanitizing coating agent" refers to a coating agent having a chemical composition which does not independently sanitize a surface to which the coating agent is applied and/or over which a coating is formed from the coating agent. In some embodiments, a solution including a non-sanitizing coating agent as a solute is operable to sanitize a surface to which it is applied when the solvent in which the solute is dissolved includes or is formed of a sanitizing agent.

As used herein, the term "about" and "approximately" generally mean plus or minus 10% of the value stated, e.g., about 250 µm would include 225 µm to 275 µm, about 1,000 µm would include 900 µm to 1,100 µm.

As used herein, the term "alkyl" refers to a straight or branched chain saturated hydrocarbon. $C_1$-$C_6$ alkyl groups contain 1 to 6 carbon atoms. Examples of a $C_1$-$C_6$ alkyl group include, but are not limited to, methyl, ethyl, propyl, butyl, pentyl, isopropyl, isobutyl, sec-butyl and tert-butyl, isopentyl and neopentyl.

As used herein, the term "alkenyl" means an aliphatic hydrocarbon group containing a carbon—carbon double bond and which may be straight or branched. Some alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms. As defined herein, the term "alkenyl" can include both "E" and "Z" or both "cis" and "trans" double bonds.

As used herein, the term "alkynyl" means an aliphatic hydrocarbon group containing a carbon—carbon triple bond and which may be straight or branched. Some alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

As used herein, the term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

As used herein, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment.

As used herein, the term "heteroaryl" means a monovalent monocyclic or bicyclic aromatic radical of 5 to 12 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom(s) is selected from N, O, or S. The aromatic radical is optionally substituted independently with one or more substituents described herein.

As used herein, the term "halo" or "halogen" means fluoro, chloro, bromo, or iodo.

BRIEF DESCRIPTION OF THE DRAWINGS

FIG. 22 is a table listing percent germination of *Penicillium* spores after incubation on slides coated with fruit wax and after treatment with solutions of the present disclosure.

DETAILED DESCRIPTION

Figure 1:
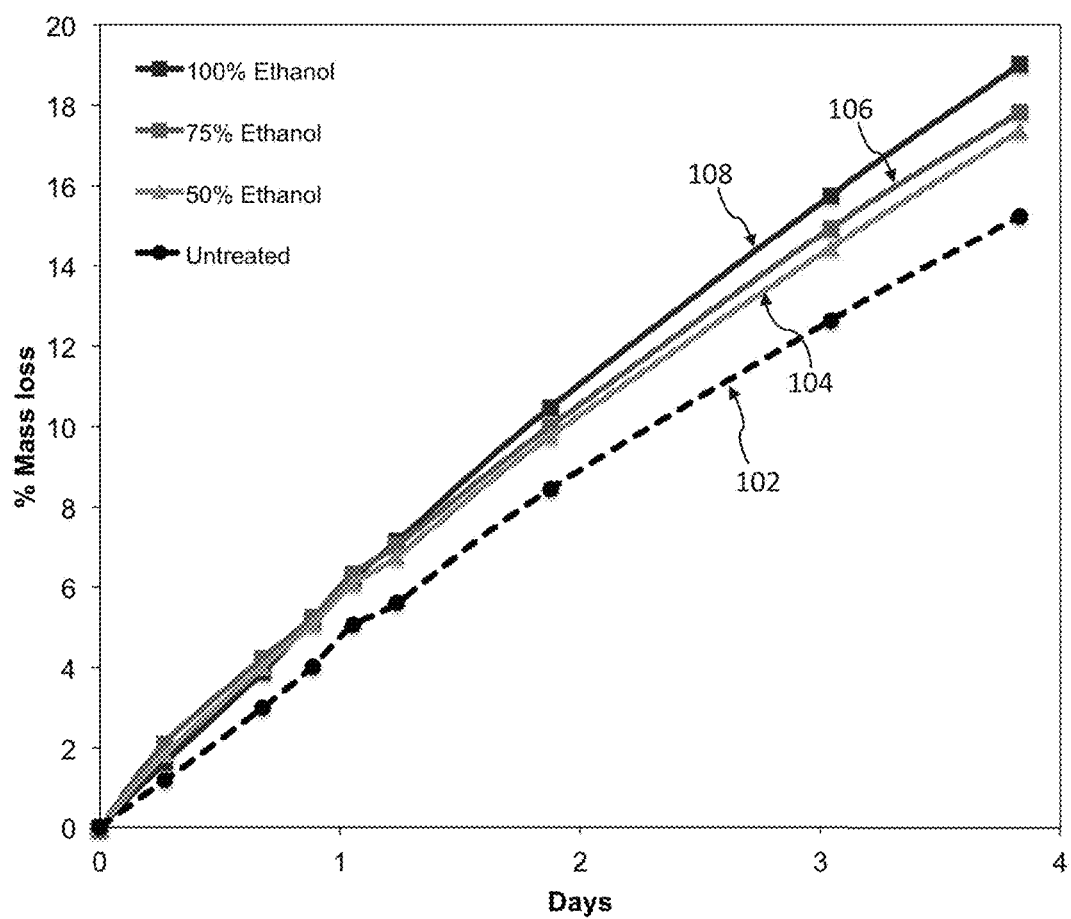
FIG. 1 shows plots of percent mass loss of blueberries versus time for untreated blueberries and for blueberries that have been treated with a sanitizing agent.

Described herein are methods of preparing produce and other products for consumption, for example as Ready-to-Eat. The methods serve both to sanitize the products and also to preserve the products and extend their shelf life so that they remain fresh and can, for example, be designated as Ready-to-Eat produce, without causing mechanical damage to or substantially affecting the taste, odor, or appearance of the products. The methods generally include treating the surface of the product with a solution which includes a composition of monomers, oligomers, fatty acids, esters, amides, amines, thiols, carboxylic acids, ethers, aliphatic waxes, alcohols, salts (inorganic and organic), or combinations thereof (coating components) dissolved in a solvent, the solvent including a sanitizing agent. In some embodiments, the sanitizing agent is ethanol. The solution is applied to the surface of the product for a time sufficient for the sanitizing agent to sanitize the surface of the product, after which the solvent is removed from the surface, for example by evaporation, blowing with fans, heating, toweling, or combinations thereof. Application of the solution to the surface further results in a protective coating being formed on the surface from the coating components, as further described below. In some embodiments in which the product is produce, the protective coating, which remains on the surface after the solvent is removed, prevents damage to the surface caused by the solvent and results in an increase in the shelf life of the produce as compared to similar produce which has been harvested but is otherwise untreated. In other embodiments in which the product is produce, the protective coating remains on the surface after the solvent is removed and replaces and/or reinforces portions of the natural coating covering of the produce (e.g., the cuticular layer) which are damaged by the solvent, thereby mitigating or eliminating the deleterious effects the solvent has on the surface, and in some cases improving the ability of the produce to prevent post-harvest water loss, oxidation, or other forms of degradation. The composition of the coating components can be formulated such that the coating is both edible and substantially undetectable. As such, coated agricultural products can, for example, be packaged and sold as Ready-to-Eat.

Many agricultural products such as fresh-cut fruits and vegetables are consumed without being cooked, thereby causing a risk to the consumer of illness caused by pathogen contamination. In recent years, a number of outbreaks have been traced to agricultural products processed under conditions that were not sufficiently sanitary. Direct sanitization of post-harvest (and in some cases pre-harvest) agricultural products is typically performed in order to minimize the risk of such contamination. Furthermore, many agricultural products are prone to molding or other degradation by biotic stressors during storage and/or shipping. For example, many agricultural products are shipped over long geographical distances from the growers' locations to the sellers' locations, often requiring them to be stored for extended periods of time during shipping (e.g., 30 days or longer). In order to prevent or mitigate water and mass loss from the products during shipping, the products are typically shipped in a high relative humidity atmosphere (e.g., 90% or 95% relative humidity). While such high relative humidity conditions are effective at reducing the rate of mass loss from the products, they also create an environment ideally suited for fungal and other microbial growth. Sanitizing the agricultural products prior to storing and shipping can reduce the rate of molding or other microbial contamination. However, it is important that the sanitization process causes little or no physical damage to the surface of the products, does not adversely impact the taste of the products, and does not leave harmful residuals on the products.

In the case of Ready-to-Eat agricultural products, in order for the products to be marketed and sold as Ready-to-Eat, they need to be sanitized prior to packaging. The sanitization process is preferably one that causes little or no physical damage to the products. Furthermore, after sanitization and packaging, the products need to remain fresh until they are sold and consumed.

Common chemical methods for cleaning and sanitizing agricultural and other food products typically include application of mechanical washing in the presence of a sanitizing agent such as peracetic acid, chlorine, chlorine dioxide, calcium hypochlorite, or sodium hypoclorite. However, many of these sanitizing agents present other safety concerns when residual concentrations that remain on the food products are too high.

Other solvents such as ethanol, methanol, acetone, isopropanol, and ethyl acetate are known to be effective sanitizing agents, and agricultural products treated with these agents can be sufficiently sanitized so as to be safe for consumption. At least some of these solvents (e.g., ethanol) are also safe for consumption in much higher concentrations than many of the sanitizing agents typically used to sanitize agricultural and food products. However, a problem arises in that these sanitizing agents typically damage the agricultural products and substantially reduce their shelf life, particularly in the case of thin skinned fruits and vegetables such as berries and grapes, as well as produce that has been cut to expose an inner surface. For example, as detailed below with reference to FIG. 1, treating harvested produce such as blueberries with ethanol typically causes an increase in the rate of mass loss of the produce. While such problems can in some cases be partially mitigated by diluting the sanitizing agent(s) in water, solutions for which the sanitizing agent is less than about 30% by volume, for example less than about 50% by volume, may not be effective at sufficiently sanitizing the agricultural product, for example to enable its use in Ready-to-Eat applications. Furthermore, as demonstrated below, solutions for which any of the above sanitizing agents is greater than 50% (and typically greater than 30%) by volume tend to damage the surface of the agricultural products and/or substantially reduce their shelf life.

In many cases, the damage caused to produce by sanitizing agents applied to the surface of the produce results in an increase in the rate of post-harvest mass loss. This occurs because the sanitizing agent can remove or damage at least a portion of the produce's natural barrier to water loss (e.g., the cuticular layer that covers the produce). For example, FIG. 1 shows plots of percent mass loss of blueberries versus time. The blueberries were all harvested simultaneously and divided into groups, each of the groups being qualitatively identical to the other groups (i.e., all groups had blueberries of approximately the same average size and quality). The first group of blueberries (corresponding to 102 in FIG. 1) was not washed or treated in any way, the second group (corresponding to 104 in FIG. 1) was treated in a 1:1 mixture of ethanol and water, the third group (corresponding to 106 in FIG. 1) was treated in a 3:1 mixture of ethanol and water, and the fourth group (corresponding to 108 in FIG. 1) was treated in substantially pure ethanol. As shown in FIG. 1, the untreated blueberries exhibited a substantially lower rate of mass loss during the four days after harvesting as compared to the blueberries that had been subjected to ethanol or to ethanol/water mixtures. Specifically, after just under four days, the untreated blueberries (102) experienced an average percent mass loss of about 15.4%, the blueberries treated in the 1:1 mixture of ethanol and water (104) experienced an average percent mass loss of about 17.4%, the blueberries treated in the 3:1 mixture of ethanol and water (106) experienced an average percent mass loss of about 17.7%, and the blueberries treated in substantially pure ethanol (108) experienced an average percent mass loss of about 19%.

Figure 3:
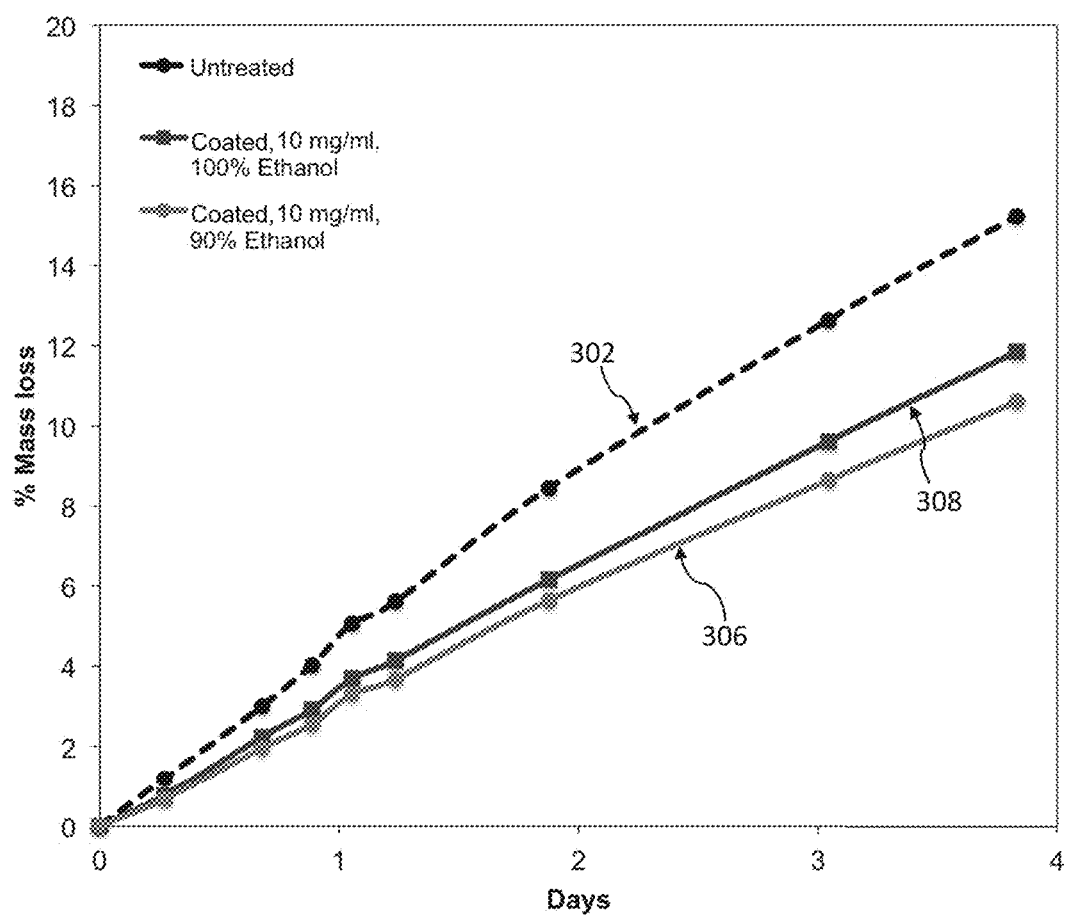
FIG. 3 shows plots of percent mass loss of blueberries versus time for untreated blueberries and for blueberries that have been treated with a solution including both a coating agent and a sanitizing agent.

FIG. 3 shows plots of percent mass loss of blueberries versus time for both untreated blueberries (plot 302, which is the same as plot 102 shown in FIG. 1) and for blueberries treated with solutions including both a sanitizing agent and a coating agent (plots 308 and 306), as in the method described below. The first group of blueberries (corresponding to 302 in FIG. 3) was not washed or treated in any way, the second group (corresponding to 308 in FIG. 3) was treated in a solution including a coating agent dissolved in substantially pure ethanol, and the third group (corresponding to 306 in FIG. 3) was treated in a solution including a coating agent dissolved in a 9:1 mixture of ethanol and water (i.e., 90% ethanol, 10% water). For both plots 308 and 306, the coating agent included a 3:1 mixture (by mass) of 1,3-dihydroxypropan-2-yl hexadecanoate (2-monoacylglycerides) and 2,3-dihydroxypropan-2-yl hexadecanoate (1-monoacylglycerides) dissolved in the solvent at a concentration of 10 mg/mL.

As shown in FIG. 3, the blueberries treated with solutions including both a sanitizing agent and a coating agent exhibited a substantially lower rate of mass loss during the four days after harvesting as compared to the untreated blueberries. This was unexpected in that it is exactly opposite to the trend illustrated in FIG. 1, for which blueberries treated with solutions including the sanitizing agent but not the coating agent exhibited substantially higher rates of mass loss than untreated blueberries. Accordingly, in some embodiments, the coatings of the present disclosure can mitigate and in some cases reverse the detrimental effects of sanitizing agents (e.g., ethanol). Referring again to FIG. 3, after just under four days, the untreated blueberries (302) experienced an average percent mass loss of about 15.4%, the blueberries treated in the solution including the coating agent dissolved in substantially pure ethanol (308) experienced an average percent mass loss of about 11.8%, and the blueberries treated in the solution including the coating agent dissolved in the 9:1 mixture of ethanol and water (306) experienced an average percent mass loss of about 10.6%.

Figure 4:
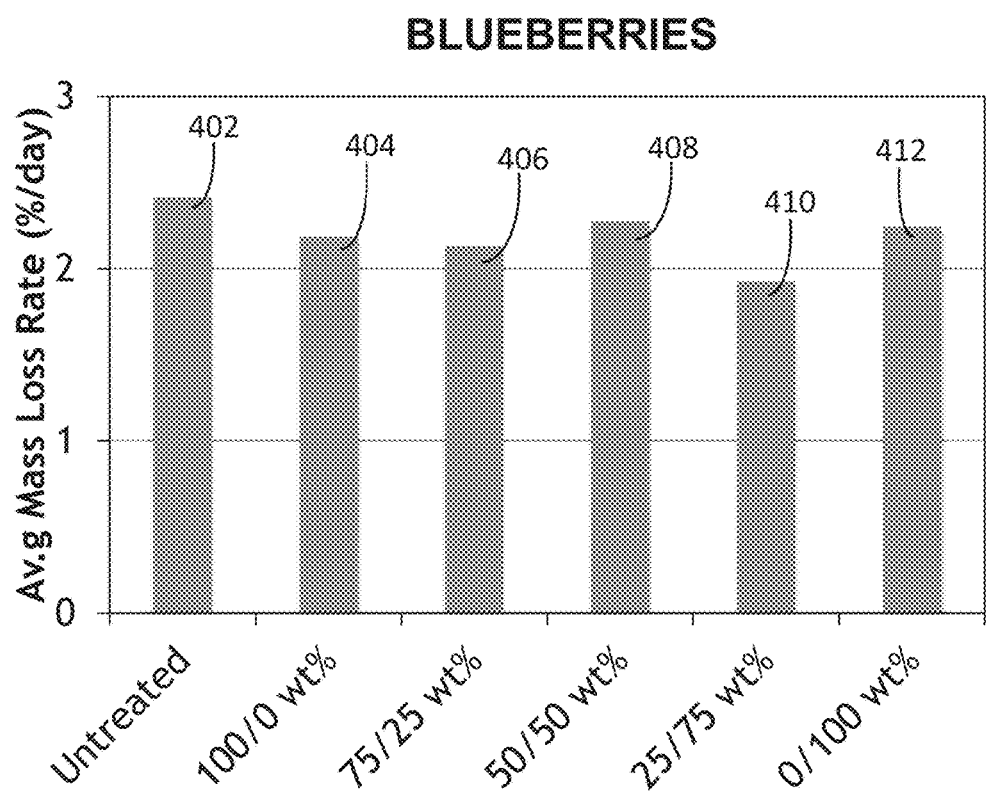
FIG. 4 is a plot of average mass loss rates of untreated blueberries and of blueberries that have been treated with a solution including both a coating agent comprising $C_{16}$ glycerol esters and a sanitizing agent.

FIG. 4, which examines the effect of various compositions of $C_{16}$ glycerol esters, is a graph showing average daily mass loss rates for blueberries, measured over the course of several days, where the blueberries were treated with a solution including a coating agent and a sanitizing agent. The coating agents included various mixtures of 1,3-dihydroxypropan-2-yl hexadecanoate and 2,3-dihydroxypropan-2-yl hexadecanoate, as detailed below. Each bar in the graph represents average daily mass loss rates for a group of 60 blueberries. The blueberries corresponding to bar 402 were untreated (control group). The blueberries corresponding to bar 404 were treated with a solution for which the coating agent was substantially pure 2,3-dihydroxypropan-2-yl hexadecanoate. The blueberries corresponding to bar 406 were treated with a solution for which the coating agent was about 75% 2,3-dihydroxypropan-2-yl hexadecanoate and 25% 1,3-dihydroxypropan-2-yl hexadecanoate by mass. The blueberries corresponding to bar 408 were treated with a solution for which the coating agent was about 50% 2,3-dihydroxypropan-2-yl hexadecanoate and 50% 1,3-dihydroxypropan-2-yl hexadecanoate by mass. The blueberries corresponding to bar 410 were treated with a solution for which the coating agent was about 25% 2,3-dihydroxypropan-2-yl hexadecanoate and 75% 1,3-dihydroxypropan-2-yl hexadecanoate by mass. The blueberries corresponding to bar 412 were treated with a solution for which the coating agent was substantially pure 1,3-dihydroxypropan-2-yl hexadecanoate. The coating agents were each dissolved in substantially pure ethanol (sanitizing agent) at a concentration of 10 mg/mL to form the solution, and the solution was applied to the surfaces of the blueberries to sanitize the surfaces and to form coatings.

As shown in FIG. 4, the untreated blueberries (402) exhibited an average mass loss rate of nearly 2.5% per day, which was more than the blueberries treated with a coating agent and sanitizing agent of the present disclosure. The lowest percent mass loss was seen in blueberries coated with 25% 2,3-dihydroxypropan-2-yl hexadecanoate and 75% 1,3-dihydroxypropan-2-yl hexadecanoate. The mass loss rates of the blueberries treated with the substantially pure 2,3-dihydroxypropan-2-yl hexadecanoate formulation (404) and the substantially pure 1,3-dihydroxypropan-2-yl hexadecanoate formulation (412), as well as the blueberries corresponding to bars 406 (2,3-dihydroxypropan-2-yl hexadecanoate to 1,3-dihydroxypropan-2-yl hexadecanoate mass ratio of about 3) and 408 (2,3-dihydroxypropan-2-yl hexadecanoate to 1,3-dihydroxypropan-2-yl hexadecanoate mass ratio of about 1) exhibited average daily mass loss rates between 2.1% and 2.3%, which was better (lower) than the untreated blueberries (402). The blueberries corresponding to bar 410 (2,3-dihydroxypropan-2-yl hexadecanoate to 1,3-dihydroxypropan-2-yl hexadecanoate mass ratios of about 0.33) exhibited mass loss rates under 2%, which was a substantial improvement over the untreated blueberries (402).

Figure 5:
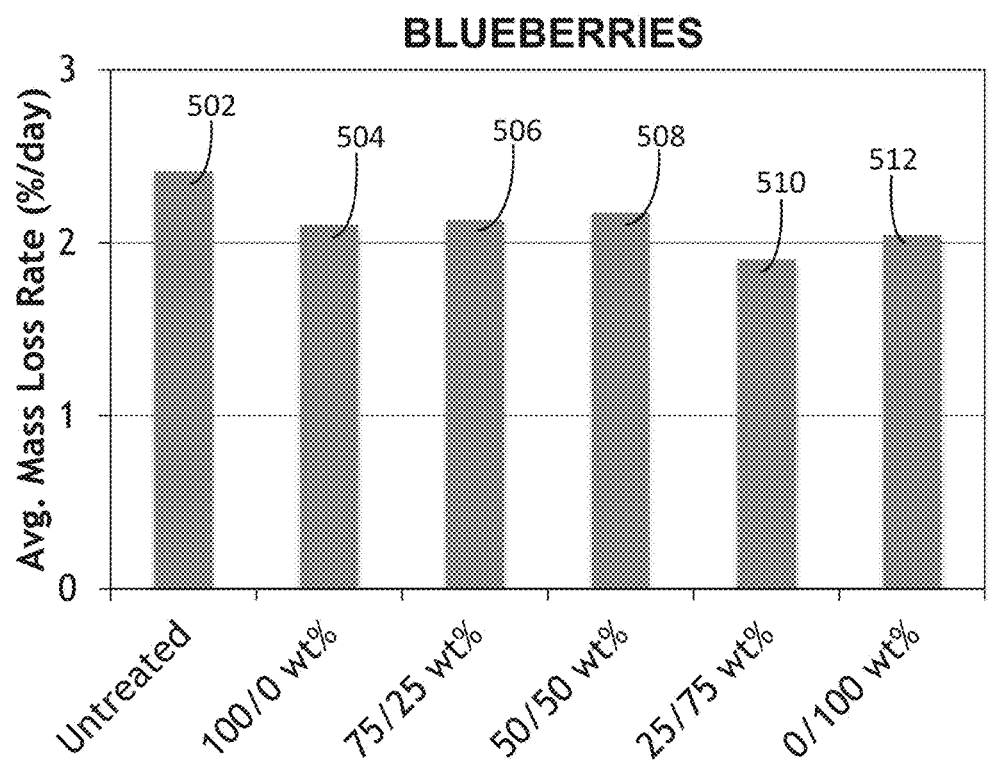
FIG. 5 is a plot of average mass loss rates of untreated blueberries and of blueberries that have been treated with a solution including both a coating agent comprising $C_{18}$ glycerol esters and a sanitizing agent.

FIG. 5, which examines the effect of various compositions of $C_{18}$ glycerol esters, is a graph showing average daily mass loss rates for blueberries, measured over the course of several days, where the blueberries were treated with a solution including a coating agent and a sanitizing agent. The coating agents included various mixtures of 1,3-dihydroxypropan-2-yl octadecanoate and 2,3-dihydroxypropan-2-yl octadecanoate, as detailed below. Each bar in the graph represents average daily mass loss rates for a group of 60 blueberries. The blueberries corresponding to bar 502 were untreated (control group). The blueberries corresponding to bar 504 were treated with a solution for which the coating agent was substantially pure 2,3-dihydroxypropan-2-yl octadecanoate. The blueberries corresponding to bar 506 were treated with a solution for which the coating agent was 75% 2,3-dihydroxypropan-2-yl octadecanoate and 25% 1,3-dihydroxypropan-2-yl octadecanoate by mass. The blueberries corresponding to bar 508 were treated with a solution for which the coating agent was 50% 2,3-dihydroxypropan-2-yl octadecanoate and 50% 1,3-dihydroxypropan-2-yl octadecanoate by mass. The blueberries corresponding to bar 510 were treated with a solution for which the coating agent was 25% 2,3-dihydroxypropan-2-yl octadecanoate and 75% 1,3-dihydroxypropan-2-yl octadecanoate by mass. The blueberries corresponding to bar 512 were treated with a solution for which the coating agent was substantially pure 1,3-dihydroxypropan-2-yl octadecanoate. The coating agents were each dissolved in substantially pure ethanol (sanitizing agent) at a concentration of 10 mg/mL to form the solution, and the solution was applied to the surfaces of the blueberries to sanitize the surfaces and to form coatings.

As shown in FIG. 5, the results for 2,3-dihydroxypropan-2-yl octadecanoate/1,3-dihydroxypropan-2-yl octadecanoate coating agent mixtures were similar to those for 2,3-dihydroxypropan-2-yl hexadecanoate/1,3-dihydroxypropan-2-yl hexadecanoate coating agent mixtures in FIG. 4. The untreated blueberries (502) exhibited an average mass loss rate of about 2.4% per day, which was higher than blueberries coated with a composition of the present disclosure. The lowest percent mass loss was seen in blueberries coated with 25% 2,3-dihydroxypropan-2-yl octadecanoate and 75% 1,3-dihydroxypropan-2-yl octadecanoate. The mass loss rates of the blueberries treated with the substantially pure 2,3-dihydroxypropan-2-yl octadecanoate formulation (504) and the substantially pure 1,3-dihydroxypropan-2-yl octadecanoate formulation (512), as well as the blueberries corresponding to bars 506 (2,3-dihydroxypropan-2-yl octadecanoate to 1,3-dihydroxypropan-2-yl octadecanoate mass ratio of about 3) and 508 (2,3-dihydroxypropan-2-yl octadecanoate to 1,3-dihydroxypropan-2-yl octadecanoate mass ratio of about 1) exhibited average daily mass loss rates between 2.1% and 2.2%, which was better than the untreated blueberries (502). The blueberries corresponding to bar 510 (2,3-dihydroxypropan-2-yl octadecanoate to 1,3-dihydroxypropan-2-yl octadecanoate mass ratio of about 0.33) exhibited average mass loss rates of about 1.8%, which was a substantial improvement over the untreated blueberries (502). Accordingly, without wishing to be bound by theory, as set forth in FIGS. 4 and 5, compositions comprising 1-monoacylglycerides and/or 2-monoacylglycerides (e.g., about 25% 1-monoacylglycerides and about 75% 2-monoacylglycerides) can be effective at reducing mass loss rates in sanitized produce.

Figure 6:
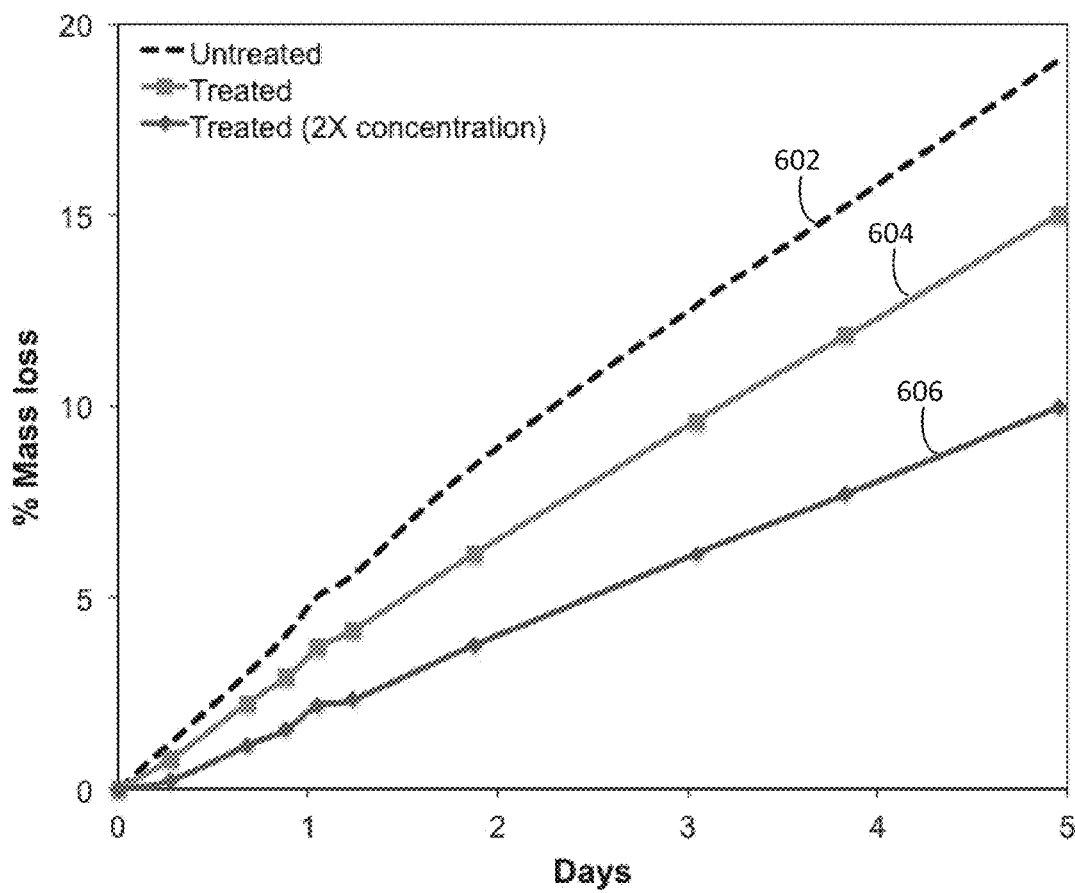
FIG. 6 is a plot of the percent mass loss of blueberries as a function of time.

FIG. 6, which examines the effect of coating agent concentration on mass loss rates, shows plots of the percent mass loss over the course of 5 days in untreated blueberries (602), blueberries treated with a first solution of 10 mg/mL of coating agent compounds dissolved in ethanol (604), and blueberries treated with a second solution of 20 mg/mL of coating agent compounds dissolved in ethanol (606). The coating agents in both the first and second solutions included a mixture of 2,3-dihydroxypropan-2-yl hexadecanoate and 1,3-dihydroxypropan-2-yl hexadecanoate, where the mass ratio of 2,3-dihydroxypropan-2-yl hexadecanoate to 1,3-dihydroxypropan-2-yl hexadecanoate was 0.33. As shown, the percent mass loss for untreated blueberries was almost 20% after 5 days, whereas the percent mass loss for blueberries treated with the 10 mg/mL solution was less than 15% after 5 days, and the percent mass loss for blueberries treated with the 20 mg/mL solution was less than 10% after 5 days. Accordingly, without wishing to be bound by theory, higher concentrations of coating agent can lead to further reduction in mass loss rates of sanitized produce.

Figure 7:
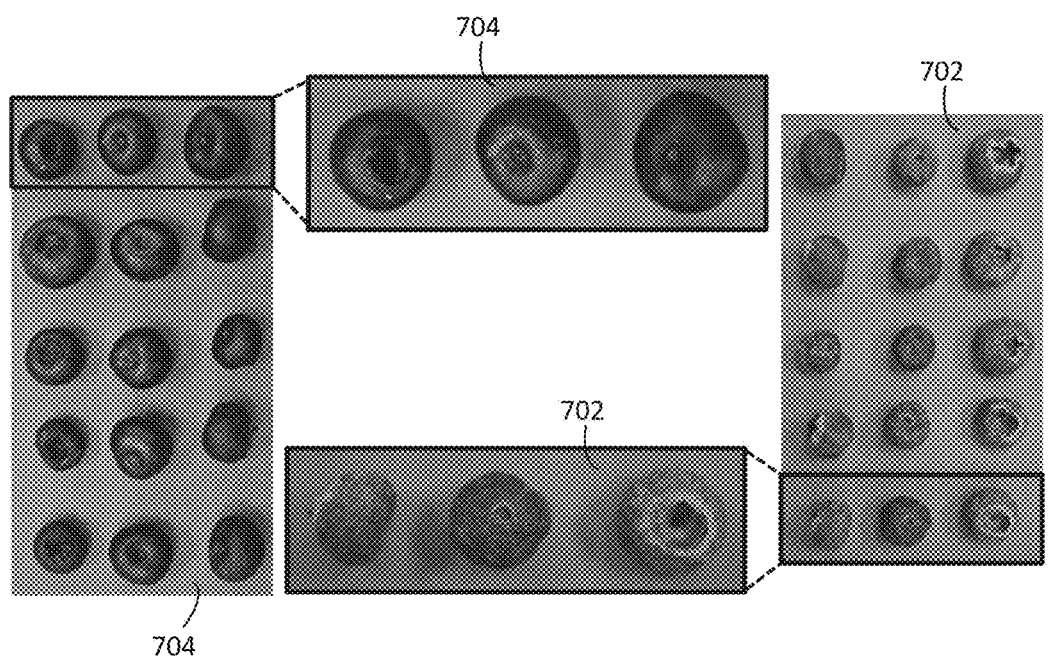
FIG. 7 shows high resolution photographs of treated and untreated blueberries.

FIG. 7 shows high resolution photographs of the untreated blueberries (602) from the study in FIG. 6, and of the blueberries treated with the 10 mg/mL solution of a 1:3 mass ratio of 2,3-dihydroxypropan-2-yl hexadecanoate to 1,3-dihydroxypropan-2-yl hexadecanoate (604) from the study of FIG. 6, taken at day 5. The skins of the untreated blueberries 602 were highly wrinkled as a result of mass loss of the blueberries, whereas the skins of the treated blueberries remained very smooth.

Figure 8:
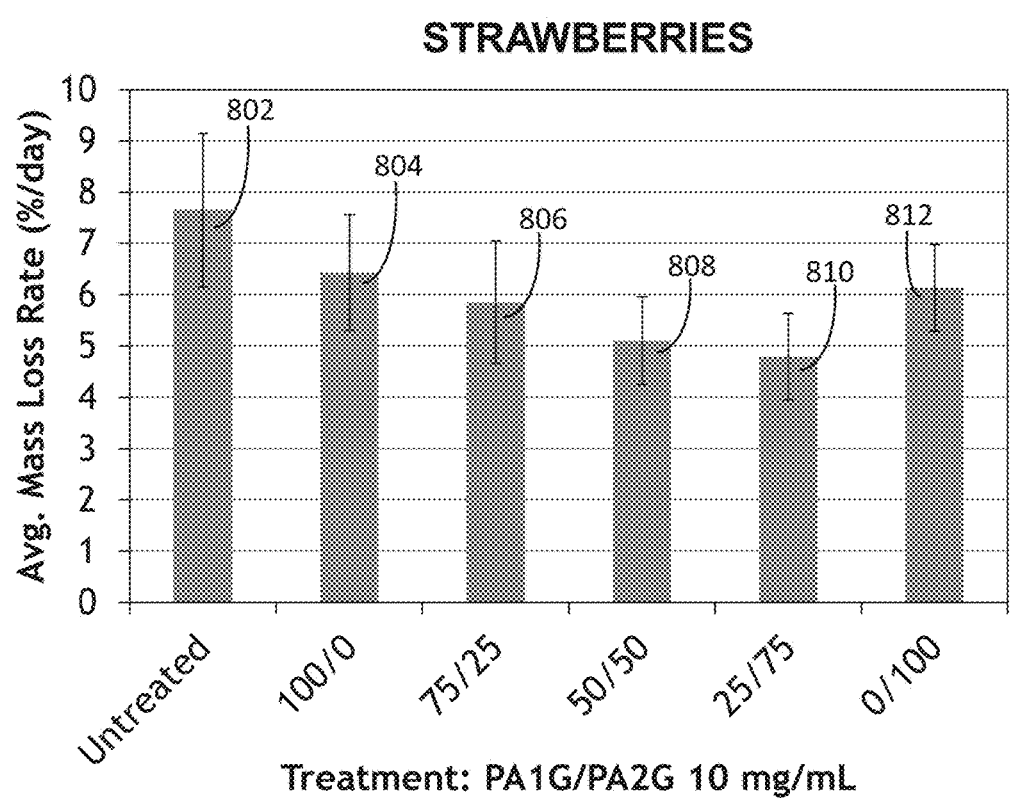
FIG. 8 is a plot of average mass loss rates of untreated strawberries and of strawberries that have been treated with a solution including both a coating agent comprising $C_{16}$ glycerol esters and a sanitizing agent.

FIG. 8 is a graph showing average daily mass loss rates for strawberries, measured over the course of 4 days, where the strawberries were treated with a solution including a coating agent and a sanitizing agent. The coating agents included various mixtures of 2,3-dihydroxypropan-2-yl hexadecanoate and 1,3-dihydroxypropan-2-yl hexadecanoate, as detailed below. Each bar in the graph represents average daily mass loss rates for a group of 15 strawberries. The strawberries corresponding to bar 802 were untreated (control group). The strawberries corresponding to bar 804 were treated with a solution for which the coating agent was substantially pure 2,3-dihydroxypropan-2-yl hexadecanoate. The strawberries corresponding to bar 806 were treated with a solution for which the coating agent was 75% 2,3-dihydroxypropan-2-yl hexadecanoate and 25% 1,3-dihydroxypropan-2-yl hexadecanoate by mass. The strawberries corresponding to bar 808 were treated with a solution for which the coating agent was 50% 2,3-dihydroxypropan-2-yl hexadecanoate and 50% 1,3-dihydroxypropan-2-yl hexadecanoate by mass. The strawberries corresponding to bar 810 were treated with a solution for which the coating agent was 25% 2,3-dihydroxypropan-2-yl hexadecanoate and 75% 1,3-dihydroxypropan-2-yl hexadecanoate by mass. The strawberries corresponding to bar 812 were treated with a solution for which the coating agent was substantially pure 1,3-dihydroxypropan-2-yl hexadecanoate. The coating agents were each dissolved in substantially pure ethanol (sanitizing agent) at a concentration of 10 mg/mL to form the solution, and the solution was applied to the surfaces of the strawberries to sanitize the surfaces and to form coatings.

As shown in FIG. 8, the untreated strawberries (802) exhibited an average mass loss rate of greater than 7.5% per day. The mass loss rates of the strawberries treated with the substantially pure 2,3-dihydroxypropan-2-yl hexadecanoate formulation (804) and the substantially pure 1,3-dihydroxypropan-2-yl hexadecanoate formulation (812) exhibited average daily mass loss rates between 6% and 6.5%, which was better than that of the untreated strawberries (802). The strawberries corresponding to bar 806 (2,3-dihydroxypropan-2-yl hexadecanoate to 1,3-dihydroxypropan-2-yl hexadecanoate mass ratio of 3) exhibited even lower mass loss rates, slightly less than 6% per day. The strawberries corresponding to bars 808 and 810 (2,3-dihydroxypropan-2-yl hexadecanoate to 1,3-dihydroxypropan-2-yl hexadecanoate mass ratios of 1 and 0.33, respectively) exhibited substantially improved mass loss rates; the strawberries corresponding to bar 808 exhibited average daily mass loss rates of just over 5%, while the strawberries corresponding to bar 810 exhibited average daily mass loss rates of under 5%.

Figure 9:
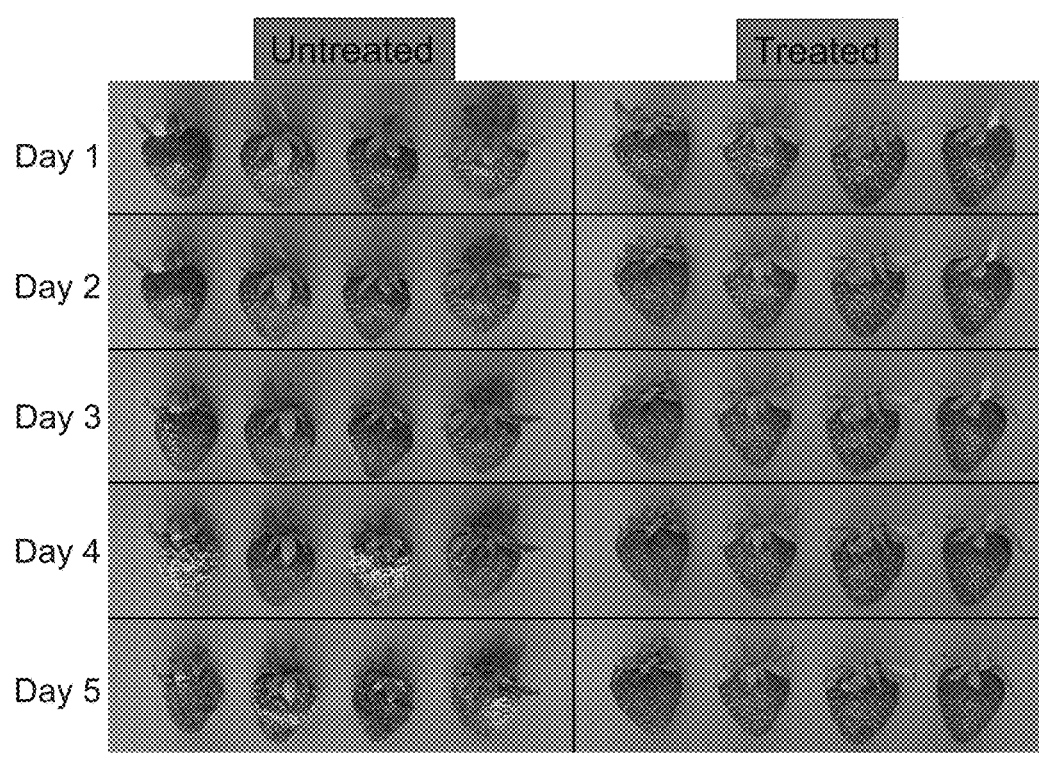
FIG. 9 shows high resolution time lapse photographs of treated and untreated strawberries.

FIG. 9 shows high resolution photographs of 4 coated and 4 uncoated strawberries over the course of 5 days. The strawberries were kept under ambient room conditions at a temperature in the range of about 23° C.-27° C. and humidity in the range of about 40%-55% for the entire duration of the time they were tested. The coated strawberries were treated with a solution for which the coating agent was a mixture of 2,3-dihydroxypropan-2-yl hexadecanoate and 1,3-dihydroxypropan-2-yl hexadecanoate combined at a mass ratio of 0.33, as in bar 810 in FIG. 8. As seen, the untreated strawberries began to exhibit fungal growth and discoloration by day 3, and were mostly covered in fungus by day 5. In contrast, the treated strawberries did not exhibit any fungal growth by day 5 and were largely similar in overall color and appearance on day 1 and day 5. Accordingly, without wishing to be bound by theory, as set forth in FIGS. 8 and 9, treating produce with a solution which includes a coating agent comprising 1-monoacylglycerides and/or 2-monoacylglycerides dissolved in a sanitizing agent can be effective at reducing a rate of and/or delaying the onset of fungal growth while at the same time reducing a mass loss rate of the produce. That is, the treatment can reduce the rate of fungal growth over the produce, and/or can increase the shelf life of the produce prior to fungal growth, while at the same time reducing a mass loss rate of the produce.

Figure 10:
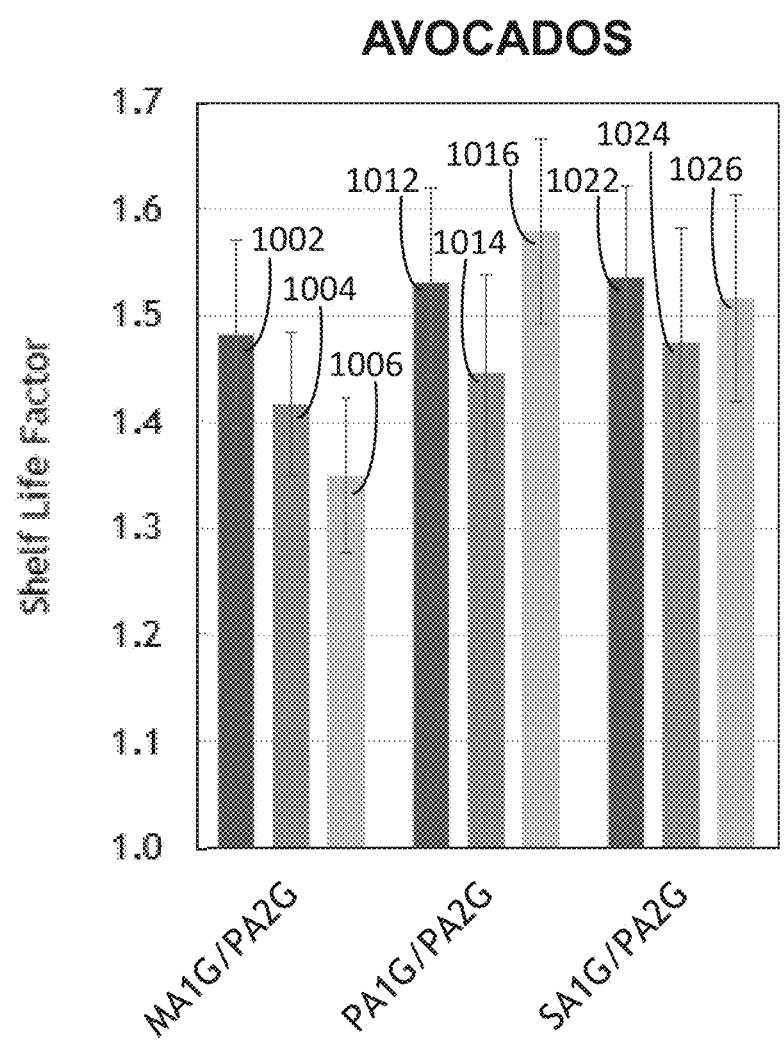
FIGS. 10, 11, and 12 are plots of the shelf life factor of groups of avocados that have each been treated with a solution including both a coating agent and a sanitizing agent.

FIG. 10 is a graph showing the shelf life factor for avocados that were each treated with a solution including a coating agent dissolved in ethanol (sanitizing agent). The coating agents included various mixtures of monoacylglyceride compounds, as detailed below. Each bar in the graph represents a group of 30 avocados and corresponds to a different coating agent composition. Bar 1002 corresponds to 25:75 mixture of 2,3-dihydroxypropan-2-yl tetradecanoate (MA1G) and 1,3-dihydroxypropan-2-yl hexadecanoate (PA2G), bar 1004 corresponds to 50:50 mixture of 2,3-dihydroxypropan-2-yl tetradecanoate and 1,3-dihydroxypropan-2-yl hexadecanoate, bar 1006 corresponds to 75:25 mixture of 2,3-dihydroxypropan-2-yl tetradecanoate and 1,3-dihydroxypropan-2-yl hexadecanoate, bar 1012 corresponds to 25:75 mixture of 2,3-dihydroxypropan-2-yl hexadecanoate (PA1G) and 1,3-dihydroxypropan-2-yl hexadecanoate (PA2G), bar 1014 corresponds to 50:50 mixture of 2,3-dihydroxypropan-2-yl hexadecanoate and 1,3-dihydroxypropan-2-yl hexadecanoate, bar 1016 corresponds to 75:25 mixture of 2,3-dihydroxypropan-2-yl hexadecanoate and 1,3-dihydroxypropan-2-yl hexadecanoate, bar 1022 corresponds to 25:75 mixture of 2,3-dihydroxypropan-2-yl octadecanoate (SA1G) and 1,3-dihydroxypropan-2-yl hexadecanoate (PA2G), bar 1024 corresponds to 50:50 mixture of 2,3-dihydroxypropan-2-yl octadecanoate and 1,3-dihydroxypropan-2-yl hexadecanoate, and bar 1026 corresponds to 75:25 mixture of 2,3-dihydroxypropan-2-yl octadecanoate and 1,3-dihydroxypropan-2-yl hexadecanoate. The coating agents were each dissolved in substantially pure ethanol (sanitizing agent) at a concentration of 5 mg/mL to form the solution, and the solution was applied to the surfaces of the avocados to sanitize the surfaces and to form coatings. As seen in FIG. 10, each of the treatments resulted in a shelf life factor of between 1.3 and 1.6 for the treated avocados, indicating a substantial increase in their shelf life as compared to untreated avocados.

As used herein, the term "shelf life factor" is defined as the ratio of the average mass loss rate of untreated produce (measured for a control group) to the average mass loss rate of the corresponding treated produce. Hence, a shelf life factor greater than 1 corresponds to a decrease in average mass loss rate of treated produce as compared to untreated produce, and a larger shelf life factor corresponds to a greater reduction in average mass loss rate.

Figure 11:
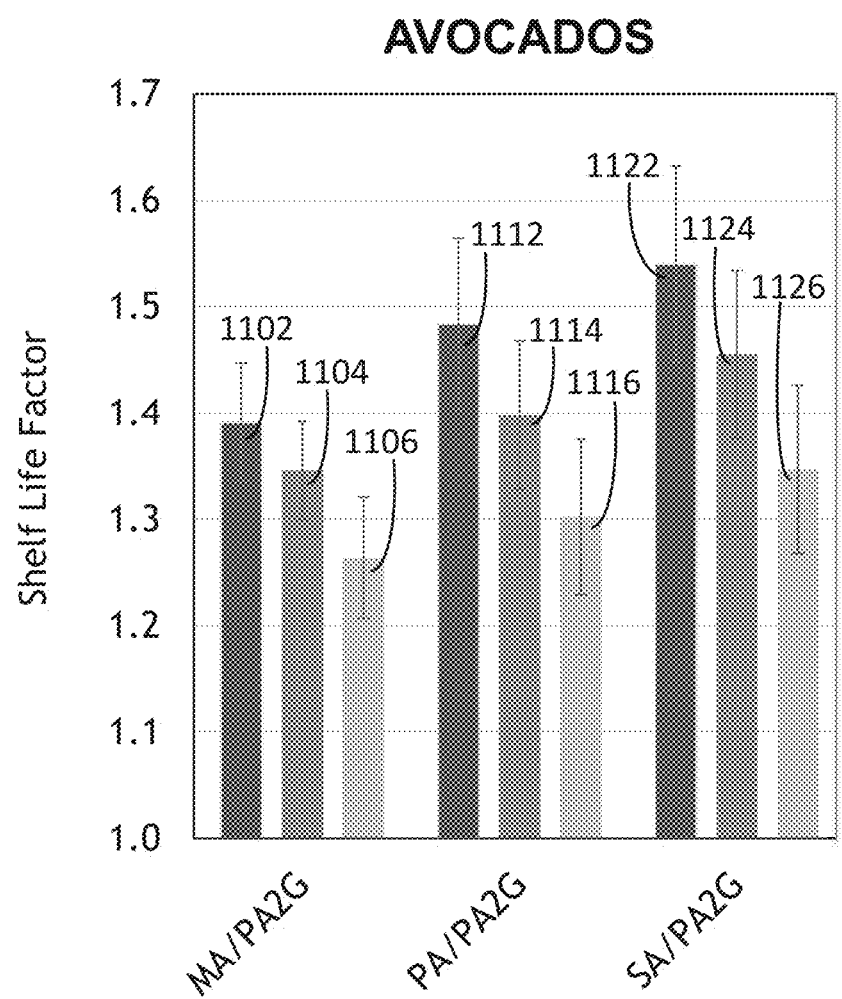

FIG. 11 is a graph showing the shelf life factor for avocados that were each treated with a solution including another coating agent dissolved in ethanol (sanitizing agent). Each bar in the graph represents a group of 30 avocados and corresponds to a different coating agent composition. Bar 1102 corresponds to 25:75 mixture of tetradecanoic acid (MA) and 1,3-dihydroxypropan-2-yl hexadecanoate (PA2G), bar 1104 corresponds to 50:50 mixture of tetradecanoic acid and 1,3-dihydroxypropan-2-yl hexadecanoate, bar 1106 corresponds to 75:25 mixture of tetradecanoic acid and 1,3-dihydroxypropan-2-yl hexadecanoate, bar 1112 corresponds to 25:75 mixture of hexadecanoic acid (PA) and 1,3-dihydroxypropan-2-yl hexadecanoate (PA2G), bar 1114 corresponds to 50:50 mixture of hexadecanoic acid and 1,3-dihydroxypropan-2-yl hexadecanoate, bar 1116 corresponds to 75:25 mixture of hexadecanoic acid and 1,3-dihydroxypropan-2-yl hexadecanoate, bar 1122 corresponds to 25:75 mixture of octadecanoic acid (SA) and 1,3-dihydroxypropan-2-yl hexadecanoate (PA2G), bar 1124 corresponds to 50:50 mixture of octadecanoic acid and 1,3-dihydroxypropan-2-yl hexadecanoate, and bar 1126 corresponds to 75:25 mixture of octadecanoic acid and 1,3-dihydroxypropan-2-yl hexadecanoate. The coating agents were each dissolved in substantially pure ethanol (sanitizing agent) at a concentration of 5 mg/mL to form the solution, and the solution was applied to the surfaces of the avocados to sanitize the surfaces and to form coatings. As seen in FIG. 11, each of the treatments resulted in a shelf life factor of between 1.25 and 1.55 for the treated avocados, indicating a substantial increase in their shelf life as compared to untreated avocados.

Figure 12:
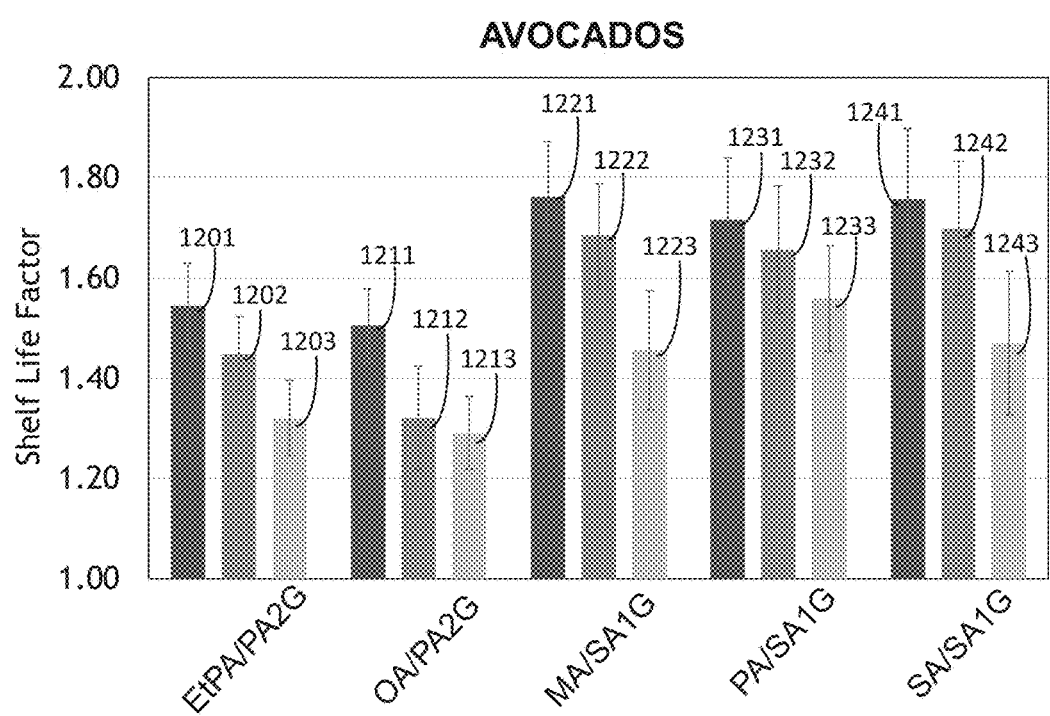

FIG. 12 is a graph showing the shelf life factor for avocados that were each treated with a solution including another coating agent dissolved in ethanol (sanitizing agent). Each of the bars represents a group of 30 avocados and corresponds to a different coating agent composition. Bars 1201-1203 correspond to coating agents which are mixtures of ethyl palmitate (EtPA) and 1,3-dihydroxypropan-2-yl hexadecanoate (PA2G) combined at a molar ratio of 25:75 (bar 1201), 50:50 (bar 1202), and 75:25 (bar 1203). Bars 1211-1213 correspond to coating agents which are mixtures of oleic acid (OA) and 1,3-dihydroxypropan-2-yl hexadecanoate (PA2G) combined at a molar ratio of 25:75 (bar 1211), 50:50 (bar 1212), and 75:25 (bar 1213). Bars 1221-1223 correspond to coating agents which are mixtures of tetradecanoic acid (MA) and 2,3-dihydroxypropan-2-yl octadecanoate (SA1G) combined at a molar ratio of 25:75 (bar 1221), 50:50 (bar 1222), and 75:25 (bar 1223). Bars 1231-1233 correspond to coating agents which are mixtures of hexadecanoic acid (PA) and 2,3-dihydroxypropan-2-yl octadecanoate (SA1G) combined at a molar ratio of 25:75 (bar 1231), 50:50 (bar 1232), and 75:25 (bar 1233). Bars 1241-1243 correspond to coating agents which are mixtures of octadecanoic acid (SA) and 2,3-dihydroxypropan-2-yl octadecanoate (SA1G) combined at a molar ratio of 25:75 (bar 1241), 50:50 (bar 1242), and 75:25 (bar 1243). The coating agents were each dissolved in substantially pure ethanol (sanitizing agent) at a concentration of 5 mg/mL to form the solution, and the solution was applied to the surfaces of the avocados to sanitize the surfaces and to form coatings. As seen in FIG. 12, each of the treatments resulted in a shelf life factor of between 1.25 and 1.8 for the treated avocados, indicating a substantial increase in their shelf life as compared to untreated avocados.

Figure 13A:
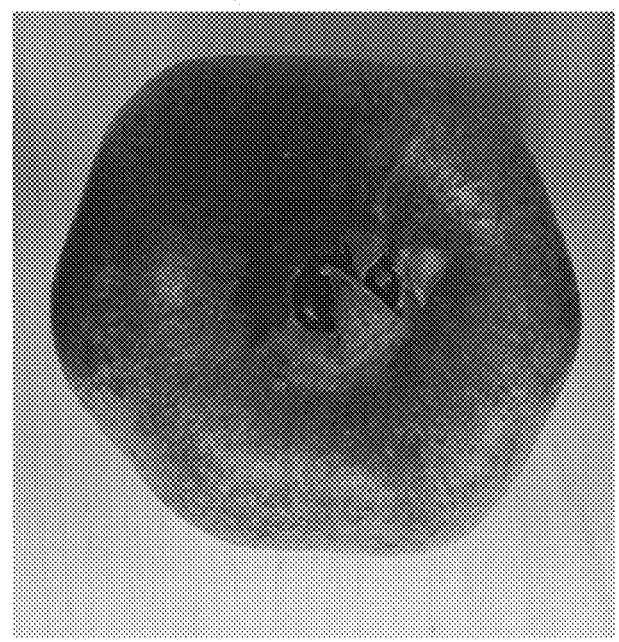
FIGS. 13A-13B are high resolution photographs of treated pomegranates.
Figure 13B:
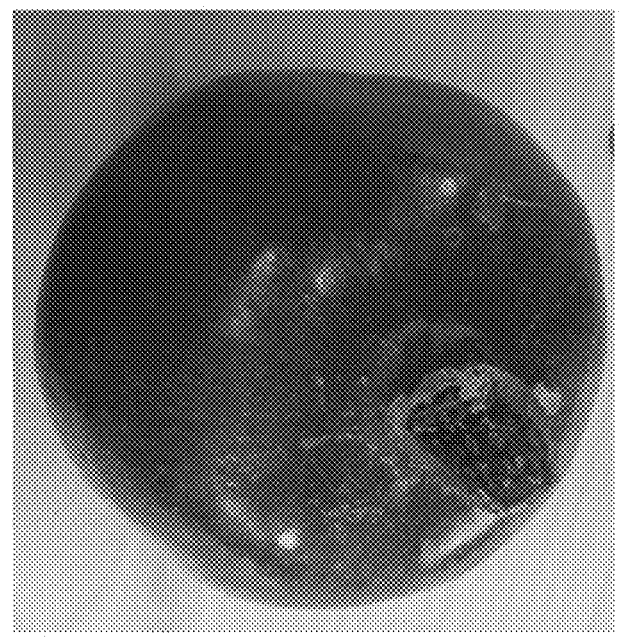

FIGS. 13A and 13B show high resolution photographs of pomegranates that were each treated with a solution including a coating agent dissolved in a solvent. The images are each representative of ten pomegranates that underwent the same treatment. In both cases, the coating agent was a 30:70 mixture of 2,3-dihydroxypropan-2-yl hexadecanoate and 1,3-dihydroxypropan-2-yl hexadecanoate and was dissolved in the solvent at a concentration of 40 mg/mL. For FIG. 13A, the solvent was pure ethanol (sanitizing agent), while for FIG. 13B, the solvent was 70% ethanol (sanitizing agent) and 30% water. For the pomegranates treated with the 100% ethanol solution (FIG. 13A), the solvent contacted the surfaces of the pomegranates for about 30-60 seconds before completely evaporating away, after which the coating agent remained on the surfaces. For the pomegranates treated with the 70% ethanol solution (FIG. 13B), the solvent contacted the surfaces of the pomegranates for about 10 minutes before completely evaporating away, after which the coating agent remained on the surfaces. Visible skin breakdown was observed in the pomegranates treated with the 100% ethanol solution (FIG. 13A), whereas the pomegranates treated with the 70% ethanol solution (FIG. 13B) appeared undamaged and were otherwise unaltered in appearance by the treatment.

Figure 14A:
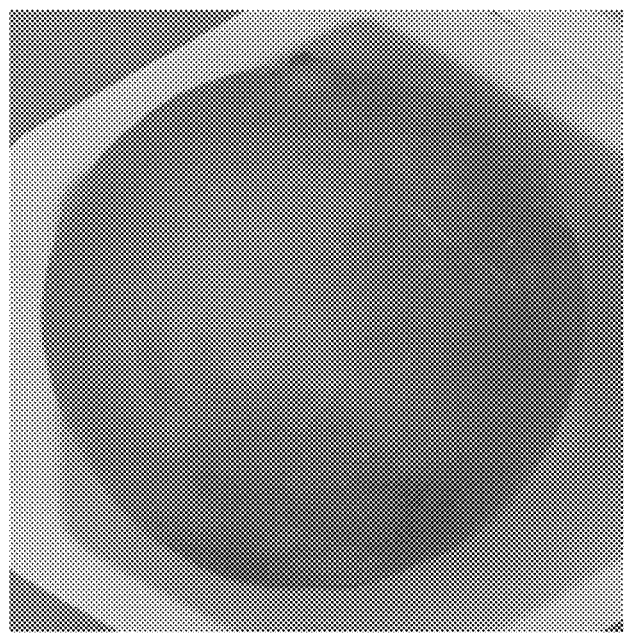
FIGS. 14A-14B are high resolution photographs of treated limes.
Figure 14B:
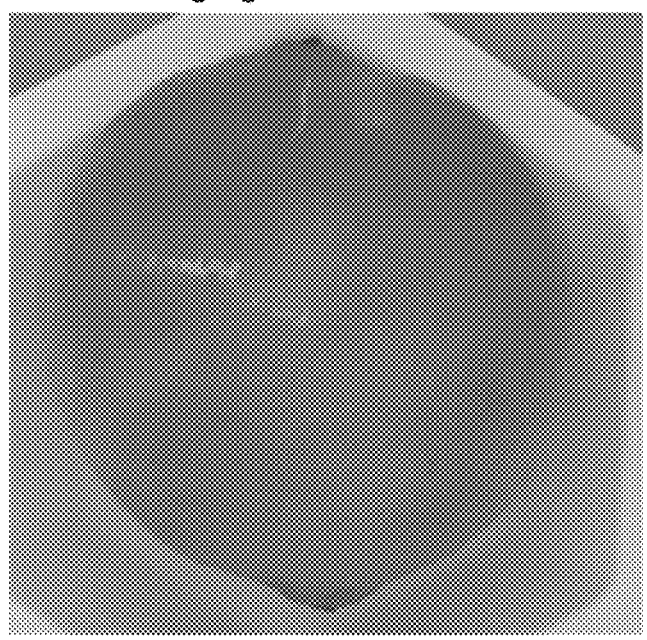

FIGS. 14A and 14B show high resolution photographs of limes that were each treated with a solution including a coating agent dissolved in a solvent. The images are each representative of six limes that underwent the same treatment. In both cases, the coating agent was a 30:70 mixture of 2,3-dihydroxypropan-2-yl hexadecanoate and 1,3-dihydroxypropan-2-yl hexadecanoate and was dissolved in the solvent at a concentration of 40 mg/mL. For FIG. 14A, the solvent was pure ethanol (sanitizing agent), while for FIG. 14B, the solvent was 80% ethanol (sanitizing agent) and 20% water. For the limes treated with the 100% ethanol solution (FIG. 14A), the solvent contacted the surfaces of the limes for about 30-60 seconds before completely evaporating away, after which the coating agent remained on the surfaces. For the limes treated with the 80% ethanol solution (FIG. 14B), the solvent contacted the surfaces of the limes for about 10 minutes before completely evaporating away, after which the coating agent remained on the surfaces. Visible skin breakdown was observed in the limes treated with the 100% ethanol solution (FIG. 14A), whereas the limes treated with the 80% ethanol solution (FIG. 14B) appeared undamaged and were otherwise unaltered in appearance by the treatment. Accordingly, without wishing to be bound by theory, as set forth in FIGS. 13A-13B and 14A-14B, treating produce with a solution which includes a coating agent dissolved in a solvent which includes a sanitizing agent can in some cases cause visible damage to the produce when the concentration of the sanitizing agent is too high (e.g., when the solvent is 100% ethanol), while not causing visible damage to the produce when the concentration of the sanitizing agent is lower (e.g., when the solvent is no more than 80% or 70% ethanol by volume).

Figure 15A:
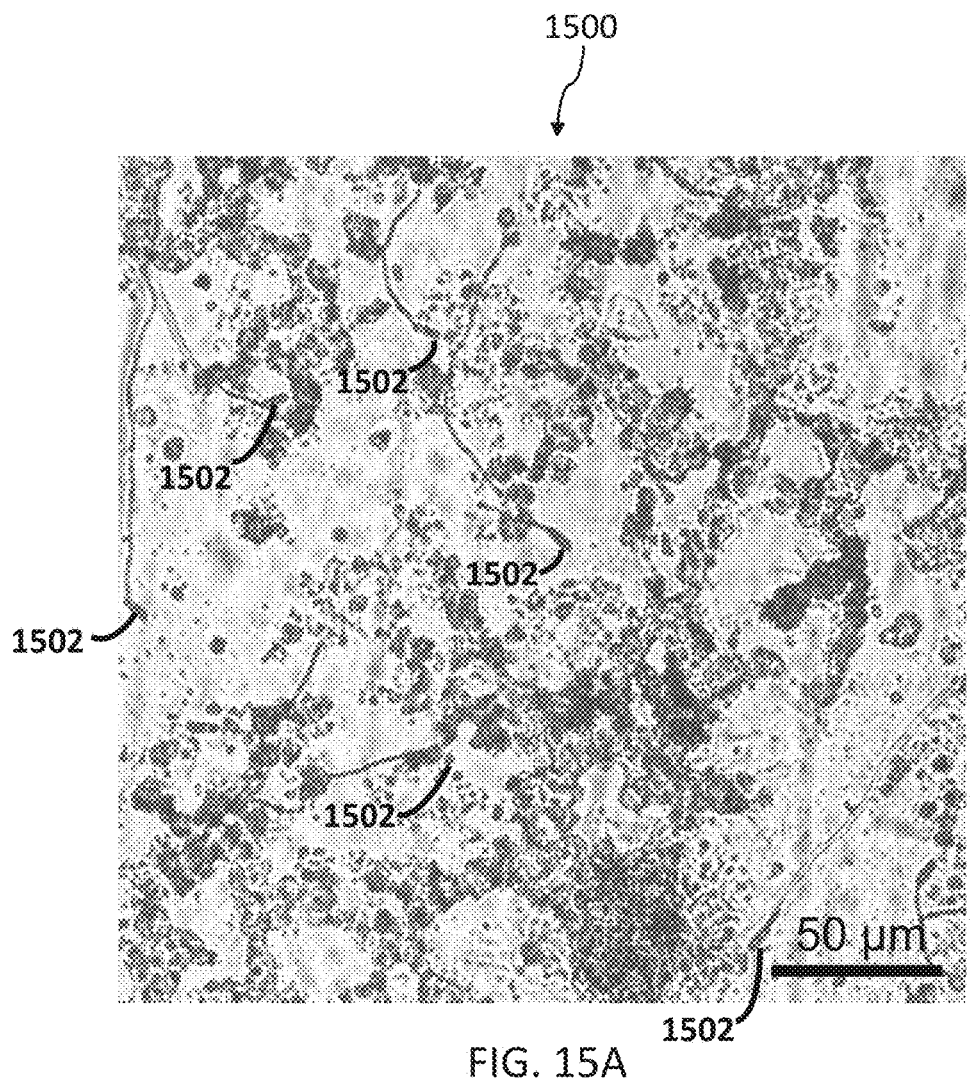
FIG. 15A shows a photo of *Colletotrichum* spores after incubation on a slide coated with a composition of the present disclosure.
Figure 15B:
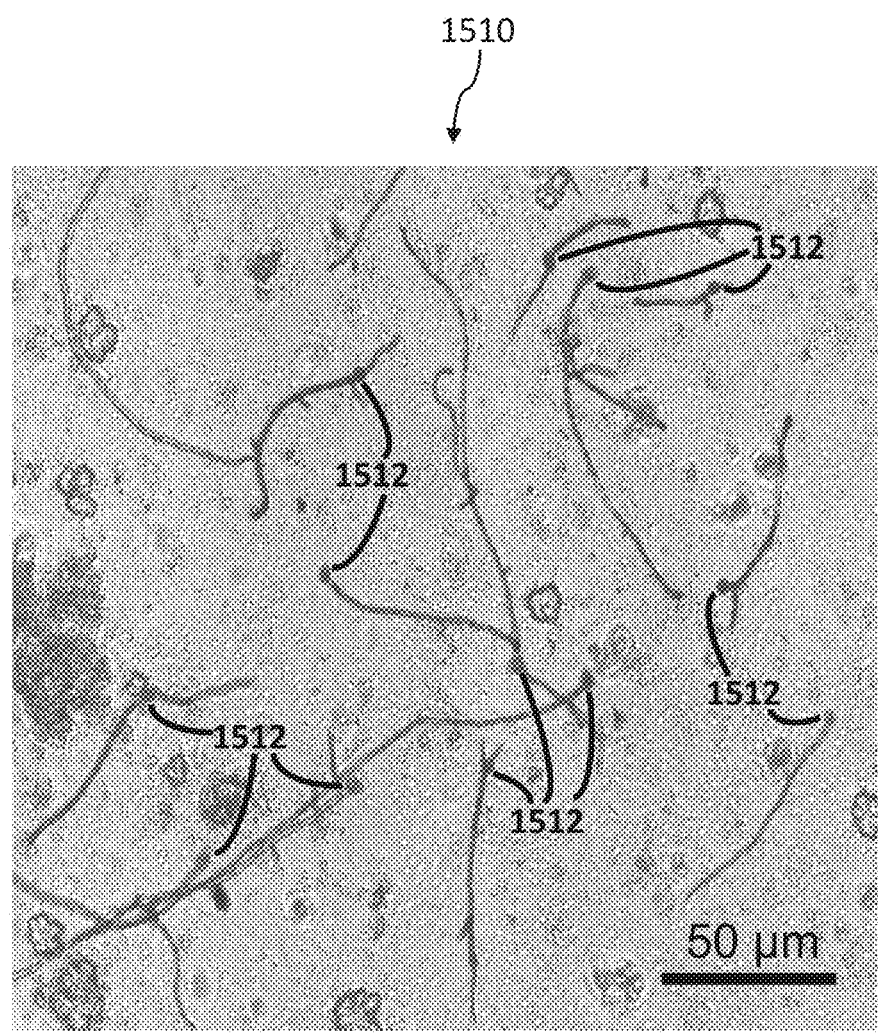
FIG. 15B shows a photo of *Botrytis* spores after incubation on a slide coated with a composition of the present disclosure.
Figure 16A:
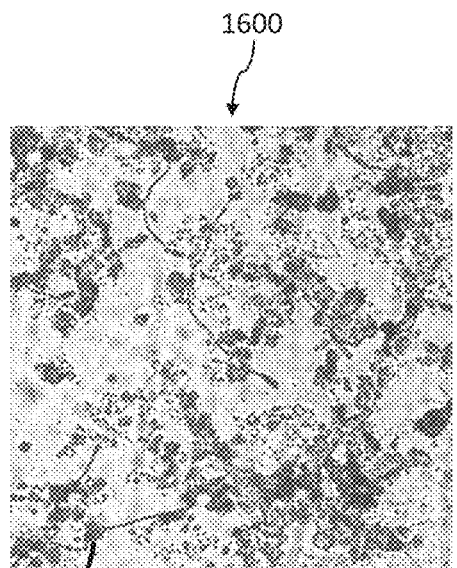
FIGS. 16A, 16B, 16C, 16D, 16E, 16F, and 16G show photos of *Colletotrichum* spores after incubation on slides coated with fruit wax and after treatment with various concentrations of ethanol and water.
Figure 16B:
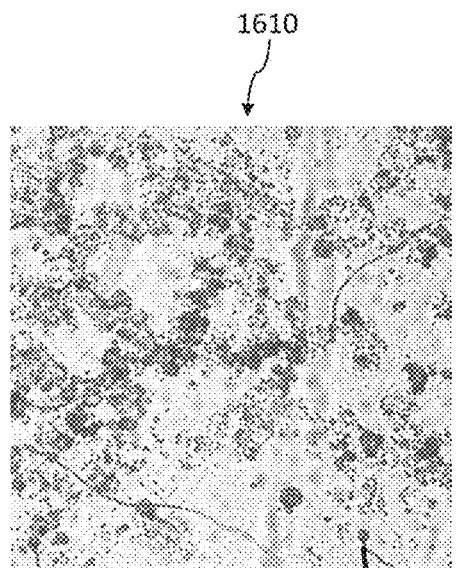
Figure 16C:
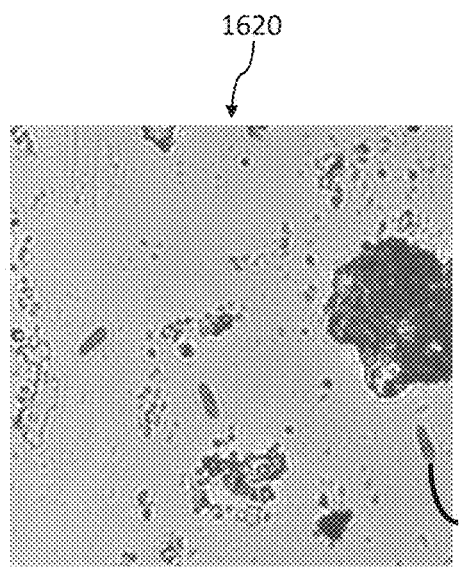
Figure 16D:
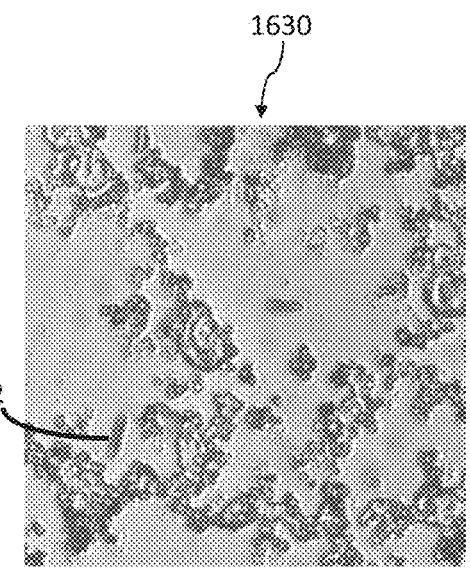
Figure 16E:
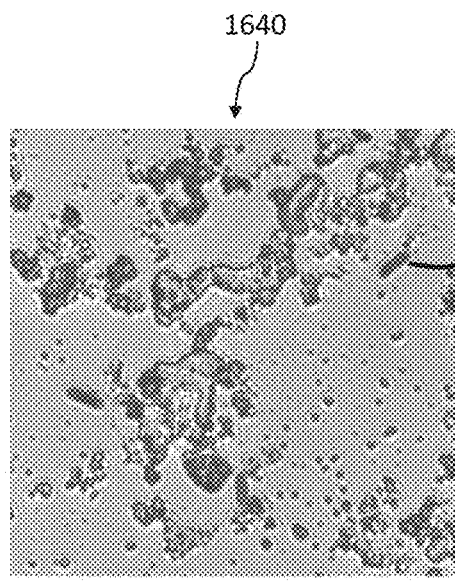
Figure 16F:
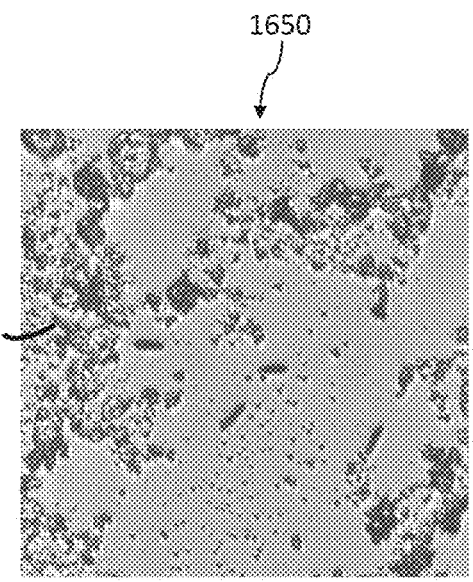
Figure 16G:
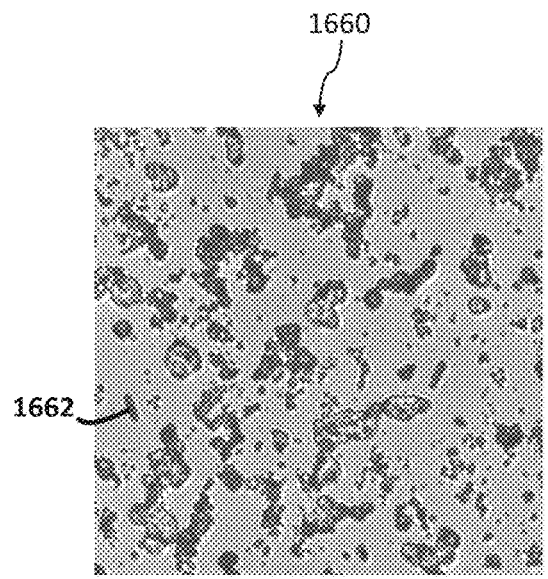
Figure 17A:
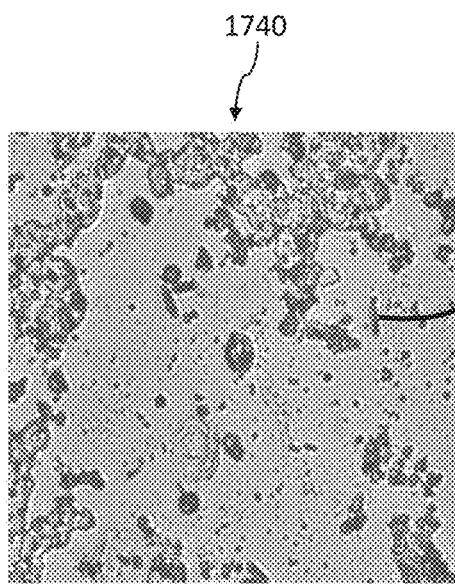
FIGS. 17A, 17B, and 17C show photos of *Colletotrichum* spores after incubation on slides coated with fruit wax and after treatment with various concentrations of ethanol and water in the presence of a coating composition of the present disclosure.
Figure 17B:
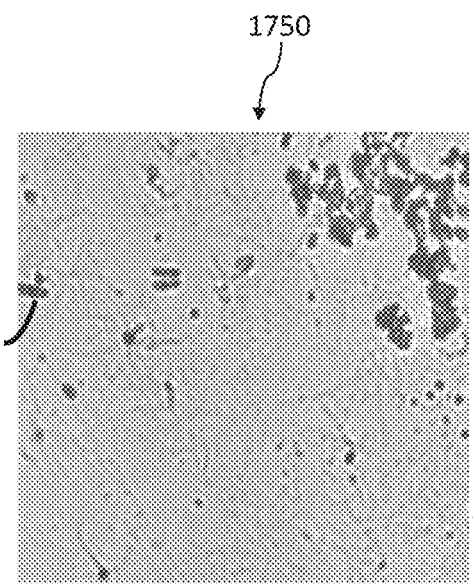
Figure 17C:
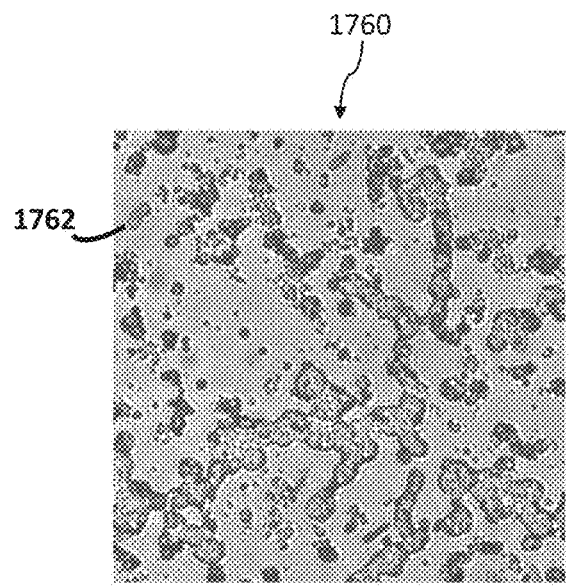
Figure 18A:
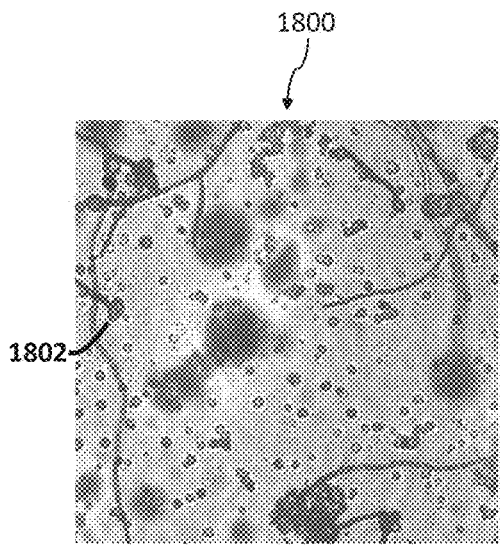
FIGS. 18A, 18B, 18C, 18D, 18E, 18F, and 18G show photos of *Botrytis* spores after incubation on slides coated with fruit wax and after treatment with various concentrations of ethanol and water.
Figure 18B:
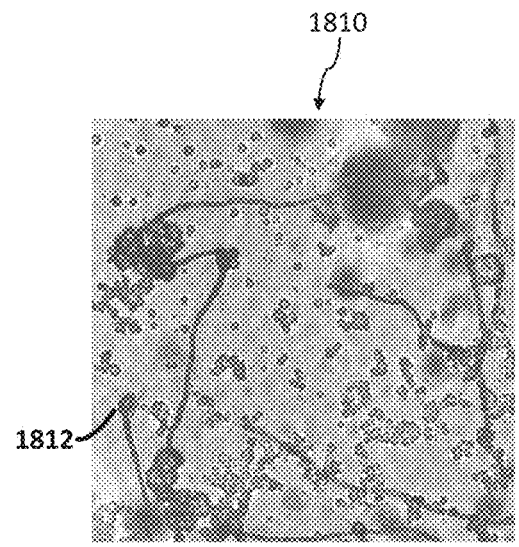
Figure 18C:
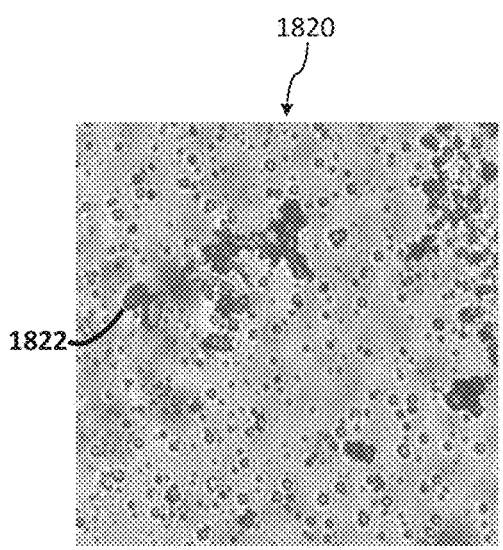
Figure 18D:
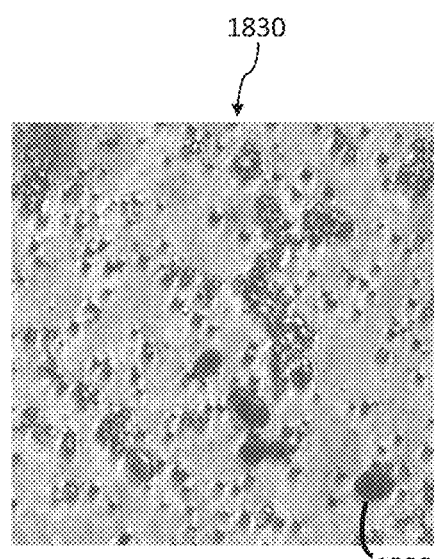
Figure 18E:
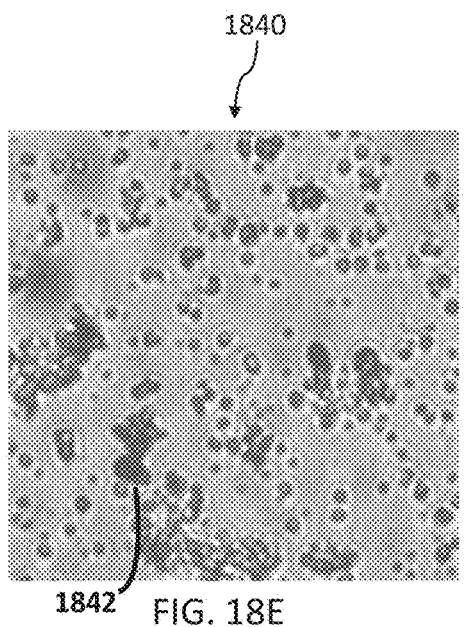
Figure 18F:
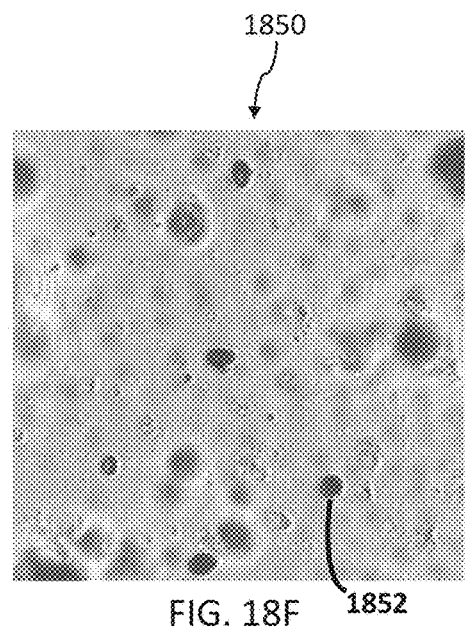
Figure 18G:
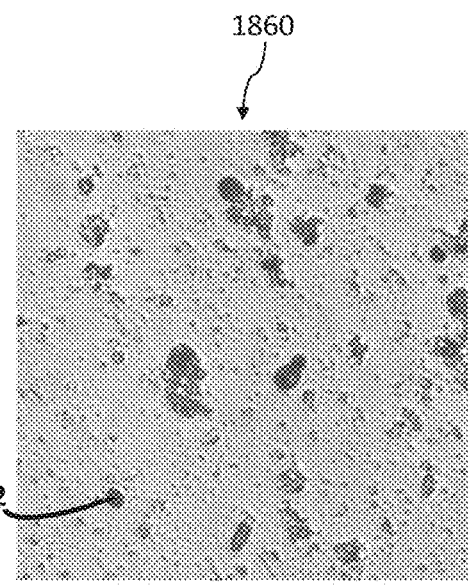
Figure 19A:
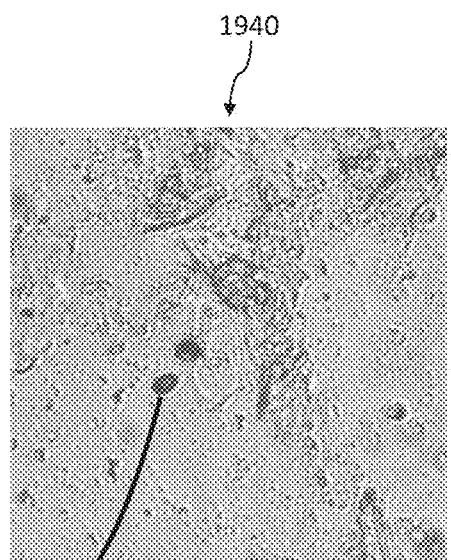
FIGS. 19A, 19B, and 19C show photos of *Botrytis* spores after incubation on slides coated with fruit wax and after treatment with various concentrations of ethanol and water in the presence of a coating composition of the present disclosure.
Figure 19B:
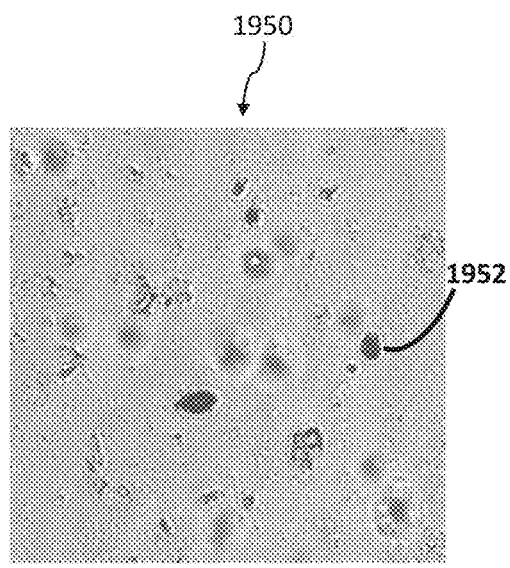
Figure 19C:
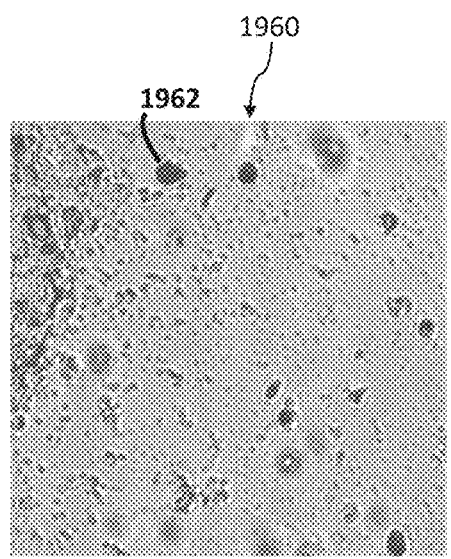

FIG. 15A and FIG. 15B show that fungal spores that are deposited onto certain coating compositions of the present disclosure (e.g., a 30:70 mixture of palmitic acid 1-glycerol and palmitic acid 2-glycerol) are able to survive and germinate. Accordingly, without wishing to be bound by theory, it is understood that at least some of the coating compositions of the present disclosure (for instance, in the absence of a sanitizing agent) do not independently prevent or suppress fungal growth or sanitize the surface onto which they are applied. As such, at least some of the coating agents of the present disclosure are non-sanitizing coating agents.

FIGS. 16A-16G, 17A-17C, 18A-18G, and 19A-19C show optical microscope images of glass slides coated with fruit wax and treated with *Colletotrichum* (16A-16G and 17A-17C) and *Botrytis* (18A-18G and 19A-19C) spores. As set forth in FIGS. 16A-16G and 18A-18G, and described in more details in the Examples below, spores were found to germinate even after treatment with ethanol compositions below 30% ethanol. However, treatment with ethanol concentrations at 30% and above was found to inhibit the germination of fungal spores. As set forth in FIGS. 17A-17C and 19A-19C, higher ethanol concentrations were still found to inhibit the germination of fungal spores when a coating agent of the present disclosure (e.g., a 30:70 mixture of palmitic acid 1-glycerol and palmitic acid 2-glycerol) was dissolved in the ethanol (or ethanol/water mixture) and left on the surface of the coated glass slides. Accordingly, without wishing to be bound by theory, use of a sanitizing agent (e.g., ethanol) as part of the solvent can help sanitize and reduce fungal growth when applied to an edible substrate (e.g., produce). Furthermore, without wishing to be bound by theory, ethanol solutions at or about 30% or greater ethanol concentration can sanitize the surface of produce and prevent microbial (e.g., fungal) growth. Moreover, without wishing to be bound by theory, when coating compositions of the present disclosure are included in an ethanol/water mixture of 30% or greater ethanol composition, microbial (e.g., fungal) growth is prevented.

FIGS. 20A-20D and 21A-21B show optical microscope images of glass slides coated with fruit wax and treated with *Penicillium* spores. FIG. 22 is a table showing percent germination of *Penicillium* spores for each of the conditions corresponding to FIGS. 20A-20D and 21A-21B. Spores were found to germinate even after treatment with ethanol compositions of 30% or less. However, treatment with higher ethanol concentrations (e.g., 70% ethanol or 100% ethanol) was found to inhibit the germination of fungal spores. As set forth in FIG. 22, higher ethanol concentrations were still found to inhibit the germination of *Penicillium* spores when a coating agent of the present disclosure (e.g., a 30:70 mixture of stearic acid 1-glycerol and palmitic acid 2-glycerol) was dissolved in the ethanol (or ethanol/water mixture) and left on the surface of the coated glass slides. Furthermore, solvent contact times from 5 seconds to 10 minutes all yielded the same results for each of the solutions apart from the 30% ethanol solution, for which a 5 second contact time yielded slightly higher rates of germination than longer contact times.

A method for treating agricultural products so that they are sanitized and preserved, and can, for example, be provided as Ready-to-Eat is now described. The treatment results in the agricultural products being sufficiently sanitized, while also decreasing the mass loss rate and extending the shelf life of the produce in comparison to harvested produce that has not been treated. First, a solution is formed by dissolving a coating agent which includes a composition of monomers, oligomers, fatty acids, esters, amides, amines, thiols, carboxylic acids, ethers, aliphatic waxes, alcohols, salts (inorganic and organic), or combinations thereof (coating components) in a solvent, the solvent including a sanitizing agent (e.g., ethanol, methanol, acetone, isopropanol, ethyl acetate, or combinations thereof). Specific examples of compositions of the coating agent were described above and are described in further detail below. The solution is then applied to the surface of the agricultural product for a time sufficient for the sanitizing to sanitize the surface such that the product is safe for consumption without further washing. During the time that the solution is applied to the agricultural product, the coating components form a protective coating over the surface. In some embodiments, the protective coating prevents the sanitizing agent from damaging the agricultural product. In other embodiments, the protective coating replaces and/or reinforces portions of the natural coating covering the produce (e.g., the cuticular layer) which are damaged by the sanitizing agent, thereby mitigating or eliminating the deleterious effects the sanitizing agent has on the surface. The composition of the coating components can be formulated such that the coating is edible and optionally substantially undetectable. The solvent is then removed from the surface of the agricultural product, leaving the protective coating on the surface. The coating, which remains on the surface of the agricultural product, serves as a barrier to biotic and/or abiotic stressors such as moisture loss, oxidation, and fungal growth, thereby maintaining freshness and extending the shelf life of the agricultural product even beyond that which is observed for similar products that have not undergone washing, sanitization, or any other post-harvest treatment. The method provides the advantage of treating the product using a single process step that both sanitizes the product and also causes an extension in the shelf life of the product.

As previously described, the sanitizing agent can be any solvent which is capable of sanitizing the surface of the produce. Examples include ethyl acetate, acetone, and alcohols such as ethanol, methanol, or, isopropanol, or combinations of any of the above. Historically, alcohols have been some of the most commonly used substances for sanitizing and disinfecting, and for example are used for disinfecting skin prior to hypodermic injections and finger pricks. Although the solvent can be formed entirely from the sanitizing agent, in many cases this has been found to lead to surface damage in produce even when a protective layer is formed. Diluting the sanitizing agent with water, such that the solvent is about 90% sanitizing agent by volume or less, about 80% sanitizing agent by volume or less, or about 70% sanitizing agent by volume or less has been found to substantially reduce surface damage for a variety of produce (for example, see FIGS. 13A-13B and 14A-14B). Furthermore, in some applications, many sanitizing agents have been found to more effectively sanitize surfaces when diluted with water. For example, ethanol and water mixtures which are in the range of about 50% to 80% ethanol have in some applications been found to be more effective sanitizers than pure ethanol. Too weak of a dilution of the sanitizing agent (e.g., such that the sanitizing agent to water ratio is less than about 30/70, less than about 40/60, or less than about 50/50) can prevent the sanitizing agent from sufficiently sanitizing the surface of the agricultural product. Accordingly, in some embodiments, the solvent includes water and the sanitizing agent (e.g., ethanol) and is between 40% and 95% sanitizing agent by volume, for example between 40% and 90%, between 40% and 80%, between 45% and 95%, between 45% and 90%, between 45% and 80%, between 50% and 95%, between 50% and 90%, between 50% and 80%, between 60% and 95%, between 60% and 90%, or between 60% and 80% sanitizing agent by volume. In particular embodiments, the sanitizing agent comprises ethanol, and the solvent includes ethanol and water and is between 40% and 95% ethanol by volume, for example between 50% and 90%, between 50% and 80%, or between 60% and 80% ethanol by volume. In some embodiments, the volume ratio of the sanitizing agent to water in the solution is in a range of about 1 to 10.

The use of ethanol as a sanitizing or disinfecting agent has been widely reported. For example, Morton reported on the bactericidal activity of various concentrations of ethyl alcohol (ethanol) examined against a variety of microorganisms in exposure periods ranging from 10 seconds to 1 hour. *Pseudomonas aeruginosa* was killed in 10 seconds by all concentrations of ethanol from 30% to 100% (v/v), and *Serratia marcescens, E. coli* and *Salmonella typhosa* were killed in 10 seconds by all concentrations of ethanol from 40% to 100%. The gram-positive organisms *Staphylococcus aureus* and *Streptococcus pyogenes* were slightly more resistant, being killed in 10 seconds by ethyl alcohol concentrations of 60%-95% (Morton, *Annals New York Academy of Sciences,* 53(1), 1950, pp. 191-196). Karabulut et al studied the effects of postharvest ethanol treatments of table grapes for controlling gray mold and found that ethanol concentrations of 30% or more applied for 10 at least seconds inhibit the germination of *Botrytis* (Karabulut et al., *Postharvest Biology and Technology,* 43 (2004) pp. 169-177). Oh et al studied the antimicrobial activity of ethanol against *Listeria monocytogenes* and found that 5% ethanol concentrations inhibit (but do not completely stop) growth of *Listeria monocytogenes* (Oh and Marshall, *International Journal of Food Microbiology,* 20 (1993) pp. 239-246).

As described above, the bacterial levels on the agricultural product following the sanitization process depend at least partially on the specific composition of the solvent and the duration of time that the solution is applied to the product before the solvent is removed. A minimum application time may be required in order to adequately sanitize the products. Furthermore, a specific application time may also be required in order to form a coating which adequately protects the agricultural product from damage and extends the shelf life of the product. It has been found that methods described herein for treating products can effectively form coatings for application times in the range of about 5 seconds to 30 minutes, where shorter application times are achieved by actively removing the solvent (e.g., by blowing air on the treated products), while longer application times result when the solvent is allowed to evaporate without any other form of active removal. In some cases, for example in large-scale treatment facilities, shorter application times may be preferable in order to increase the throughput of the treated products.

Accordingly, in view of the above, the solution can be applied to the surface of the agricultural product for between 1 and 3,600 seconds, for example between 1 and 3000 seconds, between 1 and 2000 seconds, between 1 and 1000 seconds, between 1 and 800 seconds, between 1 and 600 seconds, between 1 and 500 seconds, between 1 and 400 seconds, between 1 and 300 seconds, between 1 and 250 seconds, between 1 and 200 seconds, between 1 and 150 seconds, between 1 and 125 seconds, between 1 and 100 seconds, between 1 and 80 seconds, between 1 and 60 seconds, between 1 and 50 seconds, between 1 and 40 seconds, between 1 and 30 seconds, between 1 and 20 seconds, between 1 and 10 seconds, between 5 and 3000 seconds, between 5 and 2000 seconds, between 5 and 1000 seconds, between 5 and 800 seconds, between 5 and 600 seconds, between 5 and 500 seconds, between 5 and 400 seconds, between 5 and 300 seconds, between 5 and 250 seconds, between 5 and 200 seconds, between 5 and 150 seconds, between 5 and 125 seconds, between 5 and 100 seconds, between 5 and 80 seconds, between 5 and 60 seconds, between 5 and 50 seconds, between 5 and 40 seconds, between 5 and 30 seconds, between 5 and 20 seconds, between 5 and 10 seconds, between 10 and 3000 seconds, between 10 and 2000 seconds, between 10 and 1000 seconds, between 10 and 800 seconds, between 10 and 600 seconds, between 10 and 500 seconds, between 10 and 400 seconds, between 10 and 300 seconds, between 10 and 250 seconds, between 10 and 200 seconds, between 10 and 150 seconds, between 10 and 125 seconds, between 10 and 100 seconds, between 10 and 80 seconds, between 10 and 60 seconds, between 10 and 50 seconds, between 10 and 40 seconds, between 10 and 30 seconds, between 10 and 20 seconds, between 20 and 100 seconds, between 100 and 3,000 seconds or between 500 and 2,000 seconds. In some implementations, the sanitization process results in substantially reduced or substantially negligible bacteria, viral, and/or fungal levels on the surface of the agricultural product.

The protective coating formed from the coating agent can serve to prevent damage to the edible product (e.g., produce) caused by the sanitizing agent. The protective coating can increase the shelf life of the product. The protective coating formed from the coating agent can replace or reinforce portions of the produce which are damaged by the sanitizing agent. The coating can form an edible coating over the produce. In some embodiments, the product is a thin skin fruit or vegetable. For instance, the product can be a berry, grape, or apple. In some embodiments, the product can include a cut fruit surface (e.g., sliced apple). In some embodiments, the product includes a thick-skinned fruit, optionally for which the skin has been removed to expose a surface of the underlying fruit, and optionally the fruit has been cut (e.g., avocado slices).

The specific composition of the coating agent can be formulated such that the resulting coating formed over the agricultural product mimics or enhances the cuticular layer of the product. The biopolyester cutin forms the main structural component of the cuticle that composes the aerial surface of most land plants. Cutin is formed from a mixture of polymerized mono- and/or polyhydroxy fatty acids and embedded cuticular waxes. The hydroxy fatty acids of the cuticle layer form tightly bound networks with high cross-link density, thereby acting as a barrier to moisture loss and oxidation, as well as providing protection against other environmental stressors.

The coating components (e.g., monomers, oligomers, fatty acids, esters, amides, amines, thiols, carboxylic acids, ethers, aliphatic waxes, alcohols, salts (inorganic and organic), or combinations thereof) which are dissolved in the solvent can be extracted or derived from plant matter, and in particular from cutin obtained from plant matter. Plant matter typically includes some portions that contain cutin and/or have a high density of cutin (e.g., fruit peels, leaves, shoots, etc.), as well as other portions that do not contain cutin or have a low density of cutin (e.g., fruit flesh, seeds, etc.). The cutin-containing portions can be formed from the monomer and/or oligomer units which are subsequently utilized in the formulations described herein for preparation of RTE agricultural products. The cutin-containing portions can also include other constituents such as proteins, polysaccharides, phenols, lignans, aromatic acids, terpenoids, flavonoids, carotenoids, alkaloids, alcohols, alkanes, and aldehydes, which may be included in the coating agent or may be omitted.

The coating components (e.g., monomers, oligomers, fatty acids, esters, amides, amines, thiols, carboxylic acids, ethers, aliphatic waxes, alcohols, salts (inorganic and organic), or combinations thereof) can be obtained by first separating (or at least partially separating) portions of the plant that include molecules desirable for formulations for forming protective barriers (e.g., RTE formulations) from those that do not include the desired molecules. For example, when utilizing cutin as the feed stock for the solute composition, the cutin-containing portions of the plant matter are separated (or at least partially separated) from non-cutin-containing portions, and cutin is obtained from the cutin-containing portions (e.g., when the cutin-containing portion is a fruit peel, the cutin is separated from the peel). The obtained portion of the plant (e.g., cutin) is then depolymerized (or at least partially depolymerized) in order to obtain a mixture including a plurality of fatty acid or esterified cutin monomers, oligomers, or combinations thereof. The cutin derived monomers, oligomers, esters, or combinations thereof can be directly dissolved in the solvent to form the formulation used in the preparation of the agricultural products (e.g., RTE products), or alternatively can first be activated or chemically modified (e.g., functionalized). Chemical modification or activation can, for example, include glycerating the monomers, oligomers, or combinations thereof to form a mixture of 1-monoacylglycerides and/or 2-monoacylglycerides, and the mixture of 1-monoacylglycerides and/or 2-monoacylglycerides is dissolved in the solvent to form a solution, thereby resulting in the formulation for preparation of the agricultural products (e.g., RTE products).

In some implementations, the solute (e.g., the coating agent) of the formulation for preparation of agricultural products comprises fatty acids, esters, amides, amines, thiols, carboxylic acids, ethers, aliphatic waxes, alcohols, salts (inorganic and organic), or combinations thereof. In some implementations, the solute comprises monoacylglyceride (e.g., 1-monoacylglyceride or 2-monoacylglyceride) esters of monomers and/or oligomers.

In some implementations, the solute (e.g., the coating agent) includes compounds of Formula I:

(Formula I)

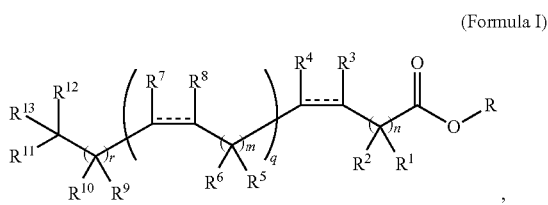

wherein:

R is selected from —H, —$C_1$-$C_6$ alkyl, —$C_2$-$C_6$ alkenyl, —$C_2$-$C_6$ alkynyl, —$C_3$-$C_7$ cycloalkyl, aryl, or heteroaryl, wherein each alkyl, alkenyl, alkynyl, cycloalkyl, aryl or heteroaryl is optionally substituted with one or more $C_1$-$C_6$ alkyl or hydroxy;

$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, —$SR^{14}$, halogen, —$C_1$-$C_6$ alkyl, —$C_2$-$C_6$ alkenyl, —$C_2$-$C_6$ alkynyl, —$C_3$-$C_7$ cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, $SR^{14}$, or halogen;

$R^3$, $R^4$, $R^7$ and $R^8$ are each independently, at each occurrence, —H, —$OR^{14}$, —$NR^{14}R^{15}$, —$SR^{14}$, halogen, —$C_1$-$C_6$ alkyl, —$C_2$-$C_6$ alkenyl, —$C_2$-$C_6$ alkynyl, —$C_3$-$C_7$ cycloalkyl, aryl, or heteroaryl, wherein each alkyl, alkenyl, alkynyl, cycloalkyl, aryl, or heteroaryl is optionally substituted with —$OR^{14}$, —$NR^{14}R^{15}$, —$SR^{14}$, or halogen; or $R^3$ and $R^4$ can combine with the carbon atoms to which they are attached to form a $C_3$-$C_6$ cycloalkyl, a $C_4$-$C_6$ cycloalkenyl, or 3- to 6-membered ring heterocycle; and/or $R^7$ and $R^8$ can combine with the carbon atoms to which they are attached to form a $C_3$-$C_6$ cycloalkyl, a $C_4$-$C_6$ cycloalkenyl, or 3- to 6-membered ring;

$R^{14}$ and $R^{15}$ are each independently, at each occurrence, —H, —$C_1$-$C_6$ alkyl, -$C_2$-$C_6$ alkenyl, or —$C_2$-$C_6$ alkynyl;

the symbol ====== represents an optionally single or cis or trans double bond;

n is 0, 1, 2, 3, 4, 5, 6, 7, or 8;

m is 0, 1, 2, or 3;

q is 0, 1, 2, 3, 4, or 5; and r is 0, 1, 2, 3, 4, 5, 6, 7, or 8.

In some embodiments, R is —H, —$CH_3$, or —$CH_2CH_3$.

In some embodiments, the coating agent comprises monoacylglycerides (e.g., 1-monoacylglycerides or 2-monoacylglycerides). The difference between a 1-monoacylglyceride and a 2-monoacylglyceride is the point of connection of the glycerol ester. Accordingly, in some embodiments, the coating agent comprises compounds of the Formula I-A (e.g., 2-monoacylglycerides):

(Formula I-A)

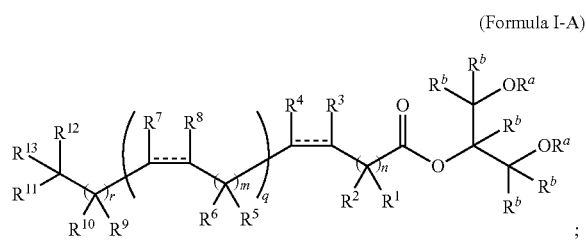

wherein:

each $R^a$ is independently —H or —$C_1$-$C_6$ alkyl;

each $R^b$ is independently selected from —H, —$C_1$-$C_6$ alkyl, or —OH;

$R^1$, $R^2$, $R^5$, $R^6$, $R^9$, $R^{10}$, $R^{11}$, $R^{12}$ and $R^{13}$ are each independently, at each occurrence, —H, —$OR^{13}$, —$NR^{14}R^{15}$, —$SR^{14}$, halogen, —$C_1$-$C_6$ alkyl, —$C_2$-$C_6$ alkenyl, —$C_2$-$C_6$ alkynyl, —$C_3$-$C_7$ cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen;

$R^3$, $R^4$, $R^7$, and $R^8$ are each independently, at each occurrence, —H, —$OR^{14}$, —$NR^{14}R^{15}$, —$SR^{14}$, halogen, —$C_1$-$C_6$ alkyl, —$C_2$-$C_6$ alkenyl, —$C_2$-$C_6$ alkynyl, -$C_3$-$C_7$ cycloalkyl, aryl, or heteroaryl wherein each alkyl, alkynyl, cycloalkyl, aryl, or heteroaryl is optionally substituted with one or more —$OR^{14}$, —$NR^{14}R^{15}$, —$SR^{14}$, or halogen; or $R^3$ and $R^4$ can combine with the carbon atoms to which they are attached to form a $C_3$-$C_6$ cycloalkyl, a $C_4$-$C_6$ cycloalkenyl, or 3- to 6-membered ring heterocycle; and/or $R^7$ and $R^8$ can combine with the carbon atoms to which they are attached to form a $C_3$-$C_6$ cycloalkyl, a $C_4$-$C_6$ cycloalkenyl, or 3- to 6-membered ring heterocycle;

$R^{14}$ and $R^{15}$ are each independently, at each occurrence, —H, —$C_1$-$C_6$ alkyl, —$C_2$-$C_6$ alkenyl, or —$C_2$-$C_6$ alkynyl;

the symbol ====== represents a single bond or a cis or trans double bond;

n is 0, 1, 2, 3, 4, 5, 6, 7 or 8;

m is 0, 1, 2 or 3;

q is 0, 1, 2, 3, 4 or 5; and r is 0, 1, 2, 3, 4, 5, 6, 7 or 8.

In some embodiments, the coating agent comprises compounds of the Formula I-B (e.g., 1-monoacylglycerides):

(Formula I-B)

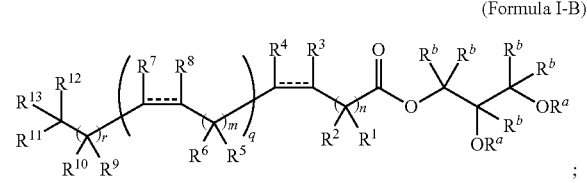

wherein:

each $R^a$ is independently —H or —$C_1$-$C_6$ alkyl; each $R^b$ is independently selected from —H, —$C_1$-$C_6$ alkyl, or —OH;

$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, -$SR^{14}$, halogen, —$C_1$-$C_6$ alkyl, —$C_2$-$C_6$ alkenyl, —$C_2$-$C_6$ alkynyl, —$C_3$-$C_7$ cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, $SR^{14}$, or halogen;

$R^3$, $R^4$, $R^7$, and $R^8$ are each independently, at each occurrence, —H, —$OR"$, —$NR^{14}R^{15}$, —$SR^{14}$, halogen, —$C_1$-$C_6$ alkyl, —$C_2$-$C_6$ alkenyl, —$C_2$-$C_6$ alkynyl, —$C_3$-$C_7$ cycloalkyl, aryl, or heteroaryl wherein each alkyl, alkynyl, cycloalkyl, aryl, or heteroaryl is optionally substituted with one or more —$OR^{14}$, —$NR^{14}R^{15}$, $SR^{14}$, or halogen; or $R^3$ and $R^4$ can combine with the carbon atoms to which they are attached to form a $C_3$-$C_6$ cycloalkyl, a $C_4$-$C_6$ cycloalkenyl, or 3- to 6-membered ring heterocycle; and/or $R^7$ and $R^8$ can combine with the carbon atoms to which they are attached to form a $C_3$-$C_6$ cycloalkyl, a $C_4$-$C_6$ cycloalkenyl, or 3- to 6-membered ring heterocycle;

$R^{14}$ and $R^{15}$ are each independently, at each occurrence, —H, —$C_1$-$C_6$ alkyl, —$C_2$-$C_6$ alkenyl, or —$C_2$-$C_6$ alkynyl;

the symbol  represents a single bond or a cis or trans double bond;
n is 0, 1, 2, 3, 4, 5, 6, 7 or 8;
m is 0, 1, 2 or 3;
q is 0, 1, 2, 3, 4 or 5; and
r is 0, 1, 2, 3, 4, 5, 6, 7 or 8.
In some embodiments, the coating agent includes one or more of the following fatty acid compounds:
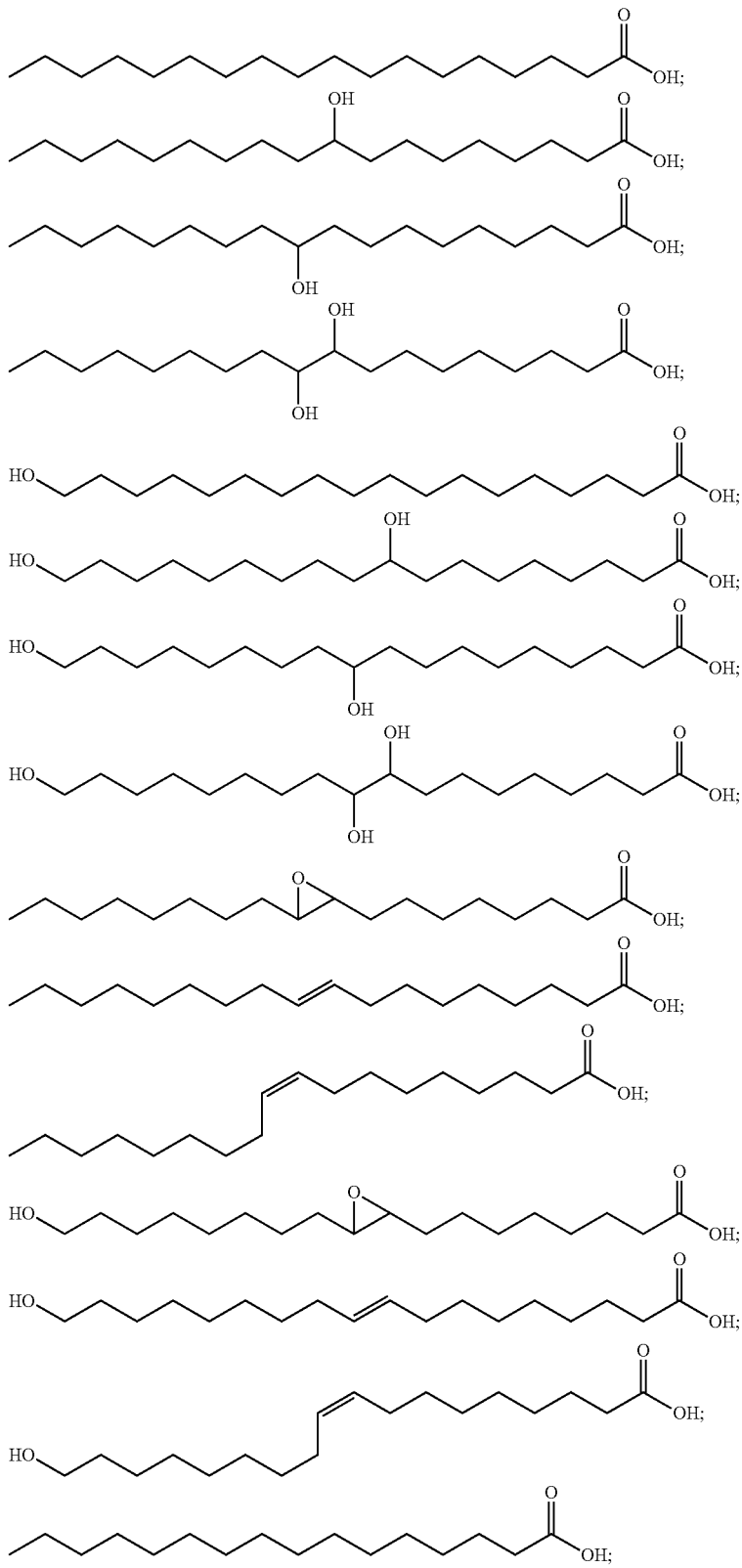

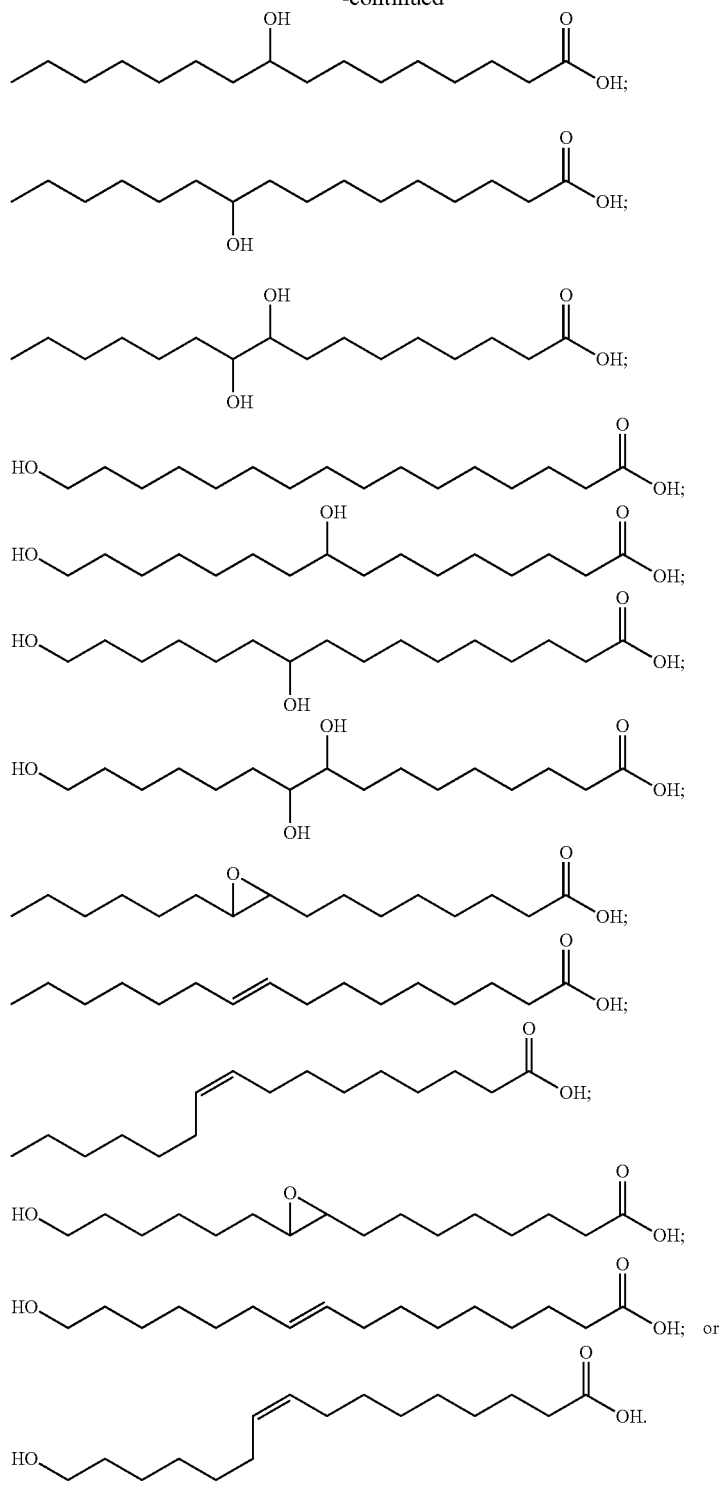
In some embodiments, the coating agent includes one or more of the following methyl ester compounds:
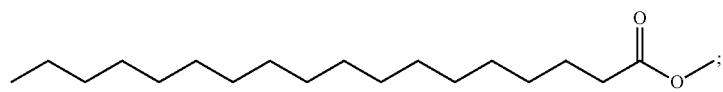

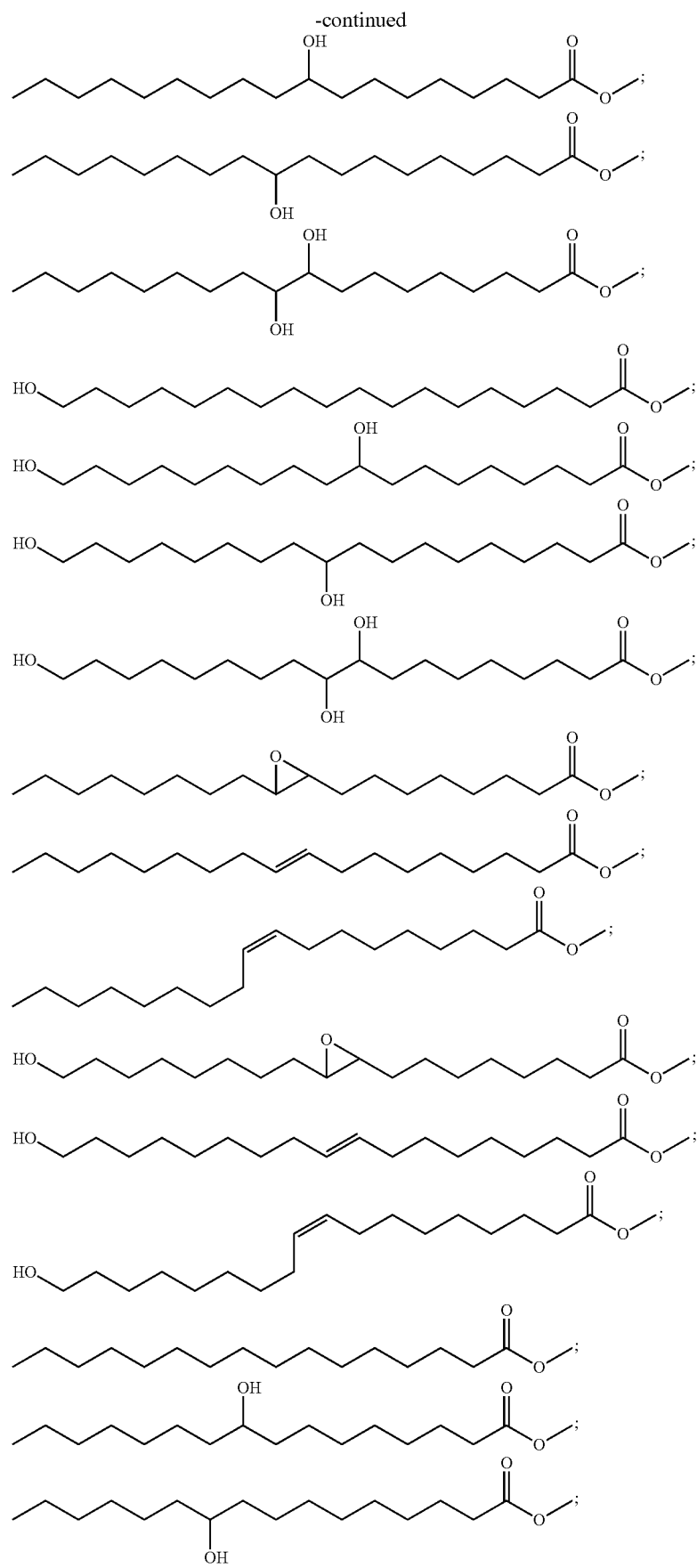

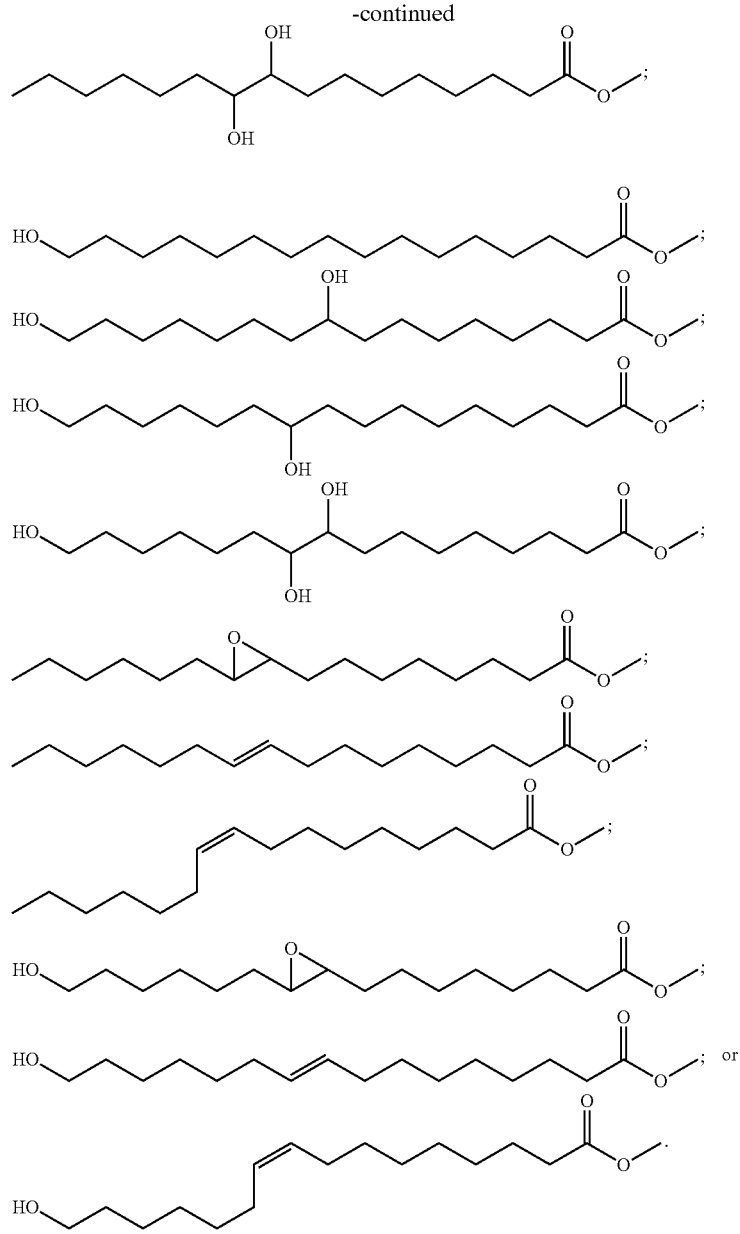
In some embodiments, the coating agent includes one or more of the following ethyl ester compounds:
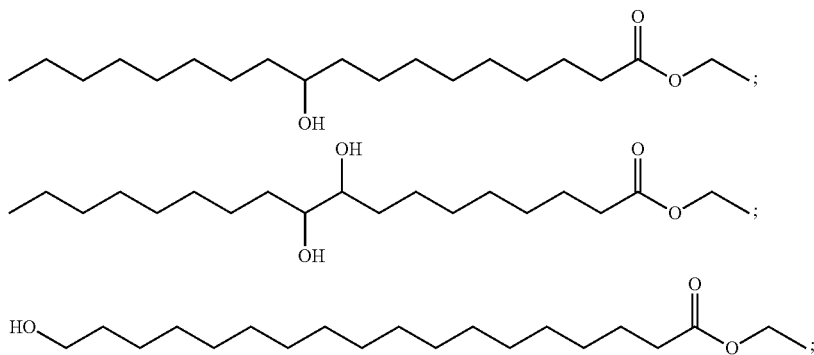

-continued
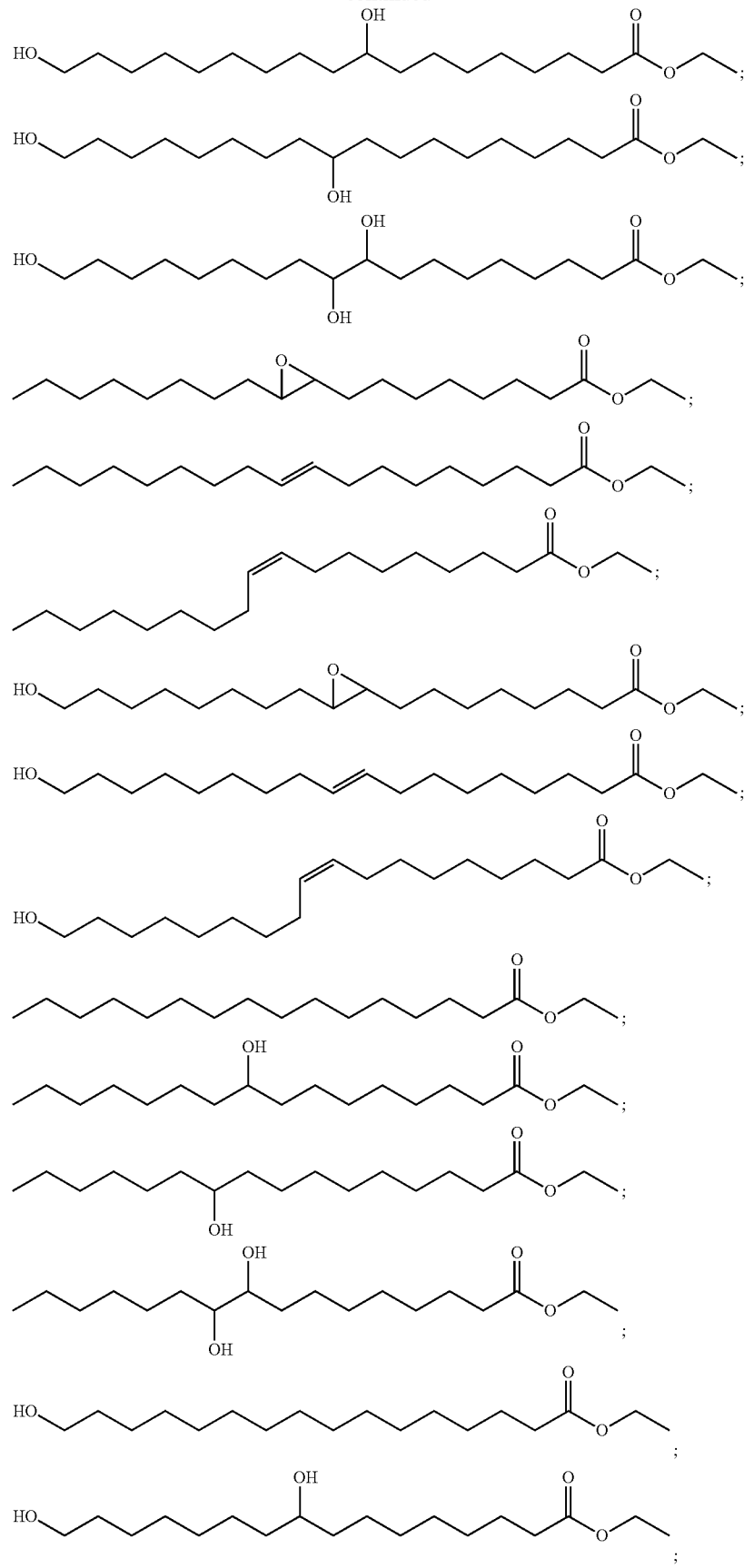

-continued
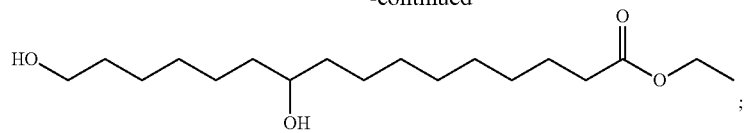
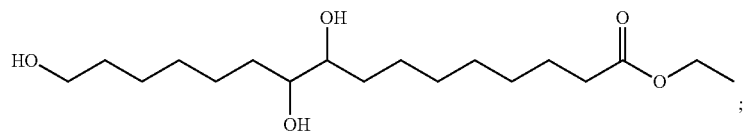
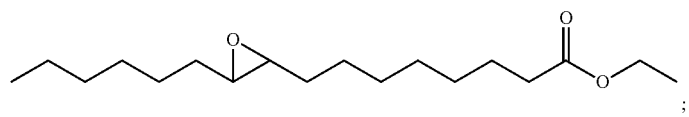
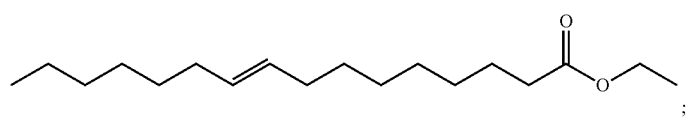
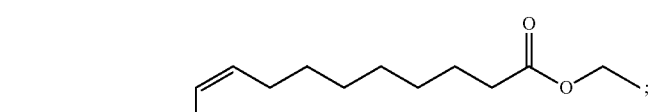
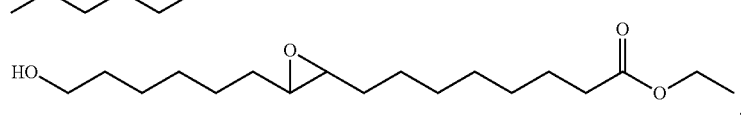
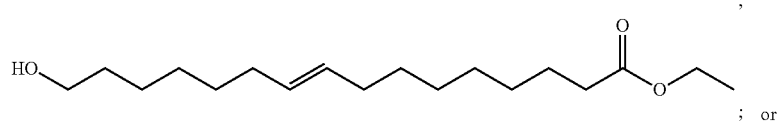
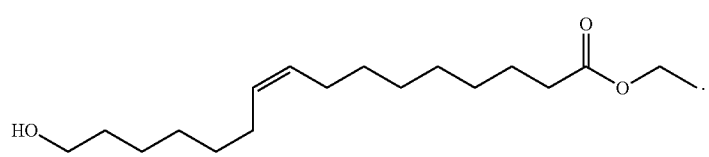
45
In some embodiments, the coating agent includes one or more of the following 2-glycerol ester compounds:
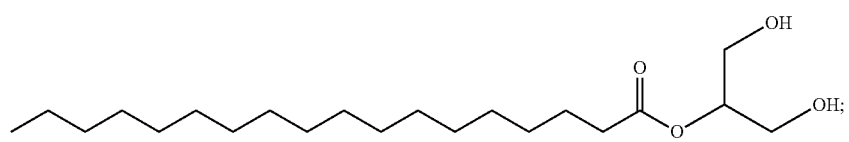
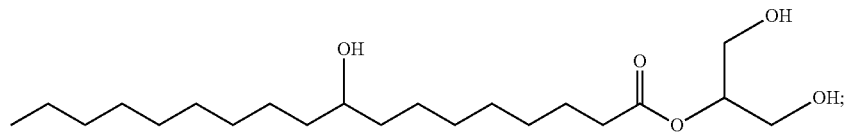
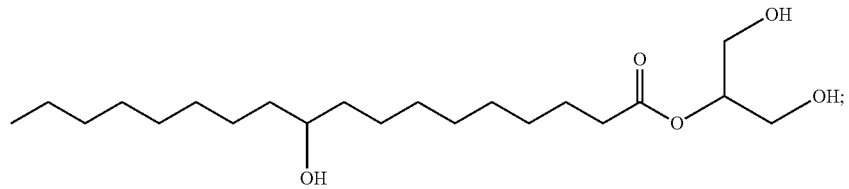

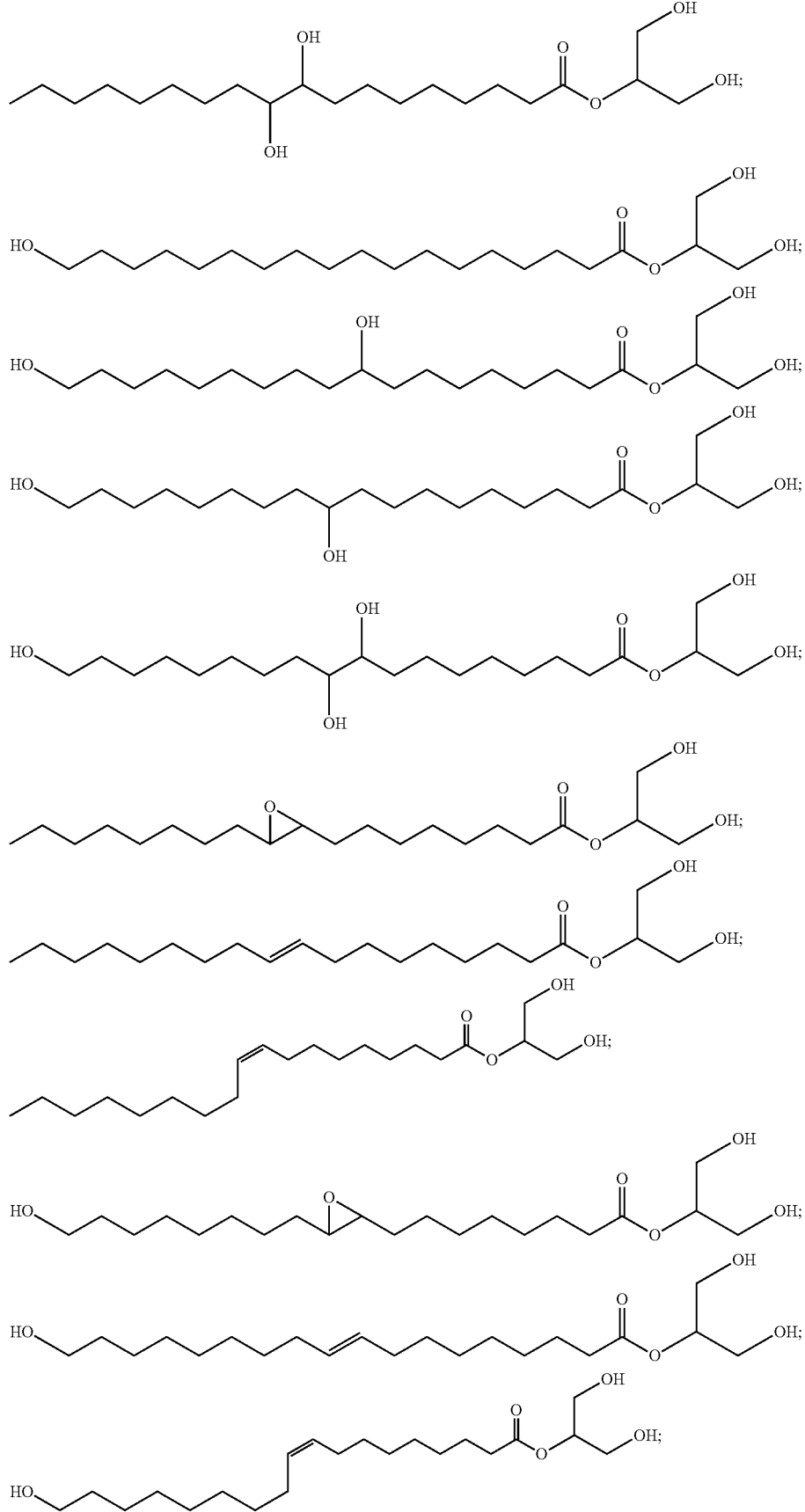

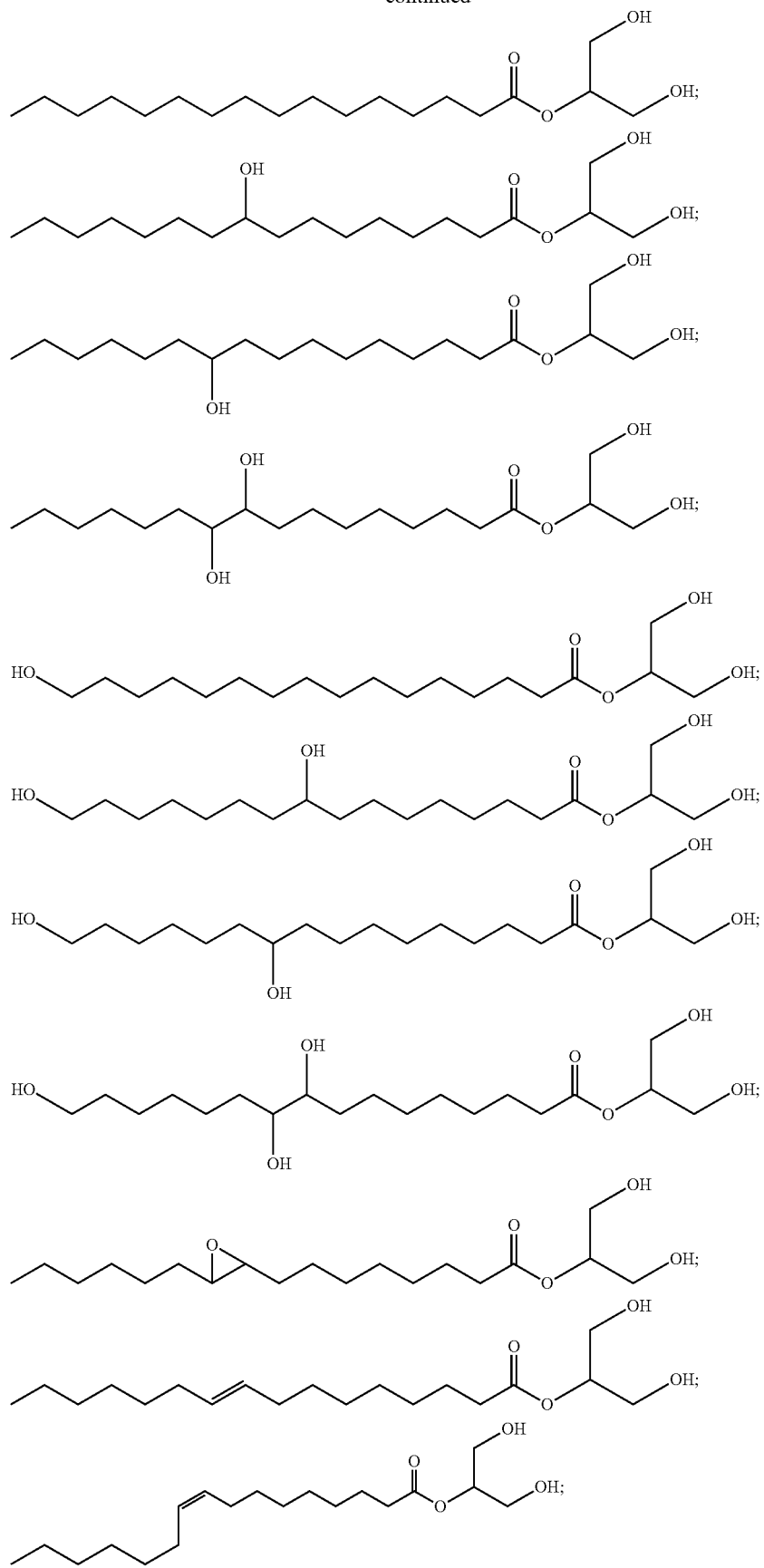

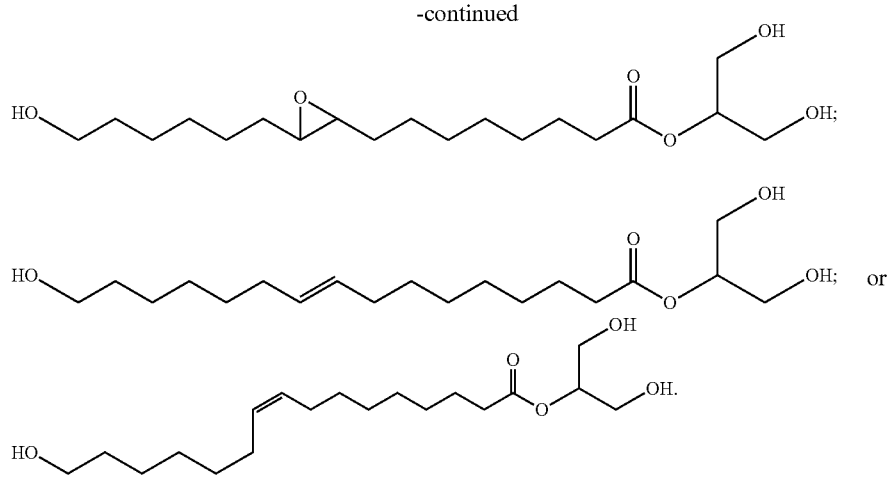
In some embodiments, the coating agent includes one or more of the following 1-glycerol ester compounds:
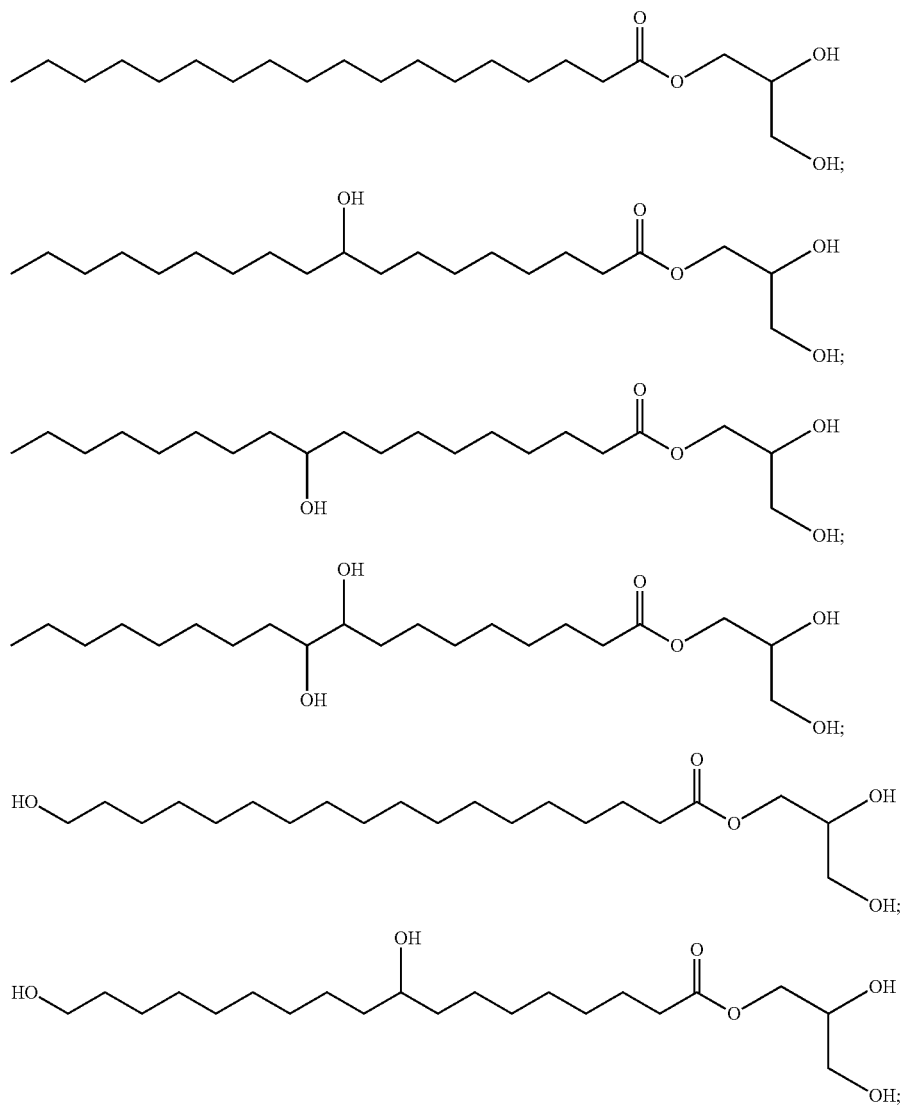

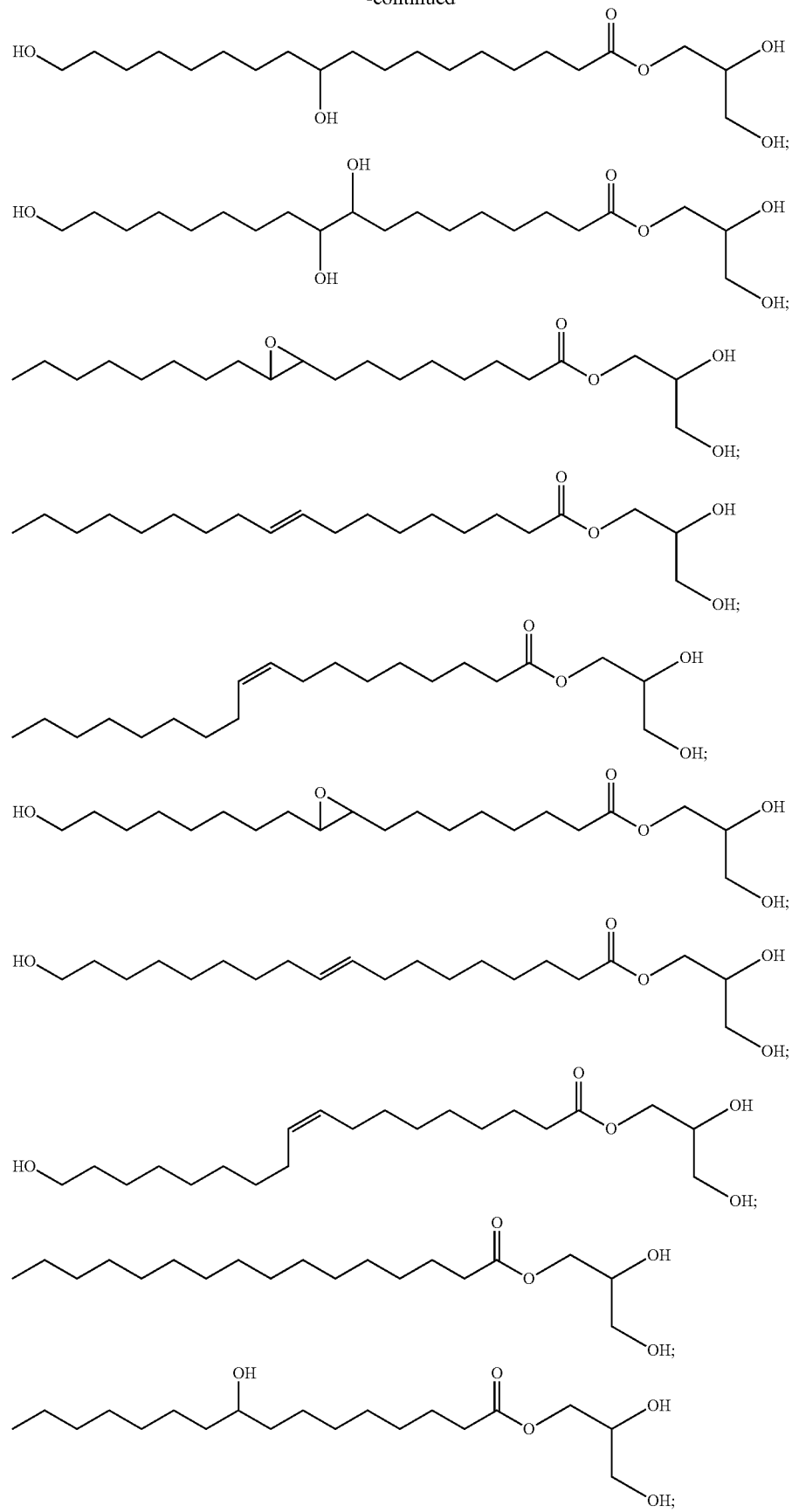

-continued
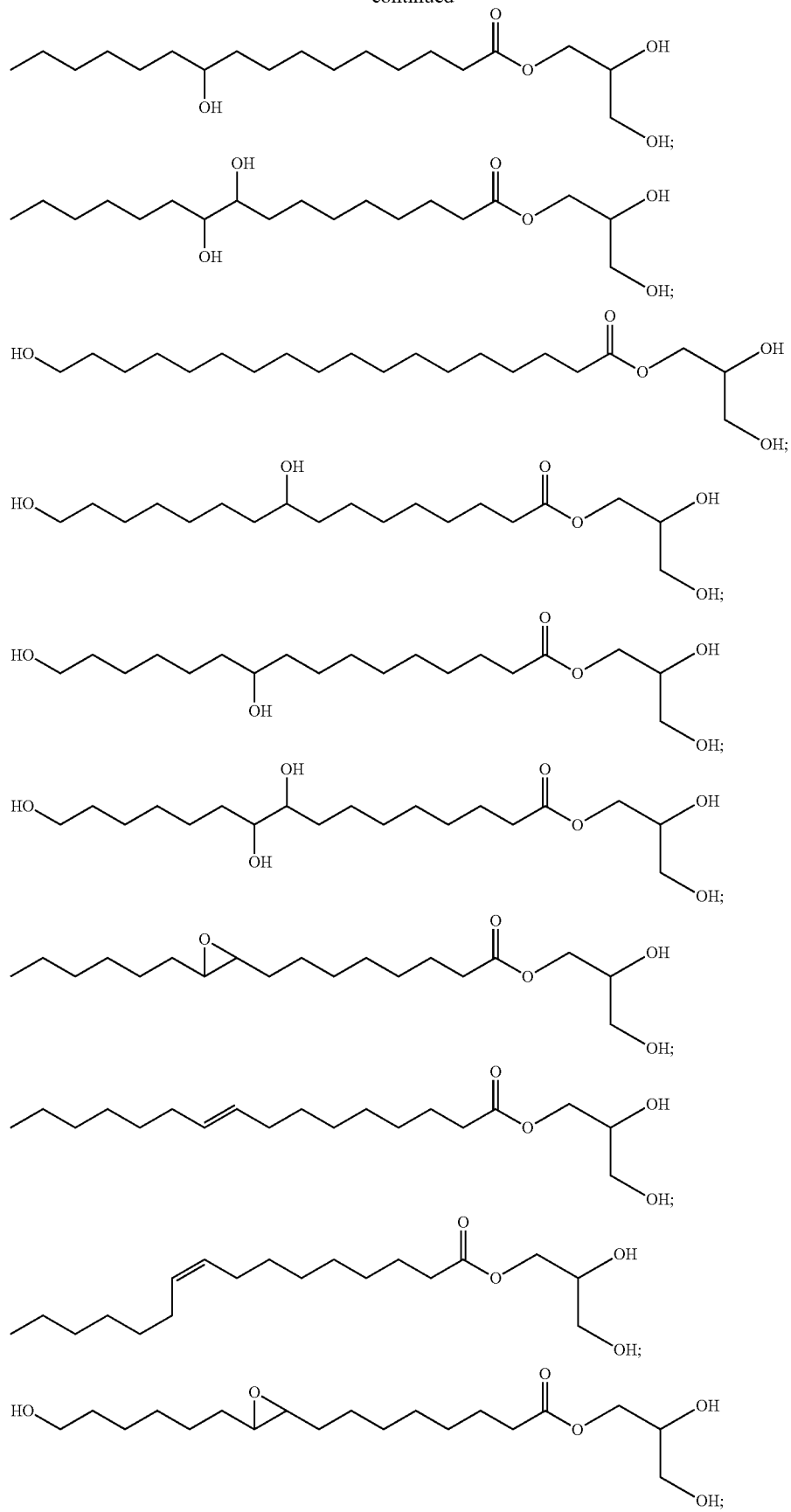

-continued

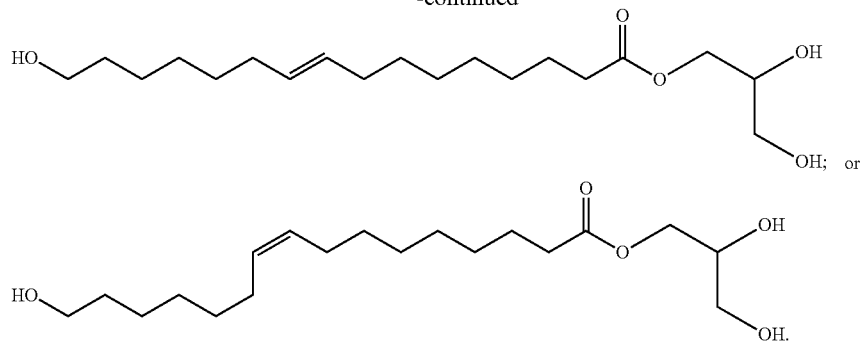

In some embodiments, the coating components (e.g., monomers, oligomers, fatty acids, esters, amides, amines, thiols, carboxylic acids, ethers, aliphatic waxes, alcohols, salts (inorganic and organic), or combinations thereof) are derived from plant matter. In some embodiments, the coating components are derived from cutin. The steps of sanitizing the produce and forming the protective coating over the surface of the produce can result in the produce being Ready-to-Eat. The steps of sanitizing the produce and forming the protective coating over the surface of the produce can also result in an increase in the shelf life of the produce as compared to untreated produce.

In some embodiments, the act of at least partially removing of the solvent from the surface of the produce can comprise removing at least 90% of the solvent from the surface of the produce.

Through extensive experimentation, the authors of the subject matter disclosed herein have found that coatings formed from the above coating components, and in particular from various combinations of 2-monoacylglycerides and one or more of the other compounds described above, are effective at preventing or mitigating surface damage caused by the sanitizing agent in a wide variety of agricultural products, including strawberries, blueberries, avocados, and finger limes. Furthermore, coatings formed from the above compounds have also been shown to be highly effective in reducing water loss and increasing the shelf life of the agricultural products, making them well suited for RTE formulations.

Properties of the coating, such as thickness, cross-link density, and permeability, can be varied to be suitable for a particular agricultural product by adjusting the specific composition of the coating agent, the specific composition of the solvent, the concentration of the coating agent in the solvent, and the conditions of the sanitization treatment/coating deposition process. The concentration of the solute (e.g., coating agent) in the solvent can, for example, be in a range of about 0.5 mg/mL to 200 mg/mL. Techniques for applying the solution to the surface of the agricultural product can, for example, include dipping and/or soaking the product in the solution or spraying the solution onto the surface of the product.

Figure 2:
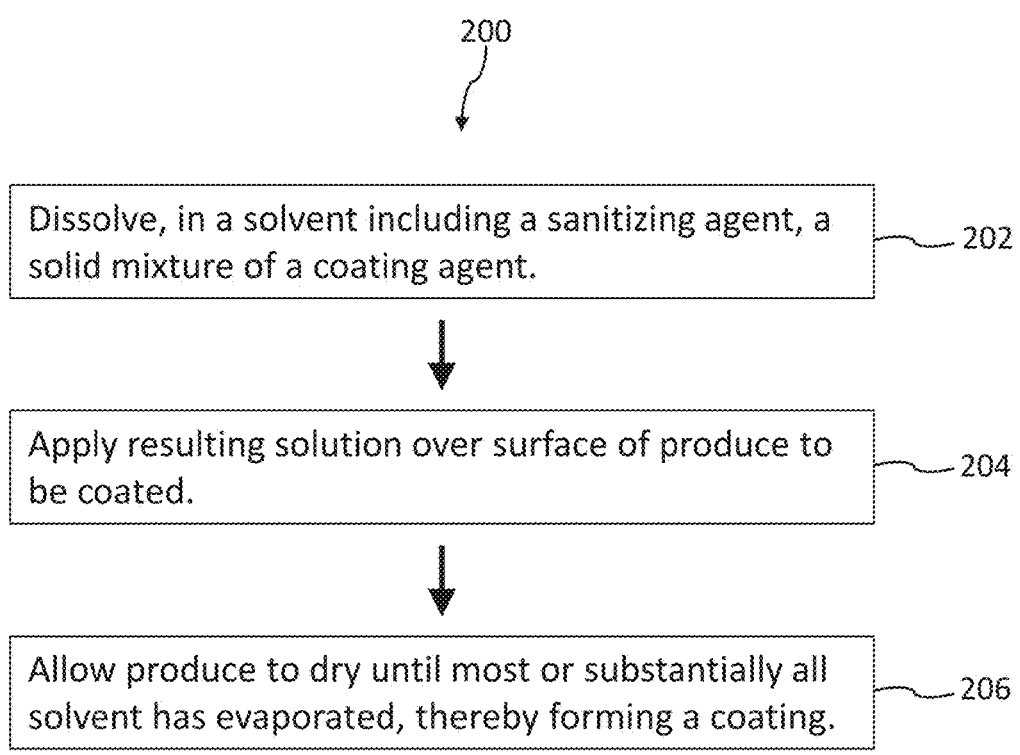
FIG. 2 illustrates a process for preparing sanitized (e.g., Ready-to-Eat) produce.

FIG. 2 illustrates an example process 200 for preparing sanitized (e.g., Ready-to-Eat or RTE) produce. First, a solid mixture of a coating agent (e.g., monomer and/or oligomer units) is dissolved in a solvent including a sanitizing agent (e.g., ethanol or water/ethanol mixture) to form a solution (step 202). The concentration of the solid mixture in the solvent can, for example, be in a range of about 0.1 to 200 mg/mL, such as in a range of about 0.1 to 100 mg/mL, 0.1 to 75 mg/mL, 0.1 to 50 mg/mL, 0.1 to 30 mg/mL, 0.1 to 20 mg/mL, 0.5 to 200 mg/mL, 0.5 to 100 mg/mL, 0.5 to 75 mg/mL, 0.5 to 50 mg/mL, 0.5 to 30 mg/mL, 0.5 to 20 mg/mL, 1 to 200 mg/mL, 1 to 100 mg/mL, 1 to 75 mg/mL, 1 to 50 mg/mL, 1 to 30 mg/mL, 1 to 20 mg/mL, 5 to 200 mg/mL, 5 to 100 mg/mL, 5 to 75 mg/mL, 5 to 50 mg/mL, 5 to 30 mg/mL, or 5 to 20 mg/mL. Next, the solution which includes the monomer and/or oligomer units is applied over the surface of the produce to be coated (step 204), for example by spray coating the produce or by dipping the produce in the solution. In the case of spray coating, the solution can, for example, be placed in a spray bottle which generates a fine mist spray. The spray bottle head can then be held approximately six to twelve inches from the produce, and the produce then sprayed. In the case of dip coating, the produce can, for example, be placed in a bag, the solution containing the composition poured into the bag, and the bag then sealed and lightly agitated until the entire surface of the produce is wet. After applying the solution to the produce, the produce is allowed to dry until most or substantially all of the solvent has evaporated, thereby allowing a coating composed of the monomer and/or oligomer units to form over the surface of the produce (step 206).

In some embodiments, the coating agent can independently be formulated to sanitize the surface in addition to protecting the surface by forming a protective coating thereon. For example, the coating agent can include chemical components that incorporate into the coatings which are operable to sanitize and/or disinfect the surface. In such embodiments, the subsequently formed coating may continue to reduce microorganism levels on the surface even after the sanitizing agent has been removed from the surface. However, in some cases including sanitizing components in the coating agent can degrade the performance of the subsequently formed protective coating. As such, in many cases it can be preferable for the sanitizing to be performed by the sanitizing agent (e.g., the solvent) and for the coating agent to be free of or lacking any sanitizing components. That is, the coating agent can be a non-sanitizing coating agent.

Without wishing to be bound by theory, at least some of the coating compositions (e.g., compounds of Formula I) do not independently prevent fungal growth or sanitize the surface of an edible substrate. For example, at least some coating compositions described herein, when applied to the surface of an edible substrate using water as a solvent, will not prevent fungal growth or sanitize the edible substrate. However, when the coating compositions described herein are dissolved in a solvent comprising a sanitizing agent, for example a solvent having at least 30% ethanol (e.g., between 30% and 100% ethanol), the resulting solutions can prevent fungal growth and/or sanitize the surface of the edible substrate. Additionally, the coating compositions left over on the surface of the edible substrate can further serve to increase the shelf-life of the substrate (e.g., by preventing moisture loss).

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

For each of the Examples below, palmitic acid was purchased from Sigma Aldrich, 2,3-dihydroxypropan-2-yl hexadecanoate was purchased from Tokyo Chemical Industry Co, 1,3-dihydroxypropan-2-yl hexadecanoate was prepared following the method of Example 1, stearic acid (octadecanoic acid) was purchased from Sigma Aldrich, 2,3-dihydroxypropan-2-yl octadecanoate was purchased from Alfa Aesar, 1,3-dihydroxypropan-2-yl octadecanoate was prepared following the method of Example 2, tetradecanoic acid was purchased from Sigma Aldrich, 2,3-dihydroxypropan-2-yl tetradecanoate was purchased from Tokyo Chemical Industry Co, oleic acid was purchased from Sigma Aldrich, and ethyl palmitate (EtPA) was purchased from Sigma Aldrich. All solvents and other chemical reagents were obtained from commercial sources (e.g., Sigma-Aldrich (St. Louis, Mo.)) and were used without further purification unless noted otherwise.

Example 1

Synthesis of 1,3-dihydroxypropan-2-yl Hexadecanoate for use as a Coating Agent Component

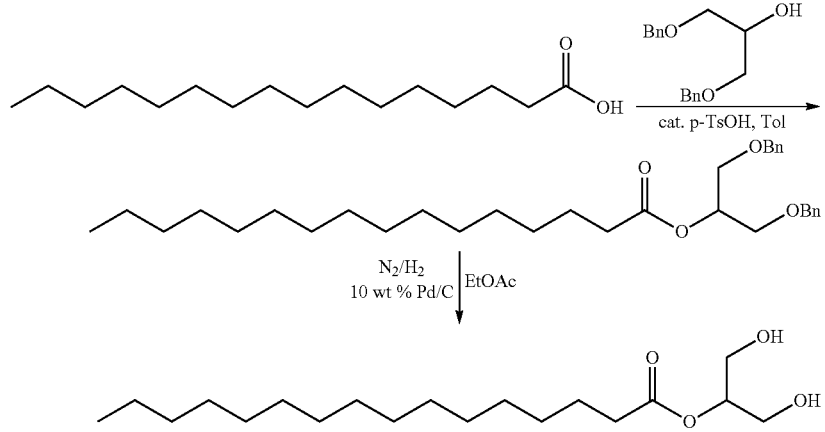

Step 1. 1,3-bis(benzyloxy)propan-2-yl hexadecanoate

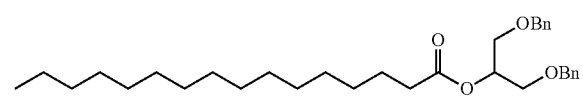 [SMILES: CCCCCCCCCCCCCCCC(=O)OC(COCc1ccccc1)COCc1ccccc1]

70.62 g (275.34 mmol) of palmitic acid, 5.24 g (27.54 mmol) of p-TsOH, 75 g (275.34 mmol) of 1,3-bis(benzyloxy)propan-2-ol, and 622 mL of toluene were charged into a round bottom flask equipped with a Teflon coated magnetic stir bar. A Dean-Stark Head and condenser were attached to the flask and a positive flow of Na was initiated. The flask was heated to reflux in a heating mantle while the reaction mixture was stirred vigorously until the amount of water collected (~5 mL) in the Dean-Stark Head indicated full ester conversion (~8 hr). The flask was allowed to cool down to room temperature and the reaction mixture was poured into a separatory funnel containing 75 mL of a saturated aqueous solution of $Na_2CO_3$ and 75 mL of brine. The toluene fraction was collected and the aqueous layer was extracted with 125 mL of $Et_2O$. The organic layers were combined and washed with 100 mL of brine, dried over $MgSO_4$, filtered and concentrated in vacuo. The crude colorless oil was dried under high vacuum providing (135.6 g, 265.49 mmol, crude yield=96.4%) of 1,3-bis(benzyloxy)propan-2-yl hexadecanoate.

HRMS (ESI-TOF) (m/z): calcd. for $C_{33}H_{50}O_4Na$, [M+Na]$^+$, 533.3607; found, 533.3588;

$^1$H NMR (600 MHz, CDCl$_3$): δ 7.41-7.28 (m, 10H), 5.28 (p, J=5.0 Hz, 1H), 4.59 (d, J=12.1 Hz, 2H), 4.54 (d, J=12.1 Hz, 2H), 3.68 (d, J=5.2 Hz, 4H), 2.37 (t, J=7.5 Hz, 2H), 1.66 (p, J=7.4 Hz, 2H), 1.41-1.15 (m, 24H), 0.92 (t, J=7.0 Hz, 3H) ppm.

$^{13}$C NMR (151 MHz, CDCl$_3$): δ 173.37, 138.09, 128.43, 127.72, 127.66, 73.31, 71.30, 68.81, 34.53, 32.03, 29.80, 29.79, 29.76, 29.72, 29.57, 29.47, 29.40, 29.20, 25.10, 22.79, 14.23 ppm.

Step 2. 1,3-dihydroxypropan-2-yl hexadecanoate 7.66 g (15.00 mmol) of 1,3-bis(benzyloxy)propan-2-yl hexadecanoate, 79.8 mg (0.75 mmol) of 10 wt% Pd/C and 100 mL of EtOAc were charged to a 3 neck round bottom flask equipped with a Teflon coated magnetic stir bar. A cold finger, with a bubbler filled with oil attached to it, and a bubbling stone connected to a 1:4 mixture of $H_2/N_2$ gas tank were affixed to the flask. $H_2/N_2$ was bubbled at 1.2 LPM into the flask until the disappearance of both starting material and mono-deprotected substrate as determined by TLC (~60 min). Once complete, the reaction mixture was filtered through a plug of Celite, which was then washed with 100 mL of EtOAc. The filtrate was placed in a refrigerator at 4° C. for 24 hrs. The precipitate from the filtrate (white and transparent needles) was filtered and dried under high vacuum yielding (2.124 g, 6.427 mmol, yield=42.8%) of 1,3-dihydroxypropan-2-yl hexadecanoate.

HRMS (FD-TOF) (m/z): calcd. for $C_{19}H_{38}O_4$, 330.2770; found, 330.2757;

$^1$H NMR (600 MHz, $CDCl_3$): δ 4.93 (p, J=4.7 Hz, 1H), 3.84 (t, J=5.0 Hz, 4H), 2.37 (t, J=7.6 Hz, 2H), 2.03 (t, J=6.0 Hz, 2H), 1.64 (p, J=7.6 Hz, 2H), 1.38-1.17 (m, 26H), 0.88 (t, J=7.0 Hz, 3H) ppm.

$^{13}$C NMR (151 MHz, $CDCl_3$): δ 174.22, 75.21, 62.73, 34.51, 32.08, 29.84, 29.83, 29.81, 29.80, 29.75, 29.61, 29.51, 29.41, 29.26, 25.13, 22.85, 14.27 ppm.

Example 2

Synthesis of 1,3-dihydroxypropan-2-yl Octadecanoate for use as a Coating Agent Component

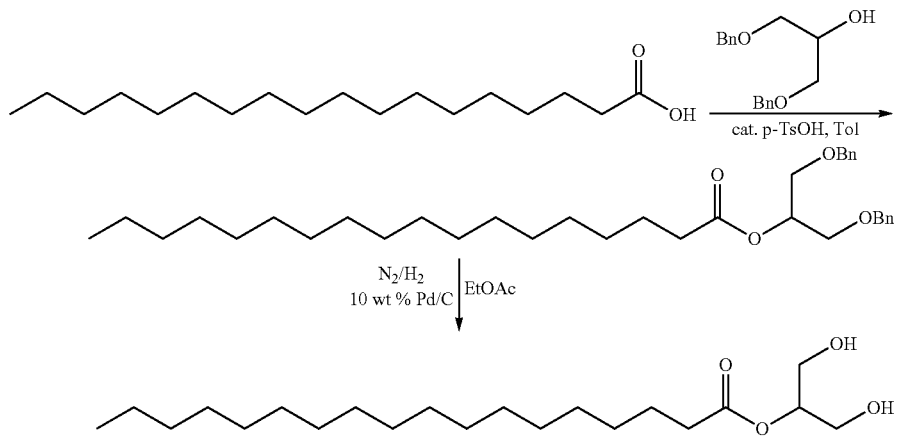

Step 1. 1,3-bis(benzyloxy)propan-2-yl stearate

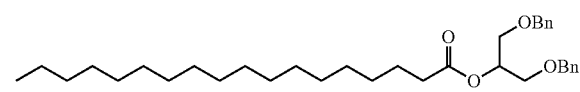 [SMILES: CCCCCCCCCCCCCCCCCC(=O)OC(COCc1ccccc1)COCc1ccccc1]

28.45 g (100 mmol) of stearic acid acid, 0.95 g (5 mmol) of p-TsOH, 27.23 g (275.34 mmol) of 1,3-bis(benzyloxy)propan-2-ol, and 200 mL of toluene were charged into a round bottom flask equipped with a Teflon coated magnetic stir bar. A Dean-Stark Head and condenser were attached to the flask and a positive flow of Na was initiated. The flask was heated to reflux in an oil bath while the reaction mixture was stirred vigorously until the amount of water collected (~1.8 mL) in the Dean-Stark Head indicated full ester conversion (~16 hr). The flask was allowed to cool down to room temperature and the solution was diluted with 100 mL of hexanes. The reaction mixture was poured into a separatory funnel containing 50 mL of a saturated aqueous solution of $Na_2CO_3$. The organic fraction was collected and the aqueous layer was extracted twice more with 50 mL portions of hexanes. The organic layers were combined and washed with 100 mL of brine, dried over $MgSO_4$, filtered and concentrated in vacuo. The crude colorless oil was further purified by selective liquid-liquid extraction using hexanes and acetonitrile and the product was again concentrated in vacuo, yielding (43.96 g, 81.60 mmol, yield=81.6%) of 1,3-bis(benzyloxy)propan-2-yl stearate.

$^1$H NMR (600 MHz, $CDCl_3$): δ 7.36-7.27 (m, 10H), 5.23 (p, J=5.0 Hz, 1H), 4.55 (d, J=12.0 Hz, 2H), 4.51 (d, J=12.1 Hz, 2H), 3.65 (d, J=5.0 Hz, 4H), 2.33 (t, J=7.5 Hz, 2H), 1.62 (p, J=7.4 Hz, 2H), 1.35-1.22 (m, 25H), 0.88 (t, J=6.9 Hz, 3H) ppm.

Step 2. 1,3-dihydroxypropan-2-yl stearate

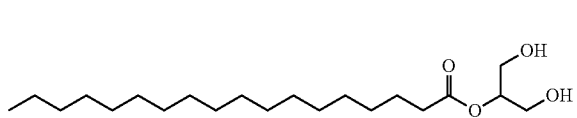 [SMILES: CCCCCCCCCCCCCCCCCC(=O)OC(CO)CO]

6.73 g (12.50 mmol) of 1,3-bis(benzyloxy)propan-2-yl stearate, 439 mg (0.625 mmol) of 20 wt % $Pd(OH)_2/C$ and 125 mL of EtOAc were charged to a 3 neck round bottom flask equipped with a Teflon coated magnetic stir bar. A cold finger, with a bubbler filled with oil attached to it, and a bubbling stone connected to a 1:4 mixture of $H_2/N_2$ gas tank were affixed to the flask. $H_2/N_2$ was bubbled at 1.2 LPM into the flask until the disappearance of both starting material and mono-deprotected substrate as determined by TLC (~120 min). Once complete, the reaction mixture was filtered through a plug of Celite, which was then washed with 150 mL of EtOAc. The filtrate was placed in a refrigerator at 4° C. for 48 hrs. The precipitate from the filtrate (white and transparent needles) was filtered and dried under high vacuum yielding (2.12 g, 5.91 mmol, yield=47.3%) of 1,3-dihydroxypropan-2-yl stearate.

LRMS (ESI+) (m/z): calcd. for $C_{21}H_{43}O_4$ $[M+H]^+$, 359.32; found 359.47.

$^1$H NMR (600 MHz, $CDCl_3$): δ 4.92 (p, J=4.7 Hz, 1H), 3.88-3.78 (m, 4H), 2.40-2.34 (m, 2H), 2.09 (t, J=6.2 Hz, 2H), 1.64 (p, J=7.3 Hz, 2H), 1.25 (s, 25H), 0.88 (t, J=7.0 Hz, 3H) ppm.

$^{13}$C NMR (151 MHz, $CDCl_3$): δ 174.32, 75.20, 62.63, 34.57, 32.14, 29.91, 29.89, 29.87, 29.82, 29.68, 29.57, 29.47, 29.33, 25.17, 22.90, 14.32 ppm.

Example 3

Effect of Ethanol on Post-Harvest Mass Loss of Blueberries

Blueberries were harvested simultaneously and divided into four groups of sixty blueberries each, each of the groups being qualitatively identical (i.e., all groups had blueberries of approximately the same average size and quality). The first group of blueberries was not washed or treated in any way and served as a control group. The second group was treated in a 1:1 mixture of ethanol and water. The third group was treated in a 3:1 mixture of ethanol and water, and the fourth group was treated in pure ethanol.

To treat the blueberries with the various solvents, the blueberries were placed in bags, and the solvent was poured into the bag. The bag was then sealed and lightly agitated until the entire surface of each blueberry was wet. The blueberries were then removed from the bag and allowed to dry on drying racks. The blueberries were kept under ambient room conditions at a temperature in the range of 23° C.-27° C. and humidity in the range of 40%-55% while they dried and for the entire duration of the time they were tested.

FIG. 1 shows the percent mass loss of the four groups of blueberries as a function of time. Plot 102 shows the first (control) group. Plot 104 shows the second group treated with 1:1 ethanol and water. Plot 106 shows the third group treated with 3:1 ethanol and water. Plot 108 shows the fourth group treated with pure ethanol.

Example 4

Use of Coating Agents to Reduce Spoilage of Blueberries—Effect of Solvent

Two solutions of coating agents dissolved in a solvent were prepared to examine the effect of the solvent on the rate of mass loss of blueberries after treatment with the solution to form a coating over the blueberries. The first solution contained a 3:1 mixture by mass of 1,3-dihydroxypropan-2-yl hexadecanoate (i.e., a 2-monoacylglyceride) and 2,3-dihydroxypropan-2-yl hexadecanoate (i.e., a 1-monoacylglyceride) dissolved in pure ethanol at a concentration of 10 mg/mL. The second solution contained a 3:1 mixture by mass of 1,3-dihydroxypropan-2-yl hexadecanoate (i.e., a 2-monoacylglyceride) and 2,3-dihydroxypropan-2-yl hexadecanoate (i.e., a 1-monoacylglyceride) dissolved in a mixture of 90% ethanol and 10% water at a concentration of 10 mg/mL.

Blueberries were harvested simultaneously and divided into three groups of sixty blueberries each, each of the groups being qualitatively identical (i.e., all groups had blueberries of approximately the same average size and quality). The first group of blueberries (corresponding to 302 in FIG. 3) was not washed or treated in any way and served as a control group. The second group was treated with the solution of 1,3-dihydroxypropan-2-yl hexadecanoate and 2,3-dihydroxypropan-2-yl hexadecanoate (coating agent) in pure ethanol (sanitizing agent), and the third group was treated with the solution of 1,3-dihydroxypropan-2-yl hexadecanoate and 2,3-dihydroxypropan-2-yl hexadecanoate (coating agent) in the mixture of 90% ethanol (sanitizing agent) and 10% water.

Each of the treatments above, which served to sanitize the blueberries and form the coatings, was performed as follows. The blueberries were placed in bags, and the solution containing the sanitizing agent and the coating agent was poured into the bag. The bag was then sealed and lightly agitated until the entire surface of each blueberry was wet. The blueberries were then removed from the bag and allowed to dry on drying racks. The blueberries were kept under ambient room conditions at a temperature in the range of 23° C.-27° C. and humidity in the range of 40%-55% while they dried and for the entire duration of the time they were tested.

FIG. 3 shows plots of percent mass loss of blueberries versus time for untreated (control) blueberries (plot 302), for blueberries treated with solutions including coating agents dissolved in pure ethanol (plot 308), and for blueberries treated with coating agents dissolved in 90% ethanol (plot 306). As shown, the blueberries treated with solutions including both a sanitizing agent and a coating agent exhibited a substantially lower rate of mass loss during the four days after harvesting as compared to the untreated blueberries. After just under four days, the untreated blueberries (302) experienced an average percent mass loss of 15.4%, the blueberries treated in the solution including the coating agent dissolved in pure ethanol (308) experienced an average percent mass loss of 11.8%, and the blueberries treated in the solution including the coating agent dissolved in the 90% mixture of ethanol and water (306) experienced an average percent mass loss of 10.6%.

Example 5

Use of Coating Agents to Reduce Spoilage of Blueberries—Effect of Coating Agent Composition Using $C_{16}$ Glyceryl Esters Five solutions using $C_{16}$ glyceryl esters were prepared to examine the effect of the coating agent composition on the rate of mass loss on blueberries treated with a solution comprising the coating agent dissolved in a sanitizing agent to form a coating over the blueberries. Each solution was composed of the coating agents described below in pure ethanol at a concentration of 10 mg/mL. The first solution contained pure 2,3-dihydroxypropan-2-yl hexadecanoate. The second solution contained 75% 2,3-dihydroxypropan-2-yl hexadecanoate and 25% 1,3-dihydroxypropan-2-yl hexadecanoate by mass. The third solution contained 50% 2,3-dihydroxypropan-2-yl hexadecanoate and 50% 1,3-dihydroxypropan-2-yl hexadecanoate by mass. The fourth solution contained 25% 2,3-dihydroxypropan-2-yl hexadecanoate and 75% 1,3-dihydroxypropan-2-yl hexadecanoate by mass. The fifth solution contained pure 1,3-dihydroxypropan-2-yl hexadecanoate.

Blueberries were harvested simultaneously and divided into six groups of 60 blueberries each, each of the groups being qualitatively identical (i.e., all groups had blueberries of approximately the same average size and quality). In order to sanitize the blueberries and form the coatings, the blueberries were placed in bags, and the solution containing the sanitizing agent and the coating agent was poured into the bag. The bag was then sealed and lightly agitated until the entire surface of each blueberry was wet. The blueberries were then removed from the bag and allowed to dry on drying racks. The blueberries were kept under ambient room conditions at a temperature in the range of 23° C.-27° C. and humidity in the range of 40%-55% while they dried and for the entire duration of the time they were tested.

FIG. 4 is a graph showing average daily mass loss rates for blueberries coated with the five experimental coating solutions as well as a control group of untreated blueberries, measured over the course of several days. As shown in FIG.

4, the untreated blueberries (402) exhibited an average mass loss rate of 2.42% per day. The average daily mass loss rate of the blueberries treated with the pure 2,3-dihydroxypropan-2-yl hexadecanoate formulation (404) was 2.18%. The average daily mass loss rate of the blueberries treated with the pure 1,3-dihydroxypropan-2-yl hexadecanoate formulation (412) was 2.23%. The average daily mass loss rate of the blueberries treated with the formulation composed of 75% 2,3-dihydroxypropan-2-yl hexadecanoate and 25% 1,3-dihydroxypropan-2-yl hexadecanoate (406) was 2.13%. The average daily mass loss rate of the blueberries treated with the formulation composed of 50% 2,3-dihydroxypropan-2-yl hexadecanoate and 50% 1,3-dihydroxypropan-2-yl hexadecanoate (408) was 2.28%. The average daily mass loss rate of the blueberries treated with the formulation composed of 25% 2,3-dihydroxypropan-2-yl hexadecanoate and 75% 1,3-dihydroxypropan-2-yl hexadecanoate (410) was 1.92%.

Example 6

Use of Coating Agents to Reduce Spoilage of Blueberries—Effect of Coating Agent Composition Using $C_{18}$ Glyceryl Esters Five solutions using Cis glyceryl esters were prepared to examine the effect of the coating agent composition on the rate of mass loss of blueberries treated with a solution comprising the coating agent dissolved in a sanitizing agent to form a coating over the blueberries. Each solution was composed of the coating agents described below in pure ethanol at a concentration of 10 mg/mL. The first solution contained pure 2,3-dihydroxypropan-2-yl octadecanoate. The second solution contained 75% 2,3-dihydroxypropan-2-yl octadecanoate and 25% 1,3-dihydroxypropan-2-yl octadecanoate by mass. The third solution contained 50% 2,3-dihydroxypropan-2-yl octadecanoate and 50% 1,3-dihydroxypropan-2-yl octadecanoate by mass. The fourth solution contained 25% 2,3-dihydroxypropan-2-yl octadecanoate and 75% 1,3-dihydroxypropan-2-yl octadecanoate by mass. The fifth solution contained pure 1,3-dihydroxypropan-2-yl octadecanoate.

Blueberries were harvested simultaneously and divided into six groups of 60 blueberries each, each of the groups being qualitatively identical (i.e., all groups had blueberries of approximately the same average size and quality). In order to sanitize the blueberries and form the coatings, the blueberries were placed in bags, and the solution containing the sanitizing agent and the coating agent was poured into the bag. The bag was then sealed and lightly agitated until the entire surface of each blueberry was wet. The blueberries were then removed from the bag and allowed to dry on drying racks. The blueberries were kept under ambient room conditions at a temperature in the range of 23° C.-27° C. and humidity in the range of 40%-55% while they dried and for the entire duration of the time they were tested.

FIG. 5 is a graph showing average daily mass loss rates for blueberries coated with the five experimental coating agents as well as a control group of untreated blueberries, measured over the course of several days. As shown in FIG. 5, the results for 2,3-dihydroxypropan-2-yl octadecanoate/ 1,3-dihydroxypropan-2-yl octadecanoate coating agent mixtures were similar to those for 2,3-dihydroxypropan-2-yl hexadecanoate/1,3-dihydroxypropan-2-yl hexadecanoate coating agent mixtures in FIG. 4. The untreated blueberries (502) exhibited an average mass loss rate of 2.42% per day. The average daily mass loss rate of the blueberries treated with the pure 2,3-dihydroxypropan-2-yl octadecanoate formulation (504) was 2.11%. The average daily mass loss rate of the blueberries treated with the pure 1,3-dihydroxypropan-2-yl octadecanoate formulation (512) was 2.05%. The average daily mass loss rate of the blueberries treated with the formulation composed of 75% 2,3-dihydroxypropan-2-yl octadecanoate and 25% 1,3-dihydroxypropan-2-yl octadecanoate (506) was 2.14%. The average daily mass loss rate of the blueberries treated with the formulation composed of 50% 2,3-dihydroxypropan-2-yl octadecanoate and 50% 1,3-dihydroxypropan-2-yl octadecanoate (508) was 2.17%. The average daily mass loss rate of the blueberries treated with the formulation composed of 25% 2,3-dihydroxypropan-2-yl octadecanoate and 75% 1,3-dihydroxypropan-2-yl octadecanoate (510) was 1.9%.

Example 7

Use of Coating Agents to Reduce Spoilage of Blueberries—Effect of Coating Agent Concentration Two solutions including a mixture of 2,3-dihydroxypropan-2-yl hexadecanoate (25%) and 1,3-dihydroxypropan-2-yl hexadecanoate (75%) (coating agent) dissolved in pure ethanol (sanitizing agent) were prepared. For the first solution, the solute was dissolved in the ethanol at a concentration of 10 mg/mL, and for the second solution, the solute was dissolved in the ethanol at a concentration of 20 mg/mL.

Blueberries were harvested simultaneously and divided into three groups of 60 blueberries each, each of the groups being qualitatively identical (i.e., all groups had blueberries of approximately the same average size and quality). The first group was a control group of untreated blueberries, the second group was treated with the 10 mg/mL solution, and the third group was treated with the 20 mg/mL solution.

To treat the blueberries, each blueberry was picked up with a set of tweezers and individually dipped in the solution for approximately 1 second, after which the blueberry was placed on a drying rack and allowed to dry. The blueberries were kept under ambient room conditions at a temperature in the range of 23° C.-27° C. and humidity in the range of 40%-55% while they dried and for the entire duration of the time they were tested. Mass loss was measured by carefully weighing the blueberries each day, where the reported percent mass loss was equal to the ratio of mass reduction to initial mass.

FIG. 6 shows plots of the percent mass loss over the course of 5 days in untreated (control) blueberries (602), blueberries treated using the first solution of 10 mg/mL (604), and blueberries treated using the second solution of 20 mg/mL. As shown, the percent mass loss for untreated blueberries was 19.2% after 5 days, whereas the percent mass loss for blueberries treated with the 10 mg/mL solution was 15% after 5 days, and the percent mass loss for blueberries treated with the 20 mg/mL solution was 10% after 5 days.

FIG. 7 shows high resolution photographs of the untreated blueberries (602) and of the blueberries treated with the 10 mg/mL solution, taken at day 5. The skins of the uncoated blueberries (602) were highly wrinkled as a result of mass loss of the blueberries, whereas the skins of the blueberries treated with the 10 mg/mL solution (604) remained very smooth.

Example 8

Use of Coating Agents to Reduce Spoilage of Strawberries—Effect of Coating Agent Composition Using $C_{16}$ Glyceryl Esters Five solutions using $C_{16}$ glyceryl esters were prepared to examine the effect of the coating agent composition on the rate of mass loss on strawberries treated with a solution comprising the coating agent dissolved in a sanitizing agent to form a coating over the strawberries. Each solution was composed of the coating agents described below in pure ethanol at a concentration of 10 mg/mL.

The first solution contained pure 2,3-dihydroxypropan-2-yl hexadecanoate. The second solution contained 75% 2,3-dihydroxypropan-2-yl hexadecanoate and 25% 1,3-dihydroxypropan-2-yl hexadecanoate by mass. The third solution contained 50% 2,3-dihydroxypropan-2-yl hexadecanoate and 50% 1,3-dihydroxypropan-2-yl hexadecanoate by mass. The fourth solution contained 25% 2,3-dihydroxypropan-2-yl hexadecanoate and 75% 1,3-dihydroxypropan-2-yl hexadecanoate by mass. The fifth solution contained pure 1,3-dihydroxypropan-2-yl hexadecanoate.

Strawberries were harvested simultaneously and divided into six groups of 15 strawberries each, each of the groups being qualitatively identical (i.e., all groups had strawberries of approximately the same average size and quality). In order to sanitize the strawberries and form the coatings, the strawberries were spray coated according to the following procedure. First, the strawberries were placed on drying racks. The five solutions were each placed in a spray bottle which generated a fine mist spray. For each bottle, the spray head was held approximately six inches from the strawberries, and the strawberries were sprayed and then allowed to dry on the drying racks. The strawberries were kept under ambient room conditions at a temperature in the range of 23° C.-27° C. and humidity in the range of 40%-55% while they dried and for the entire duration of the time they were tested.

FIG. 8 is a graph showing average daily mass loss rates, measured over the course of 4 days, of the strawberries treated with each of the five solutions described above. The strawberries corresponding to bar 802 were untreated (control group). The strawberries corresponding to bar 804 were treated with the first solution (i.e., pure 2,3-dihydroxypropan-2-yl hexadecanoate). The strawberries corresponding to bar 806 were treated with the second solution (i.e., 75% 2,3-dihydroxypropan-2-yl hexadecanoate and 25% 1,3-dihydroxypropan-2-yl hexadecanoate). The strawberries corresponding to bar 808 were treated with the third solution (i.e., 50% 2,3-dihydroxypropan-2-yl hexadecanoate and 50% 1,3-dihydroxypropan-2-yl hexadecanoate). The strawberries corresponding to bar 810 were treated with the fourth solution (i.e., 25% 2,3-dihydroxypropan-2-yl hexadecanoate and 75% 1,3-dihydroxypropan-2-yl hexadecanoate). The strawberries corresponding to bar 812 were treated with the fifth solution (i.e., pure 1,3-dihydroxypropan-2-yl hexadecanoate).

As shown in FIG. 8, the untreated strawberries (802) exhibited an average mass loss rate of 7.6% per day. The strawberries treated with the pure 2,3-dihydroxypropan-2-yl hexadecanoate formulation (804) exhibited an average daily mass loss rate of 6.4%. The strawberries treated with the pure 1,3-dihydroxypropan-2-yl hexadecanoate formulation (812) exhibited an average daily mass loss rate of 6.1%. The strawberries corresponding to bar 806 (2,3-dihydroxypropan-2-yl hexadecanoate to 1,3-dihydroxypropan-2-yl hexadecanoate mass ratio of 3) exhibited an average daily mass loss rate of 5.9%. The strawberries corresponding to bar 808 exhibited an average daily mass loss rate of 5.1%. The strawberries corresponding to bar 810 exhibited an average daily mass loss rate of 4.8%.

FIG. 9 shows high resolution photographs of 4 coated and 4 uncoated strawberries over the course of 5 days at the temperature and humidity conditions described above, where the coated strawberries were treated with a solution for which the coating agent was a mixture of 2,3-dihydroxypropan-2-yl hexadecanoate and 1,3-dihydroxypropan-2-yl hexadecanoate combined at a mass ratio of 0.33, as in bar 810 in FIG. 8. As seen, the untreated strawberries began to exhibit fungal growth and discoloration by day 3, and were mostly covered in fungus by day 5. In contrast, the treated strawberries did not exhibit any fungal growth by day 5 and were largely similar in overall color and appearance on day 1 and day 5.

Example 9

Use of Coating Agents to Reduce Spoilage of Avocados—Effect of Coating Agent Composition Using Combinations of 1-Glyceryl and 2-Glyeryl Esters Nine solutions using combinations 1-glyceryl and 2-glyceryl esters were prepared to examine the effect of the coating agent composition on the rate of mass loss on avocados treated with a solution comprising the coating agent dissolved in a sanitizing agent to form a coating over the avocados. Each solution was composed of the coating agents described below dissolved in pure ethanol (sanitizing agent) at a concentration of 5 mg/mL.

The first solution contained 2,3-dihydroxypropan-2-yl tetradecanoate and 1,3-dihydroxypropan-2-yl hexadecanoate combined at a molar ratio of 1:3. The second solution contained 2,3-dihydroxypropan-2-yl tetradecanoate and 1,3-dihydroxypropan-2-yl hexadecanoate combined at a molar ratio of 1:1. The third solution contained 2,3-dihydroxypropan-2-yl tetradecanoate and 1,3-dihydroxypropan-2-yl hexadecanoate combined at a molar ratio of 3:1. The fourth solution contained 2,3-dihydroxypropan-2-yl hexadecanoate and 1,3-dihydroxypropan-2-yl hexadecanoate combined at a molar ratio of 3:1. The fifth solution contained 2,3-dihydroxypropan-2-yl hexadecanoate and 1,3-dihydroxypropan-2-yl hexadecanoate combined at a molar ratio of 1:1. The sixth solution contained 2,3-dihydroxypropan-2-yl hexadecanoate and 1,3-dihydroxypropan-2-yl hexadecanoate combined at a molar ratio of 1:3. The seventh solution contained 2,3-dihydroxypropan-2-yl octadecanoate and 1,3-dihydroxypropan-2-yl hexadecanoate combined at a molar ratio of 1:3. The eighth solution contained 2,3-dihydroxypropan-2-yl octadecanoate and 1,3-dihydroxypropan-2-yl hexadecanoate combined at a molar ratio of 1:1. The ninth solution contained 2,3-dihydroxypropan-2-yl octadecanoate and 1,3-dihydroxypropan-2-yl hexadecanoate combined at a molar ratio of 3:1.

Avocados were harvested simultaneously and divided into nine groups of 30 avocados, each of the groups being qualitatively identical (i.e., all groups had avocados of approximately the same average size and quality). In order to sanitize the avocados and form the coatings, the avocados were each individually dipped in one of the solutions, with each group of 30 avocados being treated with the same solution. The avocados were then placed on drying racks and allowed to dry under ambient room conditions at a temperature in the range of about 23° C.-27° C. and relative humidity in the range of about 40%-55%. The avocados were all held at these same temperature and humidity conditions for the entire duration of time they were tested.

FIG. 10 is a graph showing the shelf life factor for avocados that were each treated with one of the nine solutions described above. Bar 1002 corresponds to the first solution (1:3 mixture of 2,3-dihydroxypropan-2-yl tetradecanoate (MA1G) and 1,3-dihydroxypropan-2-yl hexadecanoate (PA2G)), bar 1004 corresponds to the second solution (1:1 mixture of 2,3-dihydroxypropan-2-yl tetradecanoate and 1,3-dihydroxypropan-2-yl hexadecanoate), bar 1006 corresponds to the third solution (3:1 mixture of 2,3-dihydroxypropan-2-yl tetradecanoate and 1,3-dihydroxypropan-2-yl hexadecanoate), bar 1012 corresponds to the fourth solution (1:3 mixture of 2,3-dihydroxypropan-2-yl hexadecanoate (PA1G) and 1,3-dihydroxypropan-2-yl hexadecanoate (PA2G)), bar 1014 corresponds to the fifth solution (1:1 mixture of 2,3-dihydroxypropan-2-yl hexadecanoate and 1,3-dihydroxypropan-2-yl hexadecanoate), bar 1016 corresponds to the sixth solution (3:1 mixture of 2,3-dihydroxypropan-2-yl hexadecanoate and 1,3-dihydroxypropan-2-yl hexadecanoate), bar 1022 corresponds to the seventh solution (1:3 mixture of 2,3-dihydroxypropan-2-yl octadecanoate (SA1G) and 1,3-dihydroxypropan-2-yl hexadecanoate (PA2G)), bar 1024 corresponds to the eighth solution (1:1 mixture of 2,3-dihydroxypropan-2-yl octadecanoate and 1,3-dihydroxypropan-2-yl hexadecanoate), and bar 1026 corresponds to the ninth solution (3:1 mixture of 2,3-dihydroxypropan-2-yl octadecanoate and 1,3-dihydroxypropan-2-yl hexadecanoate). As used herein, the term "shelf life factor" is defined as the ratio of the average daily mass loss rate of untreated produce (measured for a control group) to the average daily mass loss rate of the corresponding treated produce. Hence, a shelf life factor greater than 1 corresponds to a decrease in average daily mass loss rate of treated produce as compared to untreated produce, and a larger shelf life factor corresponds to a greater reduction in average daily mass loss rate.

As shown in FIG. 10, treatment in the first solution (1002) resulted in a shelf life factor of 1.48, treatment in the second solution (1004 resulted in a shelf life factor of 1.42, treatment in the third solution (1006) resulted in a shelf life factor of 1.35, treatment in the fourth solution (1012) resulted in a shelf life factor of 1.53, treatment in the fifth solution (1014) resulted in a shelf life factor of 1.45, treatment in the sixth solution (1016) resulted in a shelf life factor of 1.58, treatment in the seventh solution (1022) resulted in a shelf life factor of 1.54, treatment in the eighth solution (1024) resulted in a shelf life factor of 1.47, and treatment in the ninth solution (1026) resulted in a shelf life factor of 1.52.

Example 10

Use of Coating Agents to Reduce Spoilage of Avocados—Effect of Coating Agent Composition Using Combinations of Fatty Acids and Glyeryl Esters Nine solutions using combinations fatty acids and glyceryl esters were prepared to examine the effect of the coating agent composition on the rate of mass loss on avocados treated with a solution comprising the coating agent dissolved in a sanitizing agent to form a coating over the avocados. Each solution was composed of the coating agents described below dissolved in pure ethanol (sanitizing agent) at a concentration of 5 mg/mL.

The first solution contained tetradecanoic acid and 1,3-dihydroxypropan-2-yl hexadecanoate combined at a molar ratio of 1:3. The second solution contained tetradecanoic acid and 1,3-dihydroxypropan-2-yl hexadecanoate combined at a molar ratio of 1:1. The third solution contained tetradecanoic acid and 1,3-dihydroxypropan-2-yl hexadecanoate combined at a molar ratio of 3:1. The fourth solution contained hexadecanoic acid and 1,3-dihydroxypropan-2-yl hexadecanoate combined at a molar ratio of 1:3. The fifth solution contained hexadecanoic acid and 1,3-dihydroxypropan-2-yl hexadecanoate combined at a molar ratio of 1:1. The sixth solution contained hexadecanoic acid and 1,3-dihydroxypropan-2-yl hexadecanoate combined at a molar ratio of 3:1. The seventh solution contained octadecanoic acid and 1,3-dihydroxypropan-2-yl hexadecanoate combined at a molar ratio of 1:3. The eighth solution contained octadecanoic acid and 1,3-dihydroxypropan-2-yl hexadecanoate combined at a molar ratio of 1:1. The ninth solution contained octadecanoic acid and 1,3-dihydroxypropan-2-yl hexadecanoate combined at a molar ratio of 3:1.

Avocados were harvested simultaneously and divided into nine groups of 30 avocados, each of the groups being qualitatively identical (i.e., all groups had avocados of approximately the same average size and quality). In order to sanitize the avocados and form the coatings, the avocados were each individually dipped in one of the solutions, with each group of 30 avocados being treated with the same solution. The avocados were then placed on drying racks and allowed to dry under ambient room conditions at a temperature in the range of about 23° C.-27° C. and relative humidity in the range of about 40%-55%. The avocados were all held at these same temperature and humidity conditions for the entire duration of time they were tested.

FIG. 11 is a graph showing the shelf life factor for avocados that were each treated with one of the nine solutions described above. Bar 1102 corresponds to the first solution (1:3 mixture of tetradecanoic acid (MA) and 1,3-dihydroxypropan-2-yl hexadecanoate (PA2G)), bar 1104 corresponds to the second solution (1:1 mixture of tetradecanoic acid and 1,3-dihydroxypropan-2-yl hexadecanoate), bar 1106 corresponds to the third solution (3:1 mixture of tetradecanoic acid and 1,3-dihydroxypropan-2-yl hexadecanoate), bar 1112 corresponds to the fourth solution (1:3 mixture of hexadecanoic acid (PA) and 1,3-dihydroxypropan-2-yl hexadecanoate (PA2G)), bar 1114 corresponds to the fifth solution (1:1 mixture of hexadecanoic acid and 1,3-dihydroxypropan-2-yl hexadecanoate), bar 1116 corresponds to the sixth solution (3:1 mixture of hexadecanoic acid and 1,3-dihydroxypropan-2-yl hexadecanoate), bar 1122 corresponds to the seventh solution (1:3 mixture of octadecanoic acid (SA) and 1,3-dihydroxypropan-2-yl hexadecanoate (PA2G)), bar 1124 corresponds to the eighth solution (1:1 mixture of octadecanoic acid and 1,3-dihydroxypropan-2-yl hexadecanoate), and bar 1126 corresponds to the ninth solution (3:1 mixture of octadecanoic acid and 1,3-dihydroxypropan-2-yl hexadecanoate).

As shown in FIG. 11, treatment in the first solution (1102) resulted in a shelf life factor of 1.39, treatment in the second solution (1104) resulted in a shelf life factor of 1.35, treatment in the third solution (1106) resulted in a shelf life factor of 1.26, treatment in the fourth solution (1112) resulted in a shelf life factor of 1.48, treatment in the fifth solution (1114) resulted in a shelf life factor of 1.40, treatment in the sixth solution (1116) resulted in a shelf life factor of 1.30, treatment in the seventh solution (1122) resulted in a shelf life factor of 1.54, treatment in the eighth solution (1124) resulted in a shelf life factor of 1.45, and treatment in the ninth solution (1126) resulted in a shelf life factor of 1.35.

Example 11

Use of Coating Agents to Reduce Spoilage of Avocados—Effect of Coating Agent Composition Using Combinations of Ethyl Esters and Glyceryl Esters or Fatty Acids and Glyeryl Esters Fifteen solutions using combinations ethyl esters and glyceryl esters or fatty acids and glyceryl esters were prepared to examine the effect of the coating agent composition on the rate of mass loss on avocados treated with a solution comprising the coating agent dissolved in a sanitizing agent to form a coating over the avocados. Each solution was composed of the coating agents described below dissolved in pure ethanol (sanitizing agent) at a concentration of 5 mg/mL.

The first solution contained ethyl palmitate and 1,3-dihydroxypropan-2-yl hexadecanoate combined at a molar ratio of 1:3. The second solution contained ethyl palmitate and 1,3-dihydroxypropan-2-yl hexadecanoate combined at a molar ratio of 1:1. The third solution contained ethyl palmitate and 1,3-dihydroxypropan-2-yl hexadecanoate combined at a molar ratio of 3:1. The fourth solution contained oleic acid and 1,3-dihydroxypropan-2-yl hexadecanoate combined at a molar ratio of 1:3. The fifth solution contained oleic acid and 1,3-dihydroxypropan-2-yl hexadecanoate combined at a molar ratio of 1:1. The sixth solution contained oleic acid and 1,3-dihydroxypropan-2-yl hexadecanoate combined at a molar ratio of 3:1. The seventh solution contained tetradecanoic acid and 2,3-dihydroxypropan-2-yl octadecanoate combined at a molar ratio of 1:3. The eighth solution contained tetradecanoic acid and 2,3-dihydroxypropan-2-yl octadecanoate combined at a molar ratio of 1:1. The ninth solution contained tetradecanoic acid and 2,3-dihydroxypropan-2-yl octadecanoate combined at a molar ratio of 3:1. The tenth solution contained hexadecanoic acid and 2,3-dihydroxypropan-2-yl octadecanoate combined at a molar ratio of 1:3. The eleventh solution contained hexadecanoic acid and 2,3-dihydroxypropan-2-yl octadecanoate combined at a molar ratio of 1:1. The twelfth solution contained hexadecanoic acid and 2,3-dihydroxypropan-2-yl octadecanoate combined at a molar ratio of 3:1. The thirteenth solution contained octadecanoic acid and 2,3-dihydroxypropan-2-yl octadecanoate combined at a molar ratio of 1:3. The fourteenth solution contained octadecanoic acid and 2,3-dihydroxypropan-2-yl octadecanoate combined at a molar ratio of 1:1. The fifteenth solution contained octadecanoic acid and 2,3-dihydroxypropan-2-yl octadecanoate combined at a molar ratio of 3:1.

Avocados were harvested simultaneously and divided into fifteen groups of 30 avocados, each of the groups being qualitatively identical (i.e., all groups had avocados of approximately the same average size and quality). In order to sanitize the avocados and form the coatings, the avocados were each individually dipped in one of the solutions, with each group of 30 avocados being treated with the same solution. The avocados were then placed on drying racks and allowed to dry under ambient room conditions at a temperature in the range of about 23° C.-27° C. and relative humidity in the range of about 40%-55%. The avocados were all held at these same temperature and humidity conditions for the entire duration of time they were tested.

FIG. 12 is a graph showing the shelf life factor for avocados that were each treated with one of the fifteen solutions described above. Bar 1201 corresponds to the first solution (1:3 mixture of ethyl palmitate (EtPA) and 1,3-dihydroxypropan-2-yl hexadecanoate (PA2G)), bar 1202 corresponds to the second solution (1:1 mixture of ethyl palmitate and 1,3-dihydroxypropan-2-yl hexadecanoate), bar 1203 corresponds to the third solution (3:1 mixture of ethyl palmitate and 1,3-dihydroxypropan-2-yl hexadecanoate), bar 1211 corresponds to the fourth solution (1:3 mixture of oleic acid (OA) and 1,3-dihydroxypropan-2-yl hexadecanoate (PA2G)), bar 1212 corresponds to the fifth solution (1:1 mixture of oleic acid and 1,3-dihydroxypropan-2-yl hexadecanoate), bar 1213 corresponds to the sixth solution (3:1 mixture of oleic acid and 1,3-dihydroxypropan-2-yl hexadecanoate), bar 1221 corresponds to the seventh solution (1:3 mixture of tetradecanoic acid (MA) and 2,3-dihydroxypropan-2-yl octadecanoate (SA1G)), bar 1222 corresponds to the eighth solution (1:1 mixture of tetradecanoic acid and 2,3-dihydroxypropan-2-yl octadecanoate), bar 1223 corresponds to the ninth solution (3:1 mixture of octadecanoic acid and 2,3-dihydroxypropan-2-yl tetradecanoic), bar 1231 corresponds to the tenth solution (1:3 mixture of hexadecanoic acid (PA) and 2,3-dihydroxypropan-2-yl octadecanoate (SA1G)), bar 1232 corresponds to the eleventh solution (1:1 mixture of hexadecanoic acid and 2,3-dihydroxypropan-2-yl octadecanoate), bar 1233 corresponds to the twelfth solution (3:1 mixture of hexadecanoic acid and 2,3-dihydroxypropan-2-yl octadecanoate), bar 1241 corresponds to the thirteenth solution (1:3 mixture of octadecanoic acid (SA) and 2,3-dihydroxypropan-2-yl octadecanoate (SA1G)), bar 1242 corresponds to the fourteenth solution (1:1 mixture of octadecanoic acid and 2,3-dihydroxypropan-2-yl octadecanoate), and bar 1243 corresponds to the fifteenth solution (3:1 mixture of octadecanoic acid and 2,3-dihydroxypropan-2-yl octadecanoate).

As shown in FIG. 12, treatment in the first solution (1201) resulted in a shelf life factor of 1.54, treatment in the second solution (1202) resulted in a shelf life factor of 1.45, treatment in the third solution (1203) resulted in a shelf life factor of 1.32, treatment in the fourth solution (1211) resulted in a shelf life factor of 1.50, treatment in the fifth solution (1212) resulted in a shelf life factor of 1.32, treatment in the sixth solution (1213) resulted in a shelf life factor of 1.29, treatment in the seventh solution (1221) resulted in a shelf life factor of 1.76, treatment in the eighth solution (1222) resulted in a shelf life factor of 1.68, treatment in the ninth solution (1223) resulted in a shelf life factor of 1.46, treatment in the tenth solution (1231) resulted in a shelf life factor of 1.72, treatment in the eleventh solution (1232) resulted in a shelf life factor of 1.66, treatment in the twelfth solution (1233) resulted in a shelf life factor of 1.56, treatment in the thirteenth solution (1241) resulted in a shelf life factor of 1.76, treatment in the fourteenth solution (1242) resulted in a shelf life factor of 1.70, and treatment in the fifteenth solution (1243) resulted in a shelf life factor of 1.47.

Example 12

Effect of Solvent Composition in Solutions Used to Treat Pomegranates

Two solutions of coating agents dissolved in a solvent were prepared to examine the effect of the solvent composition on skin damage in pomegranates after treatment with the solution to form a coating over the pomegranates. The first solution contained a 30:70 mixture by mass of 2,3-dihydroxypropan-2-yl hexadecanoate (i.e., a 1-monoacylglyceride) and 1,3-dihydroxypropan-2-yl hexadecanoate (i.e., a 2-monoacylglyceride) dissolved in pure ethanol at a concentration of 40 mg/mL. The second solution contained a 30:70 mixture by mass of 2,3-dihydroxypropan-2-yl hexadecanoate (i.e., a 1-monoacylglyceride) and 1,3-dihydroxypropan-2-yl hexadecanoate (i.e., a 2-monoacylglyceride) dissolved in a mixture of 70% ethanol and 30% water at a concentration of 40 mg/mL.

Pomegranates were harvested simultaneously and divided into two groups of ten pomegranates each, with each of the groups being qualitatively identical (i.e., all groups had pomegranates of approximately the same average size and quality). The first group of pomegranates (corresponding to FIG. 13A) was treated with the solution of 2,3-dihydroxypropan-2-yl hexadecanoate and 1,3-dihydroxypropan-2-yl hexadecanoate (coating agent) in pure ethanol (sanitizing agent), and the second group (corresponding to FIG. 13B) was treated with the solution of 2,3-dihydroxypropan-2-yl hexadecanoate and 1,3-dihydroxypropan-2-yl hexadecanoate (coating agent) in the mixture of 70% ethanol (sanitizing agent) and 30% water.

Each of the treatments above, which served to sanitize the pomegranates and form coatings, was performed as follows. The pomegranates were placed in bags, and the solution containing the sanitizing agent and the coating agent was poured into the bag. The bag was then sealed and lightly agitated until the entire surface of each pomegranate was wet. The pomegranates were then removed from the bag and allowed to dry on drying racks. The pomegranates were kept under ambient room conditions at a temperature in the range of 23° C.-27° C. and humidity in the range of 40%-55% while they dried and for the entire duration of the time they were tested.

FIG. 13A is a high resolution photograph of one of the pomegranates that was treated with the first solution (30:70 mixture of 2,3-dihydroxypropan-2-yl hexadecanoate and 1,3-dihydroxypropan-2-yl hexadecanoate dissolved in pure ethanol), and FIG. 13B is a high resolution photograph of one of the pomegranates that was treated with the second solution (30:70 mixture of 2,3-dihydroxypropan-2-yl hexadecanoate and 1,3-dihydroxypropan-2-yl hexadecanoate dissolved in 70% ethanol). For the pomegranates treated with the 100% ethanol solution (FIG. 13A), the solvent contacted the surfaces of the pomegranates for about 30-60 seconds on average before completely evaporating away, after which the coating agent remained on the surfaces. For the pomegranates treated with the 70% ethanol solution (FIG. 13B), the solvent contacted the surfaces of the pomegranates for about 10 minutes on average before completely evaporating away, after which the coating agent remained on the surfaces. The images in FIGS. 13A and 13B are similar to and representative of all the other pomegranates in the respective groups. Visible skin breakdown was observed in all the pomegranates treated with the 100% ethanol solution (FIG. 13A), whereas the pomegranates treated with the 70% ethanol solution (FIG. 13B) all appeared undamaged and were otherwise unaltered in appearance by the treatment.

Example 13

Effect of Solvent Composition in Solutions Used to Treat Limes

Two solutions of coating agents dissolved in a solvent were prepared to examine the effect of the solvent composition on skin damage in limes after treatment with the solution to form a coating over the limes. The first solution contained a 30:70 mixture by mass of 2,3-dihydroxypropan-2-yl hexadecanoate (i.e., a 1-monoacylglyceride) and 1,3-dihydroxypropan-2-yl hexadecanoate (i.e., a 2-monoacylglyceride) dissolved in pure ethanol at a concentration of 40 mg/mL. The second solution contained a 30:70 mixture by mass of 2,3-dihydroxypropan-2-yl hexadecanoate (i.e., a 1-monoacylglyceride) and 1,3-dihydroxypropan-2-yl hexadecanoate (i.e., a 2-monoacylglyceride) dissolved in a mixture of 80% ethanol and 20% water at a concentration of 40 mg/mL.

Limes were harvested simultaneously and divided into two groups of six limes each, each of the groups being qualitatively identical (i.e., all groups had limes of approximately the same average size and quality). The first group of limes (corresponding to FIG. 14A) was treated with the solution of 2,3-dihydroxypropan-2-yl hexadecanoate and 1,3-dihydroxypropan-2-yl hexadecanoate (coating agent) in pure ethanol (sanitizing agent), and the second group (corresponding to FIG. 14B) was treated with the solution of 2,3-dihydroxypropan-2-yl hexadecanoate and 1,3-dihydroxypropan-2-yl hexadecanoate (coating agent) in the mixture of 80% ethanol (sanitizing agent) and 20% water.

Each of the treatments above, which served to sanitize the limes and form coatings, was performed as follows. The limes were placed in bags, and the solution containing the sanitizing agent and the coating agent was poured into the bag. The bag was then sealed and lightly agitated until the entire surface of each lime was wet. The limes were then removed from the bag and allowed to dry on drying racks. The limes were kept under ambient room conditions at a temperature in the range of 23° C.-27° C. and humidity in the range of 40%-55% while they dried and for the entire duration of the time they were tested.

FIG. 14A is a high resolution photograph of one of the limes that was treated with the first solution (30:70 mixture of 2,3-dihydroxypropan-2-yl hexadecanoate and 1,3-dihydroxypropan-2-yl hexadecanoate dissolved in pure ethanol), and FIG. 14B is a high resolution photograph of one of the limes that was treated with the second solution (30:70 mixture of 2,3-dihydroxypropan-2-yl hexadecanoate and 1,3-dihydroxypropan-2-yl hexadecanoate dissolved in 80% ethanol). For the limes treated with the 100% ethanol solution (FIG. 14A), the solvent contacted the surfaces of the limes for about 30-60 seconds before completely evaporating away, after which the coating agent remained on the surfaces. For the limes treated with the 80% ethanol solution (FIG. 14B), the solvent contacted the surfaces of the limes for about 10 minutes before completely evaporating away, after which the coating agent remained on the surfaces. The images in FIGS. 14A and 14B are similar to and representative of all the other limes in the respective groups. Visible skin breakdown was observed in all the limes treated with the 100% ethanol solution (FIG. 14A), whereas the limes treated with the 80% ethanol solution (FIG. 14B) all appeared undamaged and were otherwise unaltered in appearance by the treatment.

Example 14

Spores Germinate on Top of Coating Compositions 2,3-dihydroxypropan-2-yl hexadecanoate and 1,3-dihydroxypropan-2-yl hexadecanoate (i.e., a coating composition) were combined in a 30:70 ratio and dissolved in 100% ethanol at a concentration of 10 mg/mL to form a solution.

10 µL of the solution was deposited onto glass slides coated with fruit wax. The solvent (ethanol) was allowed to evaporate, leaving a residue of coating composition. 20 µL droplets of spores of either *Colletotrichum* or *Botrytis* spp. suspended in sterile water at a concentration of ~$10^4$ spores/mL were deposited on top of the coated slides. The samples were incubated for 24 hours at 20° C. at approximately 90% relative humidity, stained with lactophenol blue dye (diluted to 20% strength in sterile water), and imaged using a light microscope. Five samples per condition (i.e., *Colletotrichum* and *Botrytis* spp) were studied.

Figure 20A:
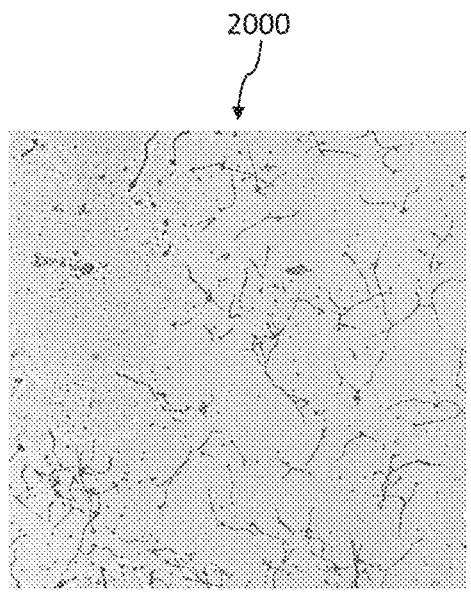
FIGS. 20A, 20B, and 20D show photos of *Penicillium* spores after incubation on slides coated with fruit wax and after treatment with various concentrations of ethanol and water.
Figure 20B:
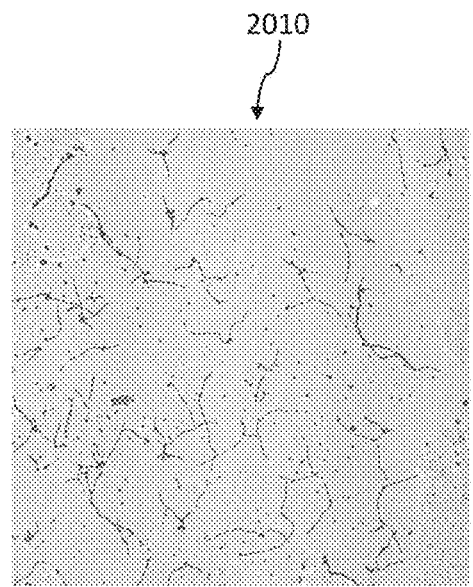
Figure 20C:
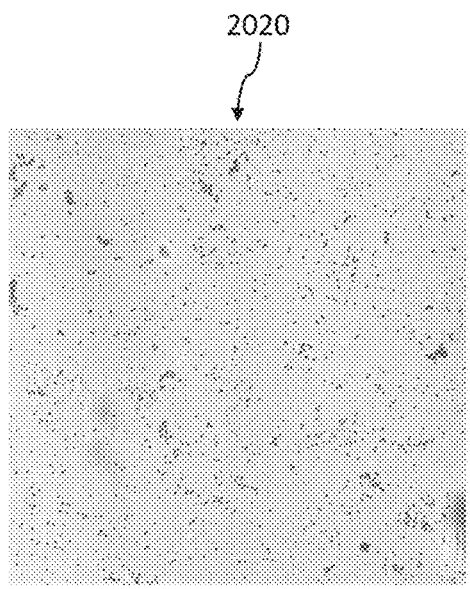
Figure 20D:
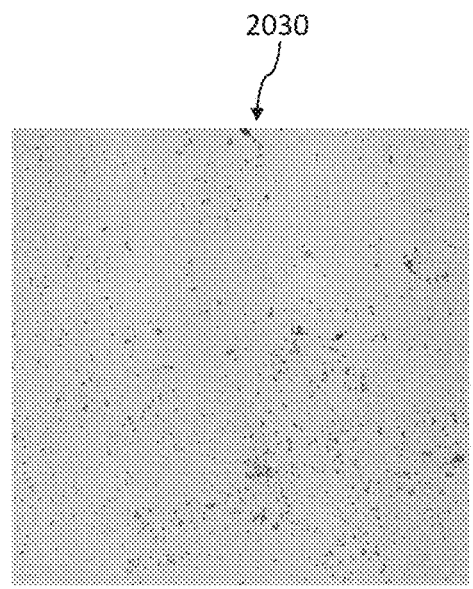
Figure 21A:
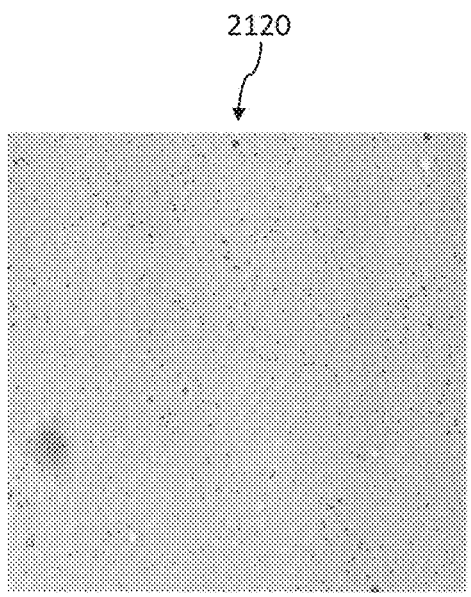
FIGS. 21A-21B show photos of *Penicillium* spores after incubation on slides coated with fruit wax and after treatment with various concentrations of ethanol and water in the presence of a coating composition of the present disclosure.
Figure 21B:
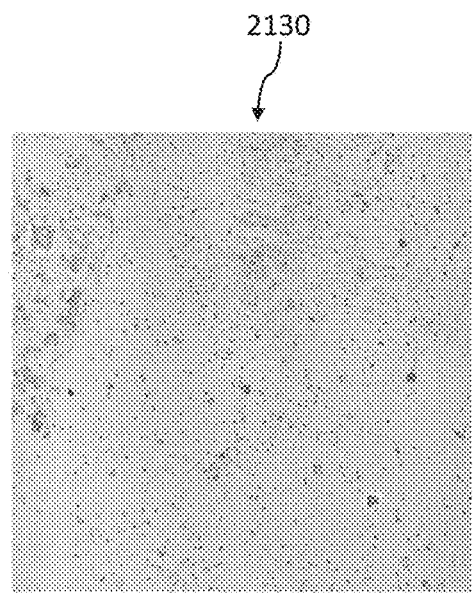

FIG. 15A shows a microscope image 1500 of a coated slide after administration of *Colletotrichum* spores 1502. The image is representative of all five samples examined. It was found that over 95% of *Colletotrichum* spores germinated on top of the coating composition.

FIG. 15B shows a microscope image 1510 of a coated slide after administration of *Botrytis* spores 1512. The image is representative of all five samples examined. It was found that over 95% of *Botrytis* spores germinated on top of the coating composition.

Example 15

Ethanol/water Mixtures Composed of 30% or Greater Ethanol Inhibit Germination and Growth of Spores 20 μL droplets of spores of either *Colletotrichum* or *Botrytis* spp. suspended in sterile water at a concentration of ~$10^4$ spores/mL were deposited on top of microscope slides coated with fruit wax. The spores were allowed to settle for 30 minutes and the water droplet was aspirated off with a Kimwipe.

On top of the spore-treated slides was deposited 10 μL of a solution of 0%, 10%, 30%, 50%, 70%, 90%, or 100% ethanol in deionized, sterile water; or 10 μL of 70%, 90% or 100% ethanol solutions containing 10 mg/mL of 2,3-dihydroxypropan-2-yl hexadecanoate and 1,3-dihydroxypropan-2-yl hexadecanoate at a ratio of 30:70. After 10 minutes, any remaining solvent was aspirated off with a Kimwipe and a 20 μL droplet of sterile, deionized water was deposited onto each sample. The samples were incubated for 24 hours at 20° C. at approximately 90% relative humidity, stained with lactophenol blue dye (diluted to 20% strength in sterile water), and imaged on a light microscope. For each spore species and each experimental condition, five samples were studied.

FIGS. 16A-16G and 17A-17C show representative microscope images (1600, 1610, 1620, 1630, 1640, 1650, 1660, 1740, 1750, and 1760, respectively) of *Colletotrichum*-coated slides after treatment with the compositions described above. FIG. 16A corresponds to treatment with water (0% ethanol). FIG. 16B corresponds to treatment with a 10% ethanol solution. FIG. 16C corresponds to treatment with a 30% ethanol solution. FIG. 16D corresponds to treatment with a 50% ethanol solution. FIG. 16E corresponds to treatment with a 70% ethanol solution. FIG. 16F corresponds to treatment with a 90% ethanol solution. FIG. 16G corresponds to treatment with pure ethanol. FIG. 17A corresponds to treatment with a 70% ethanol solution containing 10 mg/mL of 2,3-dihydroxypropan-2-yl hexadecanoate and 1,3-dihydroxypropan-2-yl hexadecanoate at a ratio of 30:70. FIG. 17B corresponds to treatment with a 90% ethanol solution containing 10 mg/mL of 2,3-dihydroxypropan-2-yl hexadecanoate and 1,3-dihydroxypropan-2-yl hexadecanoate at a ratio of 30:70. FIG. 17C corresponds to treatment with pure ethanol containing 10 mg/mL of 2,3-dihydroxypropan-2-yl hexadecanoate and 1,3-dihydroxypropan-2-yl hexadecanoate at a ratio of 30:70. Each image is representative of the other four samples examined. Spores in the various images are numbered 1602, 1612, 1622, 1632, 1642, 1652, 1662, 1742, 1752, and 1762. For the sake of clarity, only one spore is labeled per image.

FIGS. 18A-18G and 19A-19C show representative microscope images (1800, 1810, 1820, 1830, 1840, 1850, 1860, 1890, 1950, and 1960, respectively) of *Botrytis*-coated slides after treatment with the compositions described above. FIG. 18A corresponds to treatment with water (0% ethanol). FIG. 18B corresponds to treatment with a 10% ethanol solution. FIG. 18C corresponds to treatment with a 30% ethanol solution. FIG. 18D corresponds to treatment with a 50% ethanol solution. FIG. 18E corresponds to treatment with a 70% ethanol solution. FIG. 18F corresponds to treatment with a 90% ethanol solution. FIG. 18G corresponds to treatment with pure ethanol. FIG. 19A corresponds to treatment with a 70% ethanol solution containing mg/mL of 2,3-dihydroxypropan-2-yl hexadecanoate and 1,3-dihydroxypropan-2-yl hexadecanoate at a ratio of 30:70. FIG. 19B corresponds to treatment with a 90% ethanol solution containing 10 mg/mL of 2,3-dihydroxypropan-2-yl hexadecanoate and 1,3-dihydroxypropan-2-yl hexadecanoate at a ratio of 30:70. FIG. 19C corresponds to treatment with pure ethanol containing 10 mg/mL of 2,3-dihydroxypropan-2-yl hexadecanoate and 1,3-dihydroxypropan-2-yl hexadecanoate at a ratio of 30:70. Each image is representative of the other four samples examined. Spores in the various images are numbered 1802, 1812, 1822, 1832, 1842, 1852, 1862, 1942, 1952, and 1962. For the sake of clarity, only one spore is labeled per image.

It was found that samples exposed to ethanol/water solutions with less than 30% ethanol composition exhibited greater than 95% germination of spores. In contrast, samples exposed to solutions with 30% or greater ethanol content, both with and without coating compositions dissolved in the solution, exhibited less than 2% germination.

Example 16

Effect of Ethanol Concentration and Contact Time on *Penicillium* Spore Growth and Germination 20 μL droplets of spores of *Penicillium* spp. suspended in sterile water at a concentration of ~$10^5$ spores/mL were deposited on top of microscope slides coated with fruit wax. The spores were allowed to settle for 30 minutes and the water droplet was aspirated off with a Kimwipe.

On top of the spore-treated slides was deposited 10 μL of a solution of 0%, 30%, 70%, or 100% ethanol in deionized, sterile water; or 10 μL of 70% or 100% ethanol solutions containing 10 mg/mL of 2,3-dihydroxypropan-2-yl octadecanoate and 1,3-dihydroxypropan-2-yl hexadecanoate at a ratio of 30:70. After either 5 seconds, 10 seconds, 1 minute, or 10 minutes, any remaining solvent was aspirated off with a Kimwipe and a 20 μL droplet of sterile, deionized water was deposited onto each sample. The samples were incubated for 24 hours at 20° C. at approximately 90% relative humidity, stained with lactophenol blue dye (diluted to 20% strength in sterile water), and imaged on a light microscope. For each experimental condition, five samples were studied.

FIGS. 20A-20D and 21A-21B show representative microscope images (2000, 2010, 2020, 2030, 2120, and 2130, respectively) of the *Penicillium*-coated slides after treatment with the compositions described above. FIG. 20A corresponds to treatment with water (0% ethanol). FIG. 20B corresponds to treatment with a 30% ethanol solution. FIG. 20C corresponds to treatment with a 70% ethanol solution. FIG. 20D corresponds to treatment with pure ethanol. FIG. 21A corresponds to treatment with a 70% ethanol solution containing 10 mg/mL of 2,3-dihydroxypropan-2-yl octadecanoate and 1,3-dihydroxypropan-2-yl hexadecanoate at a ratio of 30:70. FIG. 21B corresponds to treatment with pure ethanol containing 10 mg/mL of 2,3-dihydroxypropan-2-yl octadecanoate and 1,3-dihydroxypropan-2-yl hexadecanoate at a ratio of 30:70. Each image is representative of the other four samples examined.

FIG. 22 is a table showing percent germination of *Penicillium* spores for each of the conditions described above. For 0 second solvent contact time (control samples that were not treated with the solutions), greater than 85% germination of spores was observed on all samples. For 5 second solvent contact time, the samples treated with sterile DI water and 30% ethanol solution exhibited greater than 85% germination of spores, while the samples treated with 70% and 100% ethanol solutions (both with and without coating agents dissolved in the solutions) exhibited less than 2% spore germination. For 10 second, 1 minute, and 10 minute solvent contact times, the samples treated with sterile DI water exhibited greater than 85% germination of spores, the samples treated with 30% ethanol solution exhibited about 60% germination of spores, and the samples treated with 70% and 100% ethanol solutions (both with and without coating agents dissolved in the solutions) exhibited less than 2% spore germination.

Various implementations of the compositions and methods have been described above. However, it should be understood that they have been presented by way of example only, and not limitation. For example, solutions including any of the solutions including coating agents dissolved in solvents described herein can also be applied to other substrates to sanitize the substrates and form protective coatings over the substrates in a single application step. For example, the solutions can be applied to meat, poultry, plants, textiles/clothing material, or other substrates, including non-edible substrates, in order to sanitize the substrates and form a protective coating over the substrates in a single application step. Where methods and steps described above indicate certain events occurring in certain order, those of ordinary skill in the art having the benefit of this disclosure would recognize that the ordering of certain steps may be modified and such modification are in accordance with the variations of the disclosure. The implementations have been particularly shown and described, but it will be understood that various changes in form and details may be made. Accordingly, other implementations are within the scope of the following claims.

The invention claimed is:

1. A method of treating produce, comprising:
providing a solution comprising a coating agent dissolved in a solvent, wherein the coating agent comprises monoacylglycerides and the solvent is at least 30% ethanol by volume;
applying the solution to a surface of the produce to sanitize the produce; and
at least partially removing the solvent from the surface of the produce and causing a protective coating to be formed from the coating agent over the surface of the produce.

2. The method of claim 1, wherein the coating agent comprises at least one of monomers, oligomers, fatty acids or salts thereof, esters, amides, amines, thiols, carboxylic acids, ethers, or aliphatic waxes.

3. The method of claim 1, wherein the solvent further comprises water.

4. The method of claim 1, wherein the-coating agent is a non-sanitizing coating agent.

5. The method of claim 1, wherein the protective coating prevents damage to the produce caused by the ethanol.

6. The method of claim 1, wherein the protective coating reduces a rate of water loss from the produce.

7. The method of claim 1, wherein the solution contacts the surface of the produce for at least 10 seconds.

8. A method of treating produce with a sanitizing solution, the sanitizing solution comprising a coating agent dissolved in a solvent, wherein the coating agent comprises monoacylglycerides and the solvent is at least 30% ethanol by volume, the method comprising:
applying the sanitizing solution to a surface of the produce;
allowing the sanitizing solution to contact the surface of the produce for a time period sufficient for the sanitizing agent to reduce microbial levels on the surface; and
allowing the solvent to at least partially evaporate, thereby causing a protective coating to form over the surface of the produce from the coating agent.

9. The method of claim 8, wherein the coating agent includes at least one of monomers, oligomers, fatty acids or salts thereof, esters, amides, amines, thiols, carboxylic acids, ethers, or aliphatic waxes.

10. The method of claim 8, wherein the solvent further comprises water.

11. The method of claim 8, wherein the coating agent is formulated to prevent damage to the produce caused by the sanitizing agent.

12. The method of claim 8, wherein the coating agent is formulated such that the protective coating reduces a rate of water loss from the produce.

13. The method of claim 8, wherein the sanitizing solution includes between 50% and 90% ethanol by volume.

14. The method of claim 8, wherein the time period is in a range of 1 second to 3,600 seconds.

15. The method of claim 8, wherein a concentration of the coating agent dissolved in the solution is in a range of 0.5 mg/mL to 200 mg/mL.

16. A method of sanitizing and preserving produce, comprising:
providing a solution comprising water, ethanol, and a coating agent, wherein the coating agent comprises monomers, oligomers, fatty acids, esters, amides, amines, thiols, carboxylic acids, ethers, or aliphatic waxes, wherein the monomers, oligomers, fatty acids, esters, amides, amines, thiols, carboxylic acids, ethers, or aliphatic waxes are derived from plant matter, and wherein the solution is at least 30% ethanol by volume;
applying the solution to a surface of the produce, thereby sanitizing the produce; and
at least partially removing the water and the ethanol from the surface of the produce; wherein
at least a portion of the coating agent remains on the surface of the produce after the at least partial removal of the water and the ethanol.

17. The method of claim 16, wherein the portion of the coating agent that remains on the surface of the produce forms a protective coating that serves to prevent damage to the produce caused by the sanitizing agent.

18. The method of claim 16, wherein the portion of the coating agent that remains on the surface of the produce forms a protective coating that replaces or reinforces portions of the produce which are damaged by the sanitizing agent.

19. The method of claim 18, wherein the protective coating further serves to reduce a mass loss rate of the produce.

20. The method of claim 16, wherein the portion of the coating agent that remains on the surface of the produce forms an edible coating over the produce.

21. The method of claim 16, wherein the produce is a thin skinned fruit or a thin skinned vegetable.

22. The method of claim 16, wherein the monomers, oligomers, fatty acids, esters, amides, amines, thiols, carboxylic acids, ethers, or aliphatic waxes are derived from cutin.

23. The method of claim 16, wherein the monomers, oligomers, fatty acids, esters, amides, amines, thiols, carboxylic acids, ethers, or aliphatic waxes comprise one or more compounds of Formula I or salts thereof, wherein Formula I is:

(Formula I)

and wherein:
R is a 1-glycerol or a 2-glycerol optionally substituted with one or more $C_1$-$C_6$alkyl or hydroxy;
$R^1$, $R^2$, $R^5$, $R^6$, $R^9$, $R^{10}$, $R^{11}$, $R^{12}$, and $R^{13}$ are each independently —H, —$OR^{14}$, —$NR^{14}R^{15}$, —$SR^{14}$, halogen, —$C_1$-$C_6$alkyl, —$C_1$-$C_6$alkenyl, —$C_1$-$C_6$alkynyl, —$C_3$-$C_7$cycloalkyl, —$C_6$-$C_{10}$aryl, or 5 to 10-membered ring heteroaryl, wherein each —$C_1$-$C_6$alkyl, —$C_1$-$C_6$alkenyl, —$C_1$-$C_6$alkynyl, —$C_3$-$C_7$cycloalkyl, —$C_6$-$C_{10}$aryl, or 5 to 10-membered ring heteroaryl is optionally substituted with —$OR^{14}$, —$NR^{14}R^{15}$, $SR^{14}$, or halogen;
$R^3$, $R^4$, $R^7$ and $R^8$ are each independently —H, —$OR^{14}$, —$NR^{14}R^{15}$, $SR^{14}$, halogen, —$C_1$-$C_6$alkyl, —$C_1$-$C_6$alkenyl, —$C_1$-$C_6$alkynyl, —$C_3$-$C_7$cycloalkyl, —$C_6$-$C_{10}$aryl, or 5 to 10-membered ring heteroaryl wherein each —$C_1$-$C_6$alkyl, —$C_1$-$C_6$alkenyl, —$C_{10}$-$C_6$alkynyl, —$C_3$-$C_7$cycloalkyl, —$C_6$-$C_{10}$aryl, or 5 to 10-membered ring heteroaryl is optionally substituted with —$OR^{14}$, —$NR^{14}R^{15}$, —$SR^{14}$, or halogen; or
$R^3$ and $R^4$ and $R^7$ and $R^8$ can combine with the carbon atoms to which they are attached to form a 3 to 6-membered ring;
$R^{14}$ and $R^{15}$ are each independently —H, —$C_1$-$C_6$alkyl, —$C_1$-$C_6$alkenyl, or —$C_1$-$C_6$alkynyl;
the symbol ----- represents an optionally single or cis or trans double bond;
n is an integer between 0 and 8;
m is an integer between 0 and 3;
q is an integer between 0 and 5; and
r is an integer between 0 and 8.

24. A method of sanitizing and preserving produce, comprising:
providing a solution comprising water, ethanol, and a coating agent, wherein the coating agent comprises monoacylglycerides, and wherein the solution is at least 30% ethanol by volume;
applying the solution to a surface of the produce, thereby sanitizing the produce; and
at least partially removing the water and the ethanol from the surface of the produce; wherein
at least a portion of the coating agent remains on the surface of the produce after the at least partial removal of the water and the ethanol.

25. The method of claim 24, wherein the coating agent further comprises fatty acids or salts thereof.

26. A method of treating edible produce, comprising:
providing a solution comprising a coating agent dissolved in a solvent, the coating agent comprising monoacylglycerides, wherein the solvent comprises water and ethanol, and wherein the solvent is between 50% and 90% ethanol by volume;
applying the solution to a surface of the edible produce to sanitize the produce and to cause a protective coating to be formed over the surface of the produce from the coating agent; and
at least partially removing the solvent from the surface of the edible produce.

27. The method of claim 26, wherein applying the solution to the surface of the edible produce comprises dipping the edible produce in the solution.

28. The method of claim 26, wherein applying the solution to the surface of the edible produce comprises spraying the solution on the surface of the edible produce.

29. The method of claim 26, wherein the protective coating prevents damage to the produce caused by the ethanol.

* * * * *